United States Patent [19]
Chiocca et al.

[11] Patent Number: 5,688,773
[45] Date of Patent: Nov. 18, 1997

[54] METHOD OF SELECTIVELY DESTROYING NEOPLASTIC CELLS

[75] Inventors: E. Antonio Chiocca, Boston; David J. Waxman, Newton Centre; Ming X. Wei, Somerville; Xandra O. Breakefield, Newton; Ling Chen, Brookline, all of Mass.

[73] Assignees: The General Hospital Corporation; Boston University; Dana-Farber Cancer Institute, all of Boston, Mass.

[21] Appl. No.: 330,523

[22] Filed: Oct. 28, 1994

Related U.S. Application Data

[63] Continuation-in-part of Ser. No. 291,500, Aug. 17, 1994, abandoned.

[51] Int. Cl.$^6$ .............. A61K 48/00; C12N 5/00; C12N 15/00; C07N 14/00
[52] U.S. Cl. ............ 514/44; 424/93.1; 424/93.21; 435/172.3; 435/240.1; 435/240.2; 435/240.25; 435/320.1
[58] Field of Search .............. 424/93.21, 93.7; 935/54, 62; 435/172.3, 240.1, 240.2, 320.1; 514/2, 44

[56] References Cited

PUBLICATIONS

Marshall, Science 269:1050–1055, 1995.
Culver et al., Trends Genetics, 10(5):174–178, 1994.
Miller et al., FASEB Journal, 9;190–199, 1995.
Hodgson et al., Exp. Opin. Ther. Pat. 5(5):459–468, 1995.
Orkin et al. "Report and Recommendations . . . " Dec. 7, 1995, 1–40.
LaFont et al., Lancet 346:1442–1443, 1995.
Gutierrez et al, Gene Therapy for Cancer, The Lancet, vol. 339: Mar. 21, 1992 pp. 715–721.
Friedmann, T., Gene Therapy of Cancer Through Restoration of Tumor–Suppressor Functions, Cancer, vol. (6) 70, Sep. 15, 1992.
Culver et al, Science, vol. 256, 12, Jun. 1992 pp. 1550–1552.
Weber et al, Biochemical Pharmacology, vol. 45, 1993 pp. 1685–1694.
Manome et al, Cancer Research, 54, 5408–5413 Oct. 15, 1994.
Amano et al., "High Activity of Choline Acetyltransferase Induced in Neuroblastoma x Glia Hybrid Cells," *Exp. Cell Res.* 85:399–408 (1974).
Angier, N. "Tumor Treatment Showing Promise," *N.Y. Times, National Edition*, p. B11 (Sep. 8, 1993).
Araki et al., "The Essential Region for Assembly and Particle Formation in Hepatitis B Virus Surface Antigen Produced in Yeast Cells," *Gene* 89:195–201 (1990).

Arndt et al., "Intrathecal Administration of 4–Hydroperoxy-cyclophosphamide in Rhesus Monkeys," *Cancer Res.* 47:5932–5934 (1987).
Austin, F.C. and Boone, C.W., "Virus Augmentation of the Antigenicity of Tumor Cell Extracts," *Adv. Cancer Res.* 30:301–345 (1979).
Baker et al., "Suppression of Human Colorectal Carcinoma Cell Growth by Wild–Type p53," *Science* 249:912–915 (1990).
Barba et al., "Development of anti–tumor immunity following thymididine kinase–mediated killing of experimental brain tumors," *PNAS USA* 91:4348–4352 (1994).
Barker et al., "Cloning and Sequence Analysis of the Human Gene Encoding Eosinophil Major Basic Protein," *Gene* 86:285–289 (1990).
Barker et al., "Development of an Animal Brain Tumor Model and Its Response to Therapy with 1,3–Bis(2–chlorethyl–1–nitrosourea," *Cancer Res.* 33:976–983 (1973).
Beerman, W.F., "Meningeal Carcinomatosis," *JAMA* 58(19):1437–1439 (1912).
Benda et al., "Differentiated Rat Glial Cell Strain in Tissue Culture," *Science* 161:370–371 (1968).
Benda et al., "Morphological and immunochemical studies of rat glial tumors and clonal strains propagated in culture," *J. Neurosurg.* 34:310–323 (1971).
Bennett, J.E., "Antimicrobial Agents: Antifungal Agents," in: Goodman and Gilman's The Pharmacological Basis of Therapeutics, Gilman et al., eds., vol. 8, Pergamon Press: NY, NY, pp. 1165–1181 (1990).
Berends et al., "The Detection of Virally Induced Tumors by $^{131}$I–and $^{125}$I–Labeled Syngeneic Monoclonal Antibodies," *Cancer Immunol. Immunother.* 26:243–249 (1988).
Bernstein, A. and Breitman, M., "Genetic Ablation in Transgenic Mice," *Mol. Biol. Med.* 6:523–530 (1989).
Bignami et al., "Localization of the Glial Fibrillary Acidic Protein in Astrocytes by Immunofluorescence," *Brain Res.* 43:429–435 (1972).
Bigner et al. "Patterns of the Early, Gross Chromosomal Changes in Malignant Human Gliomas," *Hereditas* 101:103–113 (1984).

(List continued on next page.)

*Primary Examiner*—Jacqueline M. Stone
*Assistant Examiner*—Andrew Milne
*Attorney, Agent, or Firm*—Sterne, Kessler, Goldstein & Fox P.L.L.C.

[57] ABSTRACT

A method for selectively killing nervous system and peripheral neoplastic cells is provided. Viral vectors are used to selectively express a cytochrome P450 gene in neoplastic cells, whose gene product targets the cells for selective killing, by rendering the cells sensitive to a chemotherapeutic agent.

27 Claims, 33 Drawing Sheets

OTHER PUBLICATIONS

Bigner et al., "Specific Chromosomal Abnormalities in Malignant Human Gliomas," *Cancer Res.* 88:405–411 (1988).

Borrelli et al., "Transgenic Mice with Inducible Dwarfism," *Nature* 339:538–541 (1989).

Boviatsis et al., "Gene Transfer into Experimental Brain Tumors Mediated by Adenovirus, Herpes Simplex Virus, and Retrovirus Vectors," *Human Gene Ther.* 5:183–191 (1994).

Breakefield, X.O. and Geller, A.I., "Gene Transfer into the Nervous System," *Molec. Neurobiol.* 1:339–371 (1987).

Brem et al., "Biodegradable polymers for controlled delivery of chemotherapy with and without radiation therapy in the monkey brain," *J. Neurosurg.* 80:283–290 (1994).

Burger et al., "Computerized tomographic and pathologic studies of the untreated quiescent, and recurrent glioblastoma multiforme," *J. Neurosurg.* 58:159–169 (1983).

Burns et al., "Vesicular Stomatitis Virus G Glycoprotein Pseudotyped Retroviral Vectors: Concentration to Very High Titer and Efficient Gene Transfer Into Mammalian and Nonmammalian Cells," *PNAS USA* 90:8033–8037 (1993).

Capecchi, M.R., "The New Mouse Genetics: Altering the Genome by Gene Targeting," *TIG* 5(3):70–76 (1989).

Caruso et al., "Regression of Established Macroscopic Liver Metastases After In Situ Transduction of a Suicide Gene," *PNAS USA* 90:7024–7028 (1993).

Cepko, C., "Immortalization of Neural Cells via Retrovirus–Mediated Oncogene Transduction," *Ann. Rev. Neurosci.* 12:47–65 (1989).

Cepko, C., "Lineage Analysis and Immortalization of Neural Cells via Retrovirus Vectors," in: Neuromethods, vol. 16, Molecular Neurobiological Techniques, Bolton et al., eds., Clifton, NJ, Humana, pp. 177–219 (1989).

Cepko et al., "Preparation of a Specific Retrovirus Producer Cell Line," in: Current Protocols in Molec. Biol., Ausubel et al., eds., Wiley and Sons, NY, pp. 9.11.1–9.11.12 (1992).

Chana, T.K.H. and Waxman, D.J., "Cyclophosphamide Modulates Rat Hepatic Cytochrome P450 2C11 and Steroid 5α–Reductase Activity and Messenger RNA Levels through the Combined Action of Acrolein and Phosphoramide Mustard," *Cancer Res.* 53:2490–2497 (1993).

Chang et al., "Differential Activation of Cyclophosphamide and Ifosphamide by Cytochromes P–450 2B and 3A in Human Liver Microsomes," *Cancer Res.* 53:5629–5637 (1993).

Chang et al., "Evaluation of Triacetyloleandomycin, α–Naphthoflavone and Diethyldithiocarbamate as Selective Chemical Probes for Inhibition of Human Cytochromes P450," *Arch. Biochem. Biophys.* 311(2):437–442 (1994).

Cheng et al., "Photoradiation Therapy: Current Status and Applications in the Treatment of Brain Tumors," *Surg. Neurol.* 25:423–435 (1986).

Chiocca et al., "Virus–Mediated Genetic Treatment of Rodent Gliomas," in: Gene Therapeutics, Wolff, J.A., ed., Birkhauser Publ., Boston, MA, pp. 245–262 (1994).

Clarke, L. and Waxman, D.J., "Oxidative Metabolism of Cyclophosphamide: Identification of the Hepatic Monooxygenase Catalysts of Drug Activation," *Cancer Res.* 49:2344–2350 (1989).

Coen et al., "A Genetic Approach to Promoter Recognition During trans Induction of Viral Gene Expression," *Science* 234:53–59 (1986).

Coen et al., "Thymidine Kinase–Negative Herpes Simplex Virus Mutants Establish Latency in Mouse Trigeminal Ganglia but do not Reactivate," *PNAS USA* 86:4736–4740 (1989).

Colvin, M., "Alkylating Agents and Platinum Antitumor Compounds," in: Cancer Medicine, Holland et al., eds., Lea and Febiger, Philadelphia, PA, pp. 733–754 (1993).

Colvin, M. and Hilton, J. "Pharmacology of Cyclophosphamide and Metabolites," *Cancer Treat. Rep.* 65 (Suppl. 3):89–95 (1981).

Cone, R.D. and Mulligan, R.C., "High–efficiency gene transfer into mammalian cells: Generation of helper–free recombinant retrovirus with broad mammalian host range," *PNAS USA* 81:6349–6353 (1984).

Corey et al., "Infections With Herpes Simplex Viruses, Part I," *New Engl. J. Med.* 314(11):686–691 (1986).

Corey et al., "Infections With Herpes Simplex Viruses, Part II," *New Engl. J. Med.* 314(12):749–757 (1986).

Cox, P.J., "Cyclophosphamide Cystitis—Identification of Acrolein as the Causative Agent," *Biochem. Pharmacol.* 28:2045–2049 (1979).

Culver et al., "In Vivo Gene Transfer with Retroviral Vector–Producer Cells for Treatment of Experimental Brain Tumors," *Science* 256:1550–1552 (1992).

Danos, O. and Mulligan, R.C., "Safe and Efficient Generation of Recombinant Retroviruses with Amphotropic and Ecotropic Host Ranges," *PNAS USA* 85:6460–6464 (1988).

Das, G.D. and Altman, J., "Postnatal neurogenesis in the caudate nucleus and nucleus accumbens septi in the rat," *Brain Res.* 21:122–127 (1970).

Daumas–DuDort et al. "Grading of Astrocytomas, A Simple and Reproducible Method," *Cancer* 62(10):2152–2165 (1988).

Doehmer et al., "Genetically Engineered V79 Chinese Hamster Cells Metabolically Activate the Cytostatic Drugs Cyclophosphamide and Ifosfamide," *Environ. Health Perspectives* 88:63–65 (1990).

Doehmer et al., "Stable expression of rat cytochrome P–450IIB1 cDNA in Chinese hamster cells (V79) and metabolic activation of aflotoxin $B_1$," *PNAS USA* 85:5769–5773 (1988).

Dranoff et al., "Vaccination with irradiated tumor cells engineered to secrete murine granulocyte–macrophage colony–stimulating factor stimulates potent, specific, and long–lasting anti–tumor immunity," *PNAS USA* 90:3539–3543 (1993).

El–Azouzi et al., "Loss of Distinct Regions on the Short Arm of Chromosome 17 Associated with Tumorigenesis of Human Astrocytomas," *PNAS USA* 86:7186–7190 (1989).

Elion, G.B., "The biochemistry and mechanism of action of acyclovir," *J. Antimicrob. Chemother.* 12, Suppl. B:9–17 (1983).

Ezzedine et al., "Selective Killing of Glioma Cells in Culture and in Vivo by Retrovirus Transfer of the Herpes Simplex Virus Thymidine Kinase Gene," *New Biologist* 3(6):608–614 (1991).

Ezzedine et al., "Selective Killing of Rat C6 Glioma Cells Following Retrovirus–Mediated Transfer of the Herpes Simplex Virus Thymidine Kinase Gene," *Soc. Neurosci. Abstr.* 16:Part 1, Abstract 189.3 (1990).

Frederiksen et al., "Immortalization of Precursor Cells from the Mammalian CNS," *Neuron* 1:439–448 (1988).

Freeman et al., "The 'Bystander Effect': Tumor Regression When a Fraction of the Tumor Mass Is Genetically Modified," *Cancer Res.* 53:5274–5283 (1993).

Freeman et al., "Tumor Regression when a Fraction of the Tumor Mass Contains the HSV-TK Gene," *J Cell Biochem.* 16F:47 Abstract No. V 209 (1992).

Friedman et al., "Experimental Chemotherapy of Human Medulloblastoma with Classical Alkylators," *Cancer Res.* 46:2827–2833 (1986).

Friedman et al., "Glutathione Protects Cardiac and Skeletal Muscle from Cyclophospamide–induced Toxicity," *Cancer Res.* 50:2455–2462 (1990).

Friedman et al., "Phase I trial of intrathecal 4–hydroperoxy-cyclophosphamide for neoplastic meningitis," *Proc. Amer. Assoc. Cancer Res.* 34:269 Abstract No. 1598 (1993).

Friedmann, T., "Progress Toward Human Gene Therapy," *Science* 244:1275–1281 (1989).

Fuchs et al., "Activity of Intrathecal 4–Hydroperoxycyclophosphamide in a Nude Rat Model of Human Neoplastic Meningitis," *Cancer Res.* 50:1954–1959 (1990).

Fyfe et al., "Thymidine Kinase from Herpes Simplex Virus Phosphorylates the New Antiviral Compound, 9–(2–Hydroxyethoxymethyl)guanine," *J. Biol. Chem.* 253(24):8721–8727 (1978).

Gage et al., "Grafting Genetically Modified Cells to the Brain: Possibilities for the Future," *Neuroscience* 23(3):795–807 (1987).

Gannon, V.P.J., "Molecular Cloning and Nucleotide Sequence of Another Variant of the *Escherichia coli* Shiga--like Toxin II Family," *J. General Microbiol.* 136:1125–1135 (1990).

Gansbacher et al., "Retroviral Vector–mediated γ–Interferon Gene Transfer into Tumor Cells Generates Potent and Long Lasting Antitumor Immunity," *Cancer Res.* 50:7820–7825 (1990).

Geller, A.I., "A New Method to Propagate Defective HSV–1 Vectors," *Nucl. Acids Res.* 16(12):5690 (1988).

Geller, A.I. and Breakefield, X.O., "A Defective HSV–1 Vector Expresses *Escherichia coli* β–Galactosidase in Cultured Peripheral Neurons," *Science* 241:1667–1669 (1988).

Geller, A.I. and Freese, A., Infection of Cultured Central Nervous System Neurons with a Defective Herpes Simplex Virus 1 Vector Results in Stable Expression of *Escherichia coli* β–Galactosidase. *PNAS USA* 87:1149–1153 (1990).

Genka et al., "Brain and plasma pharmacokinetics and anticancer activities of cyclophosphamide and phosphoramide mustard in the rat," *Cancer Chemother. Pharmacol.* 27:1–7 (1990).

Gilboa, E., "Retroviral Gene Transfer: Applications to Human Therapy," in: Biology of Hematopoiesis, Wiley–Liss, Inc., pp. 301–311 (1990).

Gilboa, E., "Retrovirus Vectors and their Uses in Molecular Biology," *BioEssays* 5(6):252–257 (1987).

Gilboa et al., "Transfer and Expression of Cloned Genes Using Retroviral Vectors," *Biotechniques* 4(6):504–512 (1986).

Glatstein et al., "The Imaging Revolution and Radiation Oncology: Use of CT, Ultrasound, and NMR for Localization. Treatment Planning and Treatment Delivery," *Intl. J. Radiation Oncology Biol. Phys.* 11(2):299–314 (1985).

Gray et al., "Radial Arrangement of Clonally Related Cells in the Chicken Optic Tectum: Lineage Analysis with a Recombinant Retrovirus," *PNAS USA* 85:7356–7360 (1988).

Guengerich, F.P., "Oxidation of Toxic and Carcinogenic Chemicals by Human Cytochrome P–450 Enzymes," *Chem. Res. Toxicol.* 4(4):391–407 (1991).

Gurtoo et al., "Role of Glutathione in the Metabolism–dependent Toxicity and Chemotherapy of Cyclophosphamide," *Cancer Res.* 41:3584–3591 (1981).

Gutin et al., "Recurrent Malignant Gliomas: Survival Following Interstitial Brachytherapy with High–Activity Iodine–125 Sources," *J. Neurosurg.* 67:864–873 (1987).

Hanada et al., "Combined Effects of Acyclovir and Human Interferon–α on Herpes Simplex Virus Replication in Cultured Neural Cells," *J. Med. Virol.* 29:7–12 (1989).

Hatton, J.D., "Migration of Grafted Neonatal Astrocytes in Neonatal and Adult Hosts," *Soc. Neurosci. Abstr.* 15(2):1369 Abstract No. 539.8 (1989).

Heimbrook et al., "Transforming Growth Factor α–Pseudomonas Exotoxin Fusion Protein Prolongs Survival of Nude Mice Bearing Tumor Xenografts," *PNAS USA* 87:4697–4701 (1990).

Henson, J.W. and Posner, J.B., "Neurological Complications," in: Cancer Medicine, Holland et al., eds., Lea and Febiger, Philadelphia, PA, pp. 2268–2286 (1993).

Heyman et al., "Thymidine kinase obliteration: Creation of transgenic mice with controlled immune deficiency," *PNAS USA* 86:2698–2702 (1989).

Hodgson et al., "Expression analysis of the mixed function oxidase system in rat brain by the polymerase chain reaction," *Mol. Cell Biochem.* 120:171–179 (1993).

Hohorst et al., "The Enzymatic Basis of Cyclophosphamide Specificity," *Adv. Enzyme Regul.* 25:99–122 (1986).

Hong et al., "Pharmacokinetics of 4–Hydroxycyclophosphamide and Metabolites in the Rat," *Drug Metab. Dispos.* 19(1): 1–7 (1991).

Horellou et al., "Behavioural Effect of Engineered Cells that Synthesize L–DOPA or Dopamine after Grafting into the Rat Neostriatum," *Eur. J. Neurosci.* 2:116–119 (1990).

Huang et al., "Suppression of the Neoplastic Phenotype by Replacement of the RB Gene in Human Cancer Cells," *Science* 242:1563–1566 (1988).

Huber et al., "In Vivo Antitumor Activity of 5–Fluorocytosine on Human Colorectal Carcinoma Cells Genetically Modified to Express Cytosine Deaminase," *Cancer Res.* 53:4619–4626 (1993).

Huber et al., "Retroviral–Mediated Gene Therapy for the Treatment of Hepatocellular Carcinoma: An Innovative Approach for Cancer Therapy," *PNAS USA* 88:8039–8043 (1991).

Ito et al., "Cloning and Nucleotide Sequencing of Vero Toxin 2 Variant Genes from *Escherichia coli* O91: H21 Isolated from a Patient with the Hemolytic Uremic Syndrome," *Microbial Pathogen.* 8:47–60 (1990).

Izant, J.G. and Weintraub, H., "Constitutive and Conditional Suppression of Exogenous and Endogenous Genes by Anti--Sense RNA," *Science* 229:345–352 (1985).

Jacque et al., "Interspecies Identification of Astrocytes after Intracerebral Transplantation," *Dev. Neurosci.* 8:142–149 (1986).

James et al., "Clonal Genomic Alterations in Glioma Malignancy Stages," Cancer Res. 48:5546–5551 (1988).

Jefferson et al. "Posttranscriptional Modulation of Gene Expression in Cultured Rat Hepatocytes," *Mol. Cell Biol.* 4(9):1929–1934 (1984).

Jowett et al., "Mammalian genes expressed in Drosophila: a transgenic model for the study of mechanisms of chemical mutagenesis and metabolism," *EMBO J.* 10(5):1075–1081 (1991).

Kabat, D., "Molecular Biology of Friend Viral Erythroleukemia," *Curr. Topics in Microbiol. and Immunol.* 148:1–42 (1989).

Kay et al., "Retrovirus–Induced Spongiform Myeloencephalopathy in Mice: Regional Distribution of Infected Target Cells and Neuronal Loss Occurring in the Absence of Viral Expression in Neurons," *PNAS USA* 88:1281–1285 (1991).

Kim, S.K. and Wold, B.J., "Stable Reduction of Thymidine Kinase Activity in Cells Expressing High Levels of Anti-Sense RNA," *Cell* 42:129–138 (1985).

Kim et al., "Correlates of Survival and the Daumas–Duport Grading System for Astrocytomas," *J. Neurosurg.* 74:27–37 (1991).

Kobayashi, H., "Viral Xenogenization of Intact Tumor Cells," *Advances in Cancer Res.* 30:279–299 (1979).

Le Blanc, G.A. and Waxman, D.J. "Interaction of Anticancer Drugs with Hepatic Monooxygenase Enzymes," *Drug Metab. Rev.* 20(2–4):395–439 (1989).

Le Doussal et al., "Targeting of Indium 111–labeled Bivalent Hapten to Human Melanoma Mediated by Bispecific Monoclonal Antibody Conjugates: Imaging of Tumors Hosted in Nude Mice," *Cancer Res.* 50:3445–3452 (1990).

Lee et al., "Growth of Human Schwannomas in the Subrenal Capsule of the Nude Mouse," *Neurosurg.* 26(4):598–605 (1990).

Lendahl et al., "CNS Stem Cells Express a New Class of Intermediate Filament Protein," *Cell* 60:585–595 (1990).

Li Bi et al., "In Vitro Evidence That Metabolic Cooperation Is Responsible for the Bystander Effect Observed with HSV tk Retroviral Gene Therapy," *Hum. Gene Ther.* 4:725–731 (1993).

Luskin et al., "Cell Lineage in the Cerebral Cortex of the Mouse Studied In Vivo and In Vitro with a Recombinant Retrovirus," *Neuron* 1:635–647 (1988).

Macchi et al., "Effect of Human T Lymphotropic Retrovirus–I Exposure on Cultured Human Glioma Cell Lines," *Acta Neuropathol.* 81:670–674 (1991).

Mahaley et al., "National Survey of Patterns of Care for Brain–Tumor Patients," *J. Neurosurg.* 71:826–836 (1989).

Mann et al., "Construction of a Retrovirus Packaging Mutant and its Use to Produce Helper–Free Defective Retrovirus," *Cell,* 33:153–159 (1983).

Manome et al., "Enhancer Sequences of the DF3 Gene Regulate Expression of the Herpes Simplex Virus Thymidine Kinase Gene and Confer Sensitivity of Human Breast Cancer Cells to Ganciclovir," *Cancer Res.* 54:5408–5413 (1994).

Martuza et al., "Experimental Therapy of Human Glioma by Means of a Genetically Engineered Virus Mutant," *Science* 252:854–856 (1991).

Matz et al., "Physical Mapping of Temperature–sensitive Mutations of Herpes Simplex Virus Type 1 Using Cloned Restriction Endonuclease Fragments," *J. gen. Virol.* 64:2261–2270.

McGarry, T.J. and Lindquist, S., "Inhibition of Heat Shock Protein Synthesis by Heat–Inducible Antisense RNA," *PNAS USA* 83:399–403 (1986).

McKnight, S.L., "The Nucleotide Sequence and Transcript Map of the Herpes Simplex Virus Thymidine Kinase Gene," *Nucl. Acids Res.* 8(24):5949–5964 (1980).

McLaren et al., "Preclinical Investigations of FIAU, an Anti–Herpes Agent," *Herpes Viruses and Virus Chemotherapy* pp. 57–61 (1985).

Melton, D.A., "Infected Anti–Sense RNAs Specifically Block Messenger RNA Translation In Vivo," *PNAS USA* 82:144–148 (1985).

Miller A.D. and Buttimore, C., "Redesign of Retrovirus Packaging Cell Lines To Avoid Recombination Leading to Helper Virus Production," *Molec. Cell. Biol.* 6(8):2895–2902 (1986).

Miller et al., "Gene Transfer by Retrovirus Vectors Occurs Only in Cells That Are Actively Replicating at the Time of Infection," *Mol. Cell Biol.* 10(8):4239–4242 (1990).

Miyanohara et al., "Expression of Hepatitis B Surface Antigen Gene in Yeast," *PNAS USA* 80:1–5 (1983).

Monier et al., "Signals for the Incorporation and Orientation of Cytochrome P450 in the Endoplasmic Reticulum Membrane," *J. Cell Biol.* 107:457–470 (1988).

Moolten, F.L., "Tumor Chemosensitivity Conferred by Inserted Herpes Thymidine Kinase Genes: Paradigm for a Prospective Cancer Control Strategy," *Cancer Res.* 5276–5281 (1986).

Moolten, F.L. and Wells, J.M., "Curability of Tumors Bearing Herpes Thymidine Kinase Genes Transferred by Retroviral Vectors," *J. Natl. Cancer Inst.* 82(4):297–300 (1990).

Moolten et al., "Lymphoma Regression Induced by Ganciclovir in Mice Bearing a Herpes Thymidine Kinase Transgene," *Human Gene Ther.* 1:125–134 (1990).

Mroz, P.J. and Moolten, F.L., "Retrovirally Transduced *Escherichia coli* gpt Genes Combine Selectability with Chemosensitivity Capable of Mediating Tumor Eradication," *Human Gene Ther.* 4:589–595 (1993).

Mullen et al., "Transfer of the bacterial gene for cytosine deaminase to mammalian cells confers lethal sensitivity to 5–fluorocytosine: A negative selection system," *PNAS USA* 89:33–37 (1992).

Mullen et al., "Tumors Expressing the Cytosine Deaminase Suicide Gene Can Be Eliminated in Vivo with 5–Fluorocytosine and Induce Protective Immunity to Wild Type Tumor," *Cancer Res.* 54:1503–1506 (1994).

Nagashima, T. and Hoshino, T., "Rapid Detection of S–Phase Cells by Anti–bromodeoxyuridine Monoclonal Antibody in 9L Brain Tumor Cells In Vitro and In Situ," *Acta Neuropathol.* 66:12–17 (1985).

Nelson et al., "The P450 Superfamily: Update on New Sequences, Gene Mapping Accession Numbers, Early Trivial Names of Enzymes, and Nomenclature," *DNA and Cell Biol.* 12(1):1–51 (1993).

Ng, S. and Waxman, D.J., "Activation of thio–TEPA cytotoxicity toward human breast cancer cells by hepatic cytochrome P450," *Intl. J. Oncol.* 2:731–738 (1993).

Ng, S. and Waxman, D.J., "Biotransformation of N,N', N"–Triethylenethiophosphoramide: Oxidative Desulfuration to Yield N,N',N"–Triethylenephosporamide associated with Suicide Inactivation of a Phenobarbital–inducible Hepatic P–450 Monooxygenase," *Cancer Res.* 50:464–471 (1990).

Ng, S. and Waxman, D.J., "N,N', N"–Triethylenetiophosporamide (Thio–TEPA) Oxygenation by Constitutive Hepatic P450 Enzymes and Modulation of Drug Metabolism and Clearance in Vivo by P450–inducing Agents," *Cancer Res.* 51:2340–2345 (1991).

Oldfield et al., "Clinical Protocols—Gene Therapy for the Treatment of Brain Tumors Using Intra–Tumoral Transduction with the Thymidine Kinase Gene and Intravenous Ganciclovir," *Human Gene Ther.* 4:39–69 (1993).

Olson et al., "Infiltration of the Leptomeninges by Systemic Cancer," *Arch. Neurol.* 30:122–137 (1974).

Palabrica et al., "Thrombus Imaging in a Primate Model with Antibodies Specific for an External Membrane Protein of Activated Platelets," *PNAS USA* 86:1036–1040 (1989).

Palella et al., "Herpes Simplex Virus–Mediated Human Hypoxanthine–Guanine Phosphoribosyltransferase Gene Transfer into Neuronal Cells," *Molec. Cell. Biol.* 8(1):457–460 (1988).

Pestka et al., "Anti–mRNA: Specific inhibition of translation of single mRNA molecules," *PNAS USA* 81:7525–7528 (1984).

Peter et al., "Studies on 4–Hydroperoxycyclophosphamide (NSC–181815): A Simple Preparation Method and its Application for the Synthesis of a New Class of 'Activated' Sulfur–Containing Cyclophosphamide (NSC–26271) Derivatives," *Cancer Treat. Rep.* 60(4):429–435 (1976).

Phillips et al., "Intrathecal 4–Hydroperoxycyclophosphamide: Neurotoxicity, Cerebrospinal Fluid Pharmacokinetics, and Antitumor Activity in a Rabbit Model of VX2 Leptomeningeal Carcinomatosis," *Cancer Res.* 52:6168–6174 (1992).

Plautz et al., "Selective Elimination of Recombinant Genes in Vivo With a Suicide Retroviral Vector," *New Biologist* 3(7):709–715 (1991).

Plowchalk, D.R. and Mattison, D.R., "Phosphoramide Mustard Is Responsible for the Ovarian Toxicity of Cyclophosphamide," *Toxicol. Appl. Pharmacol.* 107:472–481 (1991).

Preiss et al., "Molecular Genetics of Krüppel, a Gene Required for Segmentation of the Drosophila Embryo," *Nature* 313:27–32 (1985).

Price et al., "Lineage Analysis in the Vertebrate Nervous System by Retrovirus–Mediated Gene Transfer," *PNAS USA* 84:156–160 (1987).

Ram et al., "In Situ Retroviral–mediated Gene Transfer for the Treatment of Brain Tumors in Rats," *Cancer Res.* 53:83–88 (1993).

Raney et al, "Characterization of Hepatitis B Virus Major Surface Antigen Gene Transcriptional Regulatory Elements in Differentiated Hepatoma Cell Lines," *J. Virol.* 63(9):3919–3925 (1989).

Reik et al., "Replication–competent Moloney murine leukemia virus carrying a bacterial suppressor tRNA gene: Selective cloning of proviral and flanking host sequences," *PNAS USA* 82:1141–1145 (1985).

Roenigk, H.H. and Deodhar, S., "Immunotherapy of Malignant Melanoma With Vaccinia Virus," *Arch. Dermatol.* 109:668–673 (1974).

Rosenberg, S.A., "Immunotherapy and Gene Therapy of Cancer," *Cancer Res. (Suppl.)* 51:5074s–5079s (1991).

Rosenberg et al., "Grafting Genetically Modified Cells to the Damaged Brain: Restorative Effects of NGF Expression," *Science* 242:1575–1578 (1988).

Rosenberg et al., "Production of Phenocopies by Krüppel Antisense RNA Injection into Drosophila Embryos," *Nature* 313:703–706 (1985).

Ryder et al., "Establishment and Characterization of Multipotent Neural Cell Lines Using Retrovirus Vector–Mediated Oncogene Transfer," *J. Neurobiol.* 21(2):356–375 (1990).

Salcman, M. and Samaras, G.M., "Interstitial Microwave Hyperthermia for Brain Tumors," *J. Neuro–Oncol.* 1:225–236 (1983).

Schuster et al., "Intraarterial Therapy of Human Glioma Xenografts in Athymic Mice Using 4–Hydroperoxycyclophosphamide," *Cancer Res.* 53:2338–2343 (1993).

Schuster et al., "Intra–arterial therapy of Human glioma xenografts in athymic rats using 4–hydroperoxycyclophosphamide," *Proc. Amer. Assoc. Cancer Res.* 34:269 Abstract No. 1599 (1993).

Sealy et al., "Interstitial Misonidazole—A Preliminary Report on a New Perspective in Clinical Radiation Sensitization and Hypoxic Cell Chemotherapy," *Cancer* 54:1535–1540 (1984).

Sharpe et al., "Role of Abortive Retroviral Infection of Neurons in Spongiform CNS Degeneration," *Nature* 346:181–183 (1990).

Shih et al. "Herpes Simplex Virus as a Vector for Eukaryotic Viral Genes," *Vaccines* 85:177–180 (1985).

Shimohama et al., "Grafting Genetically Modified Cells into the Rat Brain: Characteristics of *E. coli* β–Galactosidase as a Reporter Gene," *Molec. Brain Res.* 5:271–278 (1989).

Short et al., "Autocrine Differentiation of PC12 Cells Mediated by Retroviral Vectors," *Dev. Neurosci.* 12:34–45 (1990).

Short et al., "Direct Infection of Rat C6 Glioma Cells in the Brain by Grafting of a Retrovirus Packaging Line," *Soc. for Neurosci. Abstr.* 16:449 Part 1, Abstract 189.2 (1990).

Short et al., "Gene Delivery to Glioma Cells in Rat Brain by Grafting of a Retrovirus Packaging Cell Line," *J. Neurosci. Res.* 27:427–439 (1990).

Sladek, N.E., "Metabolism of Oxazaphosphorines," *Pharmacol. Ther.* 37:301–355 (1988).

Sladek, N.E., "Oxazaphosphorines," in: Metabolism and Action of Anticancer Drugs, Powis et al., eds., Taylor and Francis, NY, NY, pp. 48–90 (1987).

Smee et al., "Anti–Herpesvirus Activity of the Acyclic Nucleoside 9–(1, 3–Dihydroxy–2–Propoxymethyl)Guanine," *Antimicrob. Agents Chemother.* 23(5):676–682 (1980).

Smiley, James R., "Construction In Vitro and Rescue of a Thymidine Kinase–Deficient Deletion Mutation of Herpes Simplex Virus," *Nature* 285:333–335 (1980).

Smith et al., "A New Nucleoside Analog, 9–[[2–Hydroxy–1–(Hydroxymethyl)Ethoxy]Methyl]Guanine, Highly Active In Vitro Against Herpes Simplex Virus Types 1 and 2," *Antimicrob. Agents Chemother.* 22(1):55–61 (1982).

Snyder et al., "Multipotent Neural Cell Lines, Generated via Retroviral–mediated Gene Transfer, Integrate In Vivo Following Transplantation into Developing Mouse Cerebellum (CB)," *Soc. Neurosci. Abstracts* 15:13 Abstract No. 9.9 (1989).

Snyderman et al. "Cisplatin Sensitization to Radiotherapy in Stage IV Squamous Cell Carcinoma of the Head and Neck," *Arch. Otolaryngol. Head Neck Surg.* 112:1147–1150 (1986).

Soule, H.D. and McGrath, C.M., "Estrogen Responsive Proliferation of Clonal Human Breast Carcinoma Cells in Athymic Mice," *Cancer Lett.* 10:177–189 (1980).

Soule et al., "A Human Cell Line From a Pleural Effusion Derived From a Breast Carcinoma," *J. Natl. Cancer Inst.* 51(5):1409–1416 (1973).

Takamiya et al., "An Experimental Model of Retrovirus Gene Therapy for Malignant Brain Tumors," *J. Neurosurg.* 79:104–110 (1993).

Takamiya et al., "Gene Therapy of Malignant Brain Tumors: A Rat Glioma Line Bearing the Herpes Simplex Virus Type 1–Thymidine Kinase Gene and Wild–Type Retrovirus Kills Other Tumor Cells," *J. Nurosci. Res.* 33:493–503 (1992).

Takle et al., "Cloning and Expression of a Trypomastigote–Specific 85 Kilodalton Surface Antigen Gene from *Trypanosoma cruzi*," *Molec. Biochem. Parasitol.* 37:57–64 (1989).

Tamargo et al., "Interstitial Chemotherapy of the 9L Gliosarcoma: Controlled Release Polymers for Drug Delivery in the Brain," *Cancer Res.* 53:329–333 (1993).

Thompson, R.L. and Stevens, J.G., "Biological Characterization of a Herpes Simplex Virus Intertypic Recombinant which is Completely and Specifically Non–Neurovirulent," *Virology* 131:171–179 (1983).

Thompson et al., "Herpes Simplex Virus Neurovirulence and Productive Infection of Neural Cells Is Associated with a Function Which Maps between 0.82 and 0.832 Map Units on the HSV Genome," *Virology* 172:435–450 (1989).

Tondravi, M.M. "DNA Rearrangements Associated with the H3 Surface Antigen Gene of *Tetrahymena thermophila* that Occur During Macronuclear Development," *Curr. Genet.* 14:617–626 (1988).

Trojan et al. "Treatment and Prevention of Rat Glioblastoma by Immunogenic C6 Cells Expressing Antisense Insulin–Like Growth Factor I RNA," *Science* 259:94–97 (1993).

Turner, D.L. and Cepko, C.L., "A Common Progenitor for Neurons and Glia Persists in Rat Retina Late in Development," *Nature* 328:131–136 (1987).

Walsh, C. and Cepko, C.L., "Clonally Related Cortical Cells Show Several Migration Patterns," *Science* 241:1342–1345 (1988).

Waxman, D.J., "Rat HeDatic Cytochrome P–450 Isoenzyme 2c," *J. Biol. Chem.* 259(24):15481–15490 (1984).

Waxman, D.J., "Rat Hepatic P450IIC Subfamily Expression Using Catalytic, Immunochemical, and Molecular Probes," *Meth. Enzymol.* 206:249–267 (1991).

Waxman D.J. and Walsh, C. "Cytochrome –450 Isozyme 1 from Phenobarbital–Induced Rat Liver: Purification, Characterization, and Interactions with Metyrapone and Cytochrome $b_5$," *Biochem.* 22:4846–4855 (1983).

Waxman, D.J. and Walsh, C., "Phenobarbital–induced Rat Liver Cytochrome P–450," *J. Biol. Chem.* 257(17):10446–10457 (1982).

Waxman et al., "Regioselectivity and Stereoselectivity of Androgen Hydroxylations Catalyzed by Cytochrome P–450 Isozymes Purified from Phenobarbital–induced Rat Liver," *J. Biol. Chem.* 258(19):11937–11947 (1983).

Weber, G.F. and Waxman, D.J., "Activation of the Anti––Cancer Drug Ifosphamide by Rat Liver Microsomal P450 Enzymes," *Biochem. Pharmacol.* 45(8):1685–1694 (1993).

Wei et al. "Experimental Tumor Therapy in Mice Using the Cyclophosphamide–Activating Cytochrome P450 2B1 Gene," *Hum. Gene Ther.* 5:969–978 (1994).

Welt et al., "Monoclonal Antibody to an Intracellular Antigen Images Human Melanoma Transplants in nu/nu Mice," *PNAS USA* 84:4200–4204 (1987).

West, S.C. and Howard–Flanders, P., "Duplex–Duplex Interactions Catalyzed by RecA Protein Allow Strand Exchanges to Pass Double–Strand Breaks in DNA," *Cell* 37:683–691 (1984).

Wolf et al., "Retrovirus–mediated Gene Transfer of Beta–nerve Growth Factor into Mouse Pituitary Line AtT–20," *Molec. Biol. Med.* 5:43–59 (1988).

Wolff et al., "Grafting Fibroblasts Genetically Modified to Produce L–Dopa in a Rat Model of Parkinson Disease," *PNAS USA* 86:9011–9014 (1989).

Wyllie, A.H., "Glucocorticoid–induced thymocyte apoptosis is associated with endogenous endonuclease activation," *Nature* 284:555–556 (1980).

Yamada et al., "Retrovirus–mediated Gene Transfer Targeted to Malignant Glioma Cells in Murine Brain," *Jpn. J. Cancer Res.* 83:1244–1247 (1992).

Yamano et al., "cDNA Cloning and Sequence and cDNA––Directed Expression of Human P450 IIBI: Identification of a Normal and Two Variant cDNAs Derived from the CYP2B Locus on Chromosome 19 and Differential Expression of the IIB mRNAs in Human Liver," *Biochem.* 28:7340–7348 (1989).

Yamano et al., "The CYP2A3 Gene Product Catalyzes Coumarin 7–Hydroxylation in Human Liver Microsomes," *Biochem.* 29:1322–1329 (1990).

Yoshii et al., "Estimation of Growth Fraction with Bromodeoxyuridine in Human Central Nervous System Tumors," *J. Neurosurg.* 65:659–663 (1986).

Yu et al., "Treatment of Glioma Engineered Interleukin 4–secreting Cells," *Cancer Res.* 53:3125–3128 (1993).

Zhou et al., "Timing and Patterns of Astrocyte Migration From Xenogeneic Transplants of the Cortex and Corpus Callosum," *J. Compar. Neurol.* 292:320–330 (1990).

METHOD OF SELECTIVELY DESTROYING NEOPLASTIC CELLS

CROSS-REFERENCES TO RELATED APPLICATIONS

This application is a continuation-in-part of U.S. patent application Ser. No. 08/291,500, filed Aug. 17, 1994 abandoned, the content of which is relied upon and incorporated by reference in its entirety.

STATEMENT AS TO RIGHTS TO INVENTIONS MADE UNDER FEDERALLY-SPONSORED RESEARCH AND DEVELOPMENT

The U.S. Government has a paid-up license in this invention and the right in limited circumstances to require the patent owner to license others on reasonable terms as provided for by the terms of grant numbers NS-24279 and CA-49248 awarded by the National Institutes of Health.

BACKGROUND OF THE INVENTION

1. Field of the Invention

The present invention relates to the destruction of neoplastic cells utilizing viral vectors. More particularly, the present invention relates to the destruction of neoplastic cells utilizing viral vectors carrying genes with a drug-conditional "killing" function.

2. Description of Related Art

Neoplasia is a process by which the normal controlling mechanisms that regulate cell growth and differentiation are impaired resulting in progressive growth. During neoplasia, there is a characteristic failure to control cell turnover and growth. This lack of control causes a tumor to grow progressively, enlarging and occupying spaces in vital areas of the body. If the tumor invades surrounding tissue and is transported to distant sites the tendency of this tumor will be to result in death of the individual.

One-third of all individuals in the United States will develop cancer (American Cancer Society Yearly Outlook for 1990). The five year survival rate for these patients has risen to nearly 50% as a result of progress and early diagnosis and therapy of the disease (American Cancer Society Yearly Outlook for 1990). However, cancer remains second only to cardiac disease as a cause of death in this country (American Cancer Society Yearly Outlook for 1990). Nearly 20% of all Americans who die this year will die of cancer (American Cancer Society Yearly Outlook for 1990). Half of these deaths will be due to the three most common types of cancer: lung, breast, and colon.

Recently there has been a rapid expansion of cancer treatments. Even though new treatments are being developed, the need still exists for improved methods for the treatment of most types of cancers.

The preferential killing of cancer cells without deleterious effect on normal cells is the desired goal in cancer therapy. In the past, this has been accomplished using a variety of procedures. These procedures include the administration of chemicals, chemotherapy, radiation, radiotherapy, and surgery.

Radiotherapy is a regional form of treatment used for the control of localized cancers (See Devita, V. T., in Harrison's *Principles of Internal Medicine*, Braunwald et al., eds., McGraw-Hill Inc., New York, 1987, pp. 431–446). Radiotherapy relies on the fact that some malignant diseases are more susceptible to damage by radiation. This difference in susceptibility depends on normal cells having a higher capacity for intercellular repair than neoplastic cells and the ability of normal organs to continue to function well if they are only segmentally damaged. If surrounding tissue can tolerate twice the radiation dose of a given tumor, then the tumor is radiosensitive. On the other hand, some tumors cannot be treated with radiotherapy. Cancer which extensively involves both lungs cannot be treated effectively with radiation therapy because of the greater radiosensitivity of the surrounding lung tissue (See Devita, V. T., in Harrison's *Principles of Internal Medicine*, Braunwald et al., eds., McGraw-Hill Inc., New York, 1987, pp. 431–446).

Surgery is still considered the primary treatment for most early cancers Id. However, most tumors are operable, but not fully resectable. Some tumors that appear resectable have micrometastatic disease outside the tumor field. This leads to a recurrence of the cancer close to the initial site of occurrence. Any cancer showing a level of metastasis effectively cannot be cured through surgery.

Other types of localized therapy (nonsystemic) have been explored. These include local hyperthermia (Salcman et al., *J. Neuro-Oncol.* 1:225–236 (1983)), photodynamic therapy (Cheng et al., *Surg. Neurol.* 25:423–435 (1986)), and interstitial radiation (Gutin et al., *J. Neurosurgery* 67:864–873 (1987)). To date these therapies have been met with limited success.

Radiotherapy and surgery offer ways of reducing the tumor mass in specific regions of the body that are accessible through surgical techniques or high doses of radiotherapy. Neither is applicable to the destruction of widely disseminated or circulating tumor cells characteristically present in most patients with cancer. This is the stimulus of the development of systemic treatments of cancer such as chemotherapy.

The use of cancer chemotherapeutic agents, even though widespread in use, has proved limitedly effective in treating most cancer types. Although some notable successes in the treatment of some specific tumor types (e.g., childhood leukemias) have been achieved with conventional chemotherapy, more limited success has been obtained in the treatment of solid tumors. This failure is primarily due to the low therapeutic index of many anti-cancer drugs, as well as the intrinsic or acquired drug resistance that often characterizes tumor cells. Another drawback to the use of cytotoxic agents for the treatment of cancer is their severe side effects. These include nausea, vomiting, CNS depression, localized pain, bone marrow depression, bleeding, renal damage, hypo and hyperglycemia, and hypersensitivity reactions. Another drawback is that they are only effective against rapidly dividing cells.

Organ-directed chemotherapy holds promise as a component of multimodal therapy to deliver drugs at higher concentrations for prolonged periods. However, at the present time, such continuous intravenous infusion of anti-cancer drugs has not shown any clear benefit.

A more modern approach to chemotherapy is to direct the toxic agents to the cancer cells themselves. This has been accomplished experimentally by linking the chemotherapeutic agent to either antibodies or toxic molecules that have a higher affinity for the tumor cells than for normal cells. These directed toxic bullets are still in an early clinical phase of development and are not commercially available.

Clearly, new approaches are needed to enhance the efficiency with which a chemotherapeutic agent can kill malignant tumor cells, while at the same time avoiding systemic toxicity.

Certain types of cancer, e.g., gliomas, which are the most common primary tumor arising in the human brain, defy the current modalities of treatment. Despite surgery, chemotherapy, and radiotherapy, glioblastoma multiforme, the most common of the gliomas, is almost universally fatal (Schoenberg, B. S., "The epidemiology of nervous system tumors," in *Oncology of the Nervous System*, M. D. Walker, ed., Boston, Mass., Martinus Nijhoff (1983); Levin et al., "Neoplasms of the Central Nervous System," Chapter 46 in *Cancer: Principles and Practice of Oncology*, vol. 2, 3rd ed., De Vita et al., eds., Lippincott Press, Philadelphia (1989), pp. 1557–1611).

Gliomas represent nearly 40% of all primary brain tumors, with glioblastoma multiforme constituting the most malignant form (Schoenberg, B. S., "The epidemiology of nervous system tumors," in *Oncology of the Nervous System*, Walker, M. D., ed., Cold Spring Harbor Laboratory, Cold Spring Harbor, N.Y. (1983)). The five year survival rate for persons with this high grade type of astrocytoma is less than 5 percent given current treatment modalities of surgery, radiation therapy and/or chemotherapy (Mahaley et al., *Neurosurgery* 71: 826–836 (1989); Schoenberg, B. S., "The epidemiology of nervous system tumors," in *Oncology of the Nervous System*, Walker, M. D., ed., Cold Spring Harbor Laboratory, Cold Spring Harbor, N.Y. (1983); Kim et al., *J. Neurosurg.* 74:27–37 (1991), Daumas-Duport et al., *Cancer* 2:2152–2165 (1988)).

The resistance of glioblastomas to current chemotherapy may reflect the proliferative characteristics of this tumor type, which are in between lower grades of astrocytoma and other types of metastatic tumors in the central nervous system (CNS), (Nagashima and Hoshino, *Acta Neuropathol.* 66:12–17 (1985)). The bromodeoxyuridine labelling index, which measures the percentage of cells that are in S phase at any given moment, is 7.3% in glioblastoma tumors, which is 2 to 7 times higher than in lower grade astrocytomas, but less than in metastatic tumors (Nagashima and Hoshino, supra).

A related parameter that is useful for appreciating the relative resistance of glioblastomas to current therapeutic modalities is the growth fraction, or the relative proportion of cells proliferating in the tumor at any one time. The growth fraction in this tumor type is only 30%, with the remaining 70% of cells being in $G_o$, a resting phase (cells in $G_o$ may die or may re-enter the active cell cycle; Yoshii et al., *J. Neurosurg.* 65:659–663 (1986)), while the 30% of glioblastoma cells that are actively dividing contribute to the lethal progression of this tumor, the 70% that are quiescent are responsible for the resistance of these tumors to a number of chemotherapeutic agents that target actively proliferating cells.

Further, surgical modalities for glioblastomas are hampered by the lack of distinct boundaries between the tumor and the surrounding parenchyma, and by the migration of tumor cells in the white matter tracts extending out from the primary site (Burger et al., *J. Neurosurg.* 58:159–169 (1983)), which preclude their complete removal.

Radiation therapy has also had limited success due to the low growth fraction in these tumors as well as to the radiation sensitivity of adjacent normal tissue (Wowra et al., *Acta Neurochir. (Wien)* 99:104–108 (1989); Zamorano et al., *Acta Neurochir. Suppl. (Wien)* 46:90–93 (1989)).

New approaches are needed to treat brain tumors.

It has been proposed that genes with a drug-conditional "killing" function be employed for treating tumors. This is the subject matter of co-pending U.S. patent application Ser. No. 07/895,364, which is incorporated by reference herein in its entirety. Specifically, it has been proposed that expression of the herpes simplex virus (HSV) thymidine kinase (TK) gene in proliferating cells, renders the cells sensitive to the deoxynucleoside analog, ganciclovir (Moolten et at., *Cancer Res.* 46:5276–5281 (1986); Moolten et al., *Hum. Gene Ther.* 1:125–134 (1990); Moolten et al., *J. Natl. Cancer Inst.* 82:297–300 (1990); Short et al., *J. Neurosci. Res.* 27:427–433 (1990); Ezzedine et al., *New Biol.* 3:608–614 (1991); Freeman et al., *J. Cell. Biochem.* 16F:47 (1992); Culver et al., *Science* 256:1550–1552 (1992); Takamiya et al. *J. Neurosci. Res.* 33:493–503 (1992); Yamada et al., *Jpn. J. Cancer Res.* 83:1244–1247 (1992); Ram et al., *Cancer Res.* 53:83–88 (1993); Oldfield et al., *Hum. Gene Ther.* 4:39–69 (1993); Takamiya et al., *J. Neurosurg.* 79:104–110 (1993); Caruso et al., *Proc. Natl. Acad. Sci. USA* 90:7024–7028 (1993); Boviatsis et al., *Hum. Gene Ther.* 5:183–191 (1994); Chiocca et al., "Virus-Mediated Genetic Treatment of Rodent Gliomas," in *Gene Therapeutics*, Wolff, J. A., ed., Birkhauser Publishers, Boston, Mass. (1994), pp. 245–262). HSV-TK mediates the phosphorylation of ganciclovir, which is incorporated into DNA strands during DNA replication (S-phase) in the cell cycle, leading to chain termination and cell death (Elion, G. B., *J. Antimicr. Chemother.* 12, sup. B:9–17 (1983)).

However, although effective, the dependence of this type of gene therapy on DNA replication during drug exposure may potentially limit its therapeutic effectiveness. For instance, the majority of cells in human malignant brain tumors are in $G_o$ (resting phase) at any one time (Nagashima et al., *Acta Neuropathol.* 66:12–17 (1985); Yoshii et al., *J. Neurosurg.* 65:659–663 (1986)). Further, ganciclovir was originally introduced into the clinic for treatment of herpes virus infection (Smith et al., *Antimicrob. Agents Chemother.* 22:55–61 (1982); Smee et al., *Antimicrob. Agents Chemother.* 23:676–682 (1980)); therefore, there are few detailed biochemical or pharmacological studies on the application of ganciclovir in cancer treatment.

A second example of a gene with a drug-conditional "killing" function is the bacterial cytosine deaminase gene, which confers chemosensitivity to the relatively non-toxic 5-fluorouracil precursor 5-fluorocytosine (Mullen et al., *Proc. Natl. Acad. Sci. USA* 89:33–37 (1992); Huber et al., *Cancer Res.* 53:4619–4626 (1993); Mullen et al., *Cancer Res.* 54:1503–1506 (1994)). Although potentially useful for cancer gene therapy, 5-fluorocytosine is an antifungal drug (Bennett, J. E., "Antimicrobial Agents: Antifungal Agents," in *Goodman and Gilman's The Pharmacological Basis of Therapeutics*, Gilman, A. G. et al., eds., vol. 8, Pergamon Press, New York (1990), pp. 1165–1181). Thus, few detailed pharmacological studies have been reported on the application of this drug in cancer treatment.

Cyclophosphamide (CPA) and its isomeric analog ifosphamide (IFA) are mainstays of cancer chemotherapy for several types of tumor (Colvin, O. M., "Alkylating Agents and Platinum Compounds," in *Cancer Medicine*, Holland et al., eds., Lea and Febiger, Philadelphia, Pa. (1993), pp. 733–734). These therapeutically inactive prodrugs require bioactivation by liver-specific enzymes of the cytochrome P450 family. One of these enzymes, cytochrome P450 2B1, which is induced by phenobarbital, activates CPA and IFA with high efficiency (Clarke et al., *Cancer Res.* 49:2344–2350 (1989); Weber and Waxman, *Biochemical Pharmacology* 45:1685–1694 (1993)). CPA and IFA are hydroxylated by cytochrome P450 to yield the primary metabolites, 4-hydroxycyclophosphamide or 4-hydroxyifosfamide, respectively. These primary metabolites are unstable and spontaneously decompose into cytotoxic compounds: acrolein and phosphoramide (or ifosphoramide) mustard (Colvin et al., *Cancer Treat. Rep.* 65:89–95 (1981); Sladek, N. E., "Oxazaphosphorines," in *Metabolism and Action of Anticancer Drugs*, Powis et al., eds., Taylor and Francis, New York (1987), pp. 48–90). The latter causes interstrand cross-links in DNA regardless of cell-cycle phase. Maximum cytotoxicity is obtained during subsequent S and mitotic (M)-phases of the cell cycle due to strand breaks (Colvin, O. M., (1993), supra). The therapeutic efficacy of these oxazaphosphorine anti-cancer drugs is limited by host toxicity resulting from the systemic distribution of activated drug metabolites formed in the liver.

Unfortunately, cyclophosphamide is largely ineffective in treating tumors of the central nervous system (CNS) owing to the poor transport of the activated metabolites across the blood-brain barrier and into cells (Genka et al., *Cancer Chemother. Pharmacol.* 27:1–7 (1990)), and by very low levels of cytochrome P450 in brain and tumor cells (Hodgson et al., *Mol. Cell. Biochem.* 120:171–179 (1993)).

Even in many cases of non-CNS malignant tumors, wherein there is ready access to liver derived active drug metabolites, one cannot administer sufficiently high levels of drug to effectively kill the tumor, without causing systemic toxicity in the patient, and possibly death. New approaches to selectively enhance the sensitivity of the malignant tumor to the chemotherapeutic agent are needed.

Thus, in light of the foregoing, there exists a need for a therapeutic method that will enhance the sensitivity of a malignant tumor to a chemotherapeutic agent in order to selectively destroying tumor cells while sparing normal cells, and that can be utilized with chemotherapeutic agents whose action is not restricted to a specific phase of the cell cycle, or limited due to low levels of gene products that are required to activate the agent.

SUMMARY OF THE INVENTION

Accordingly, the present invention overcomes the disadvantages of the prior art by providing a method for selectively killing nervous system tumor cells, said method comprising: (a) infecting said tumor cells with a viral vector, said vector carrying a cytochrome P450 gene, wherein expression of the gene product renders said tumor cells sensitive to a chemotherapeutic agent independent of the cell cycle of said tumor cells; (b) contacting said tumor cells with said agent; and (c) selectively killing said tumor cells. In addition, the present invention provides a method for selectively destroying peripheral tumor cells, said method comprising: (a) infecting said tumor cells with a viral vector, said vector carrying a cytochrome P450 gene, wherein expression of the gene product renders said tumor cells sensitive to a chemotherapeutic agent independent of the cell cycle of said tumor cells; (b) contacting said tumor cells with said agent; and (c) selectively killing said tumor cells.

In addition, the present invention provides a method of enhancing the therapeutic effectiveness of a chemotherapeutic agent in treating malignant tumors, said method comprising: (a) infecting a malignant tumor with a viral vector carrying a cytochrome P450 gene; (b) contacting the tumor with a chemotherapeutic agent that will be activated to a cytotoxic metabolite upon exposure to the cytochrome P450 gene product; and (c) generating high levels of cytotoxic metabolites within the tumor itself sufficient to improve the therapeutic effectiveness of the chemotherapeutic agent.

The invention also provides a preferred embodiment of the foregoing methods wherein the cytochrome gene is P450 2B1, P450 2B6, P450 2A6, P450 2C6, P450 2C8, P450 2C9, P450 2C11, or P450 3A4, and the chemotherapeutic agent is cyclophosphamide or ifosphamide.

The invention also provides a particularly preferred embodiment of the foregoing methods wherein the cytochrome gene is P450 2B1 and the chemotherapeutic agent is cyclophosphamide.

Thus, the inventors have discovered that by introducing a cytochrome P450 gene into tumor cells, the cellular and anatomic location of the anticancer drug's enzymatic conversion to a therapeutically active compound will be effectively restricted to the tumor site, thereby enhancing the efficiency with which tumor cells are killed, while at the same time minimizing undesirable side-effects to normal cells.

It is to be understood that both the foregoing general description and the following detailed description are exemplary and explanatory and are intended to provide further explanation of the invention as claimed.

Figure 7:
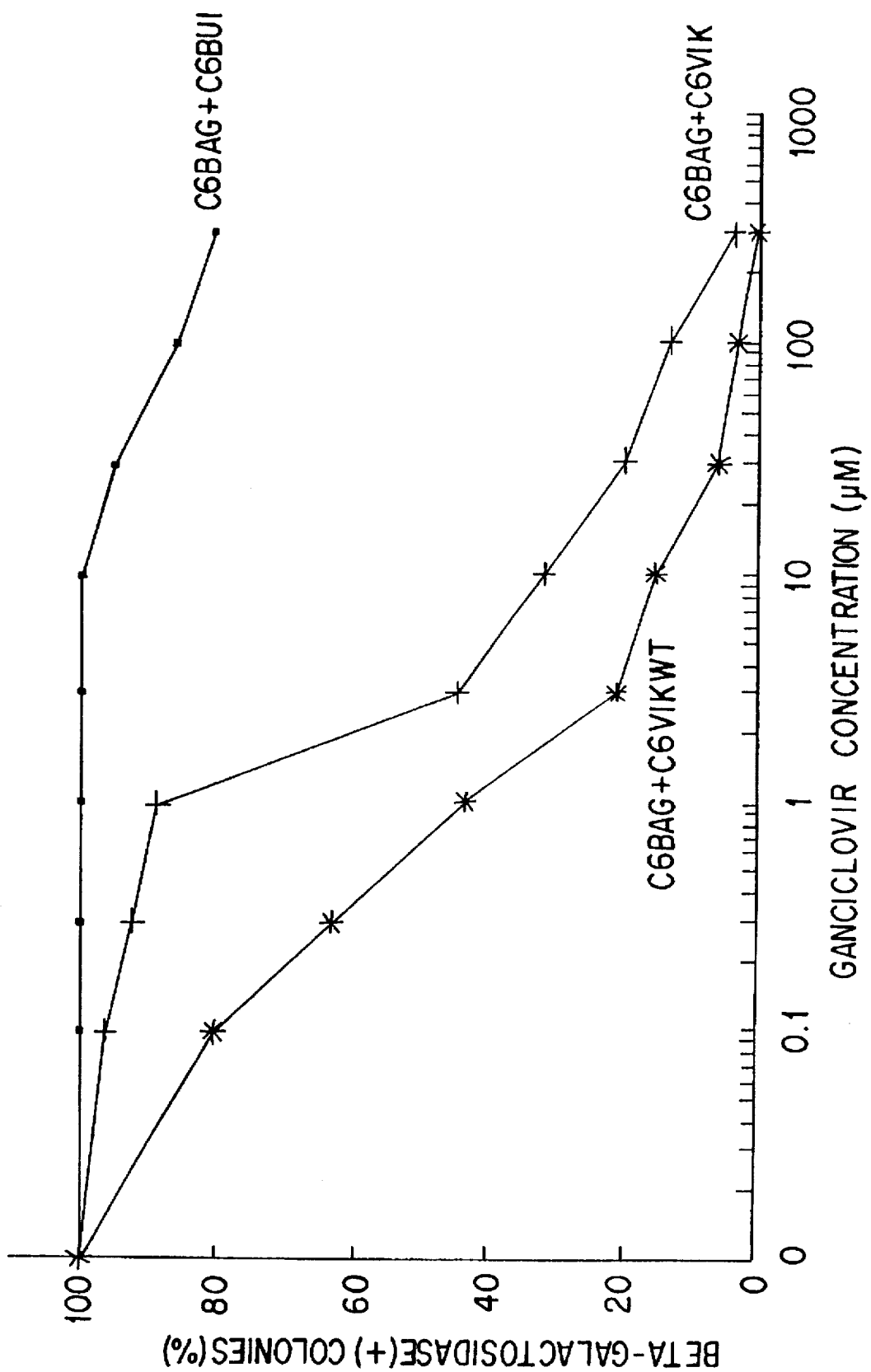
FIG. 7 is a graph depicting ganciclovir sensitivity of C6BAG cells after simultaneous co-culture with other C6-derived lines. Simultaneous co-culture experiments with C6BAG cells as recipients and C6VIK and C6VIKWT cells as donors (1:100) were carried out. Ganciclovir treatment was begun seven days after plating and continued for 14 days. Only beta-galactosidase positive colonies were counted (see FIGS. 5 and 6). Studies were done in triplicate with less than 0.5% variability.
Figure 8:
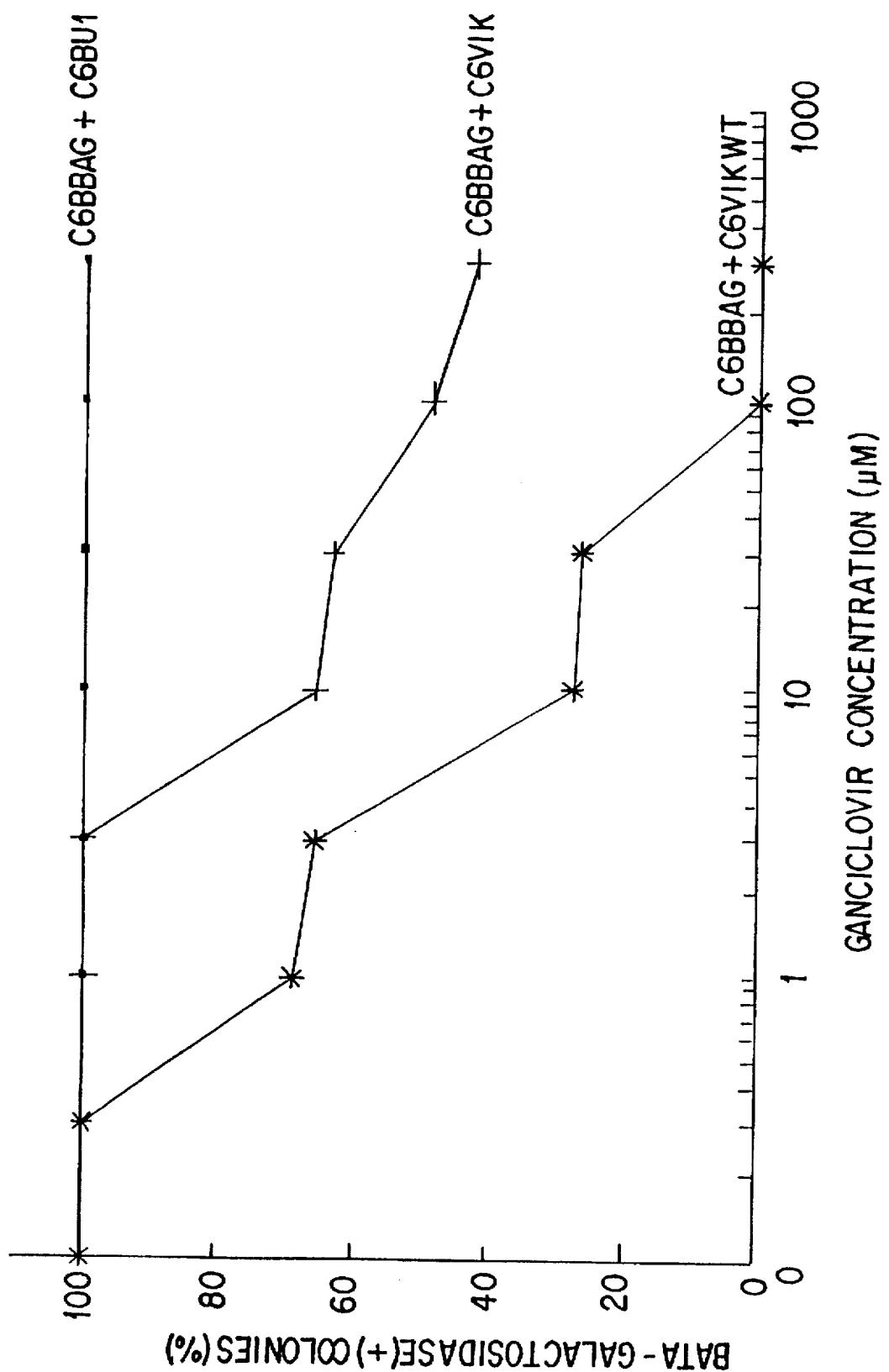

FIG. 8 is a graph depicting ganciclovir sensitivity of C6BAG cells after simultaneous co-culture with other C6-derived lines. Simultaneous co-culture experiments with C6BBAG cells were carried out as in FIG. 7. Studies were done in triplicate with less than 0.5% variability.

Figure 9:
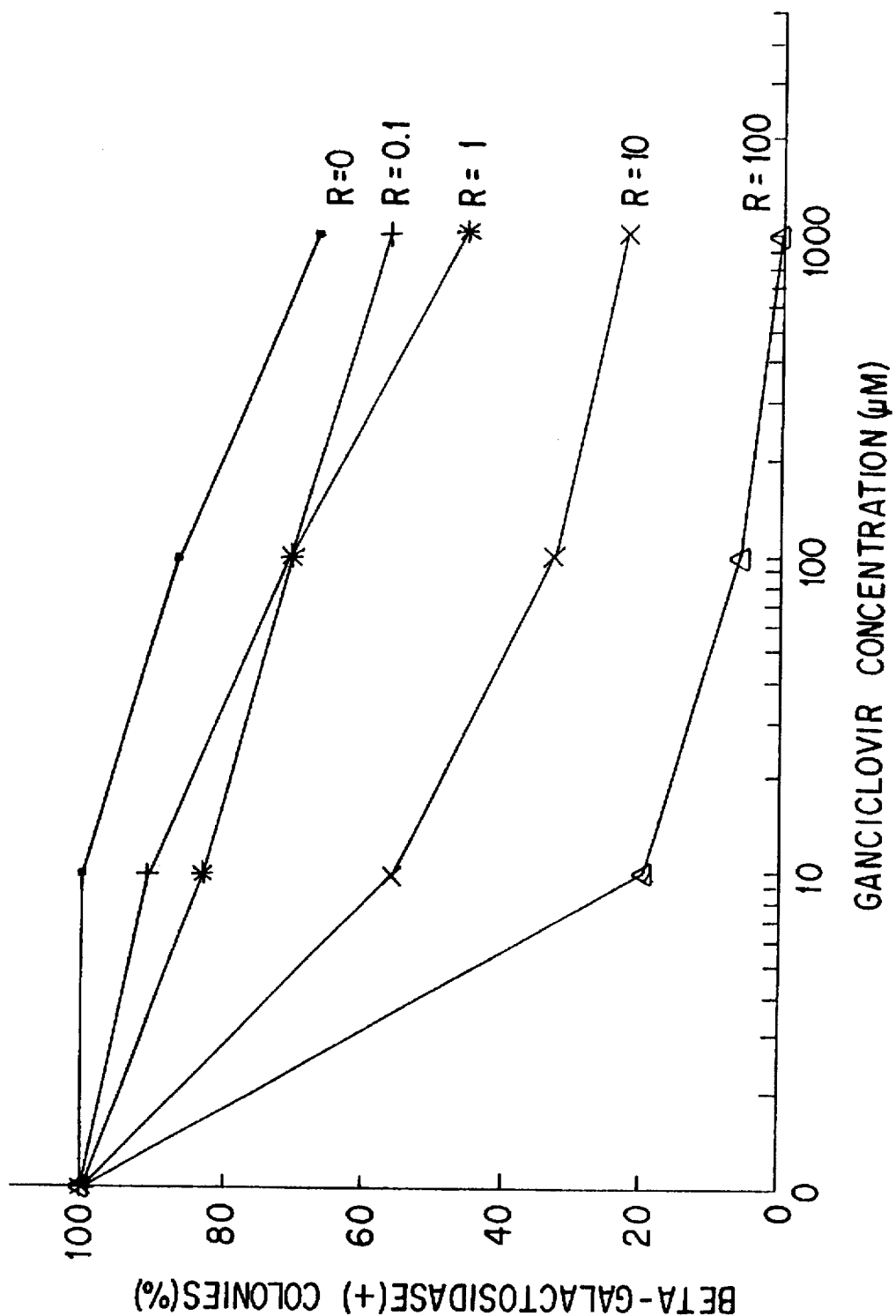

FIG. 9 is a graph depicting simultaneous co-culture experiments using varying ratios of donor C6VIKWT, to recipient cells C6BAG. Experiments were carried out as described in the legend to FIGS. 7 and 8. Studies were done in triplicate with less than 0.5% variability.

Figure 10:
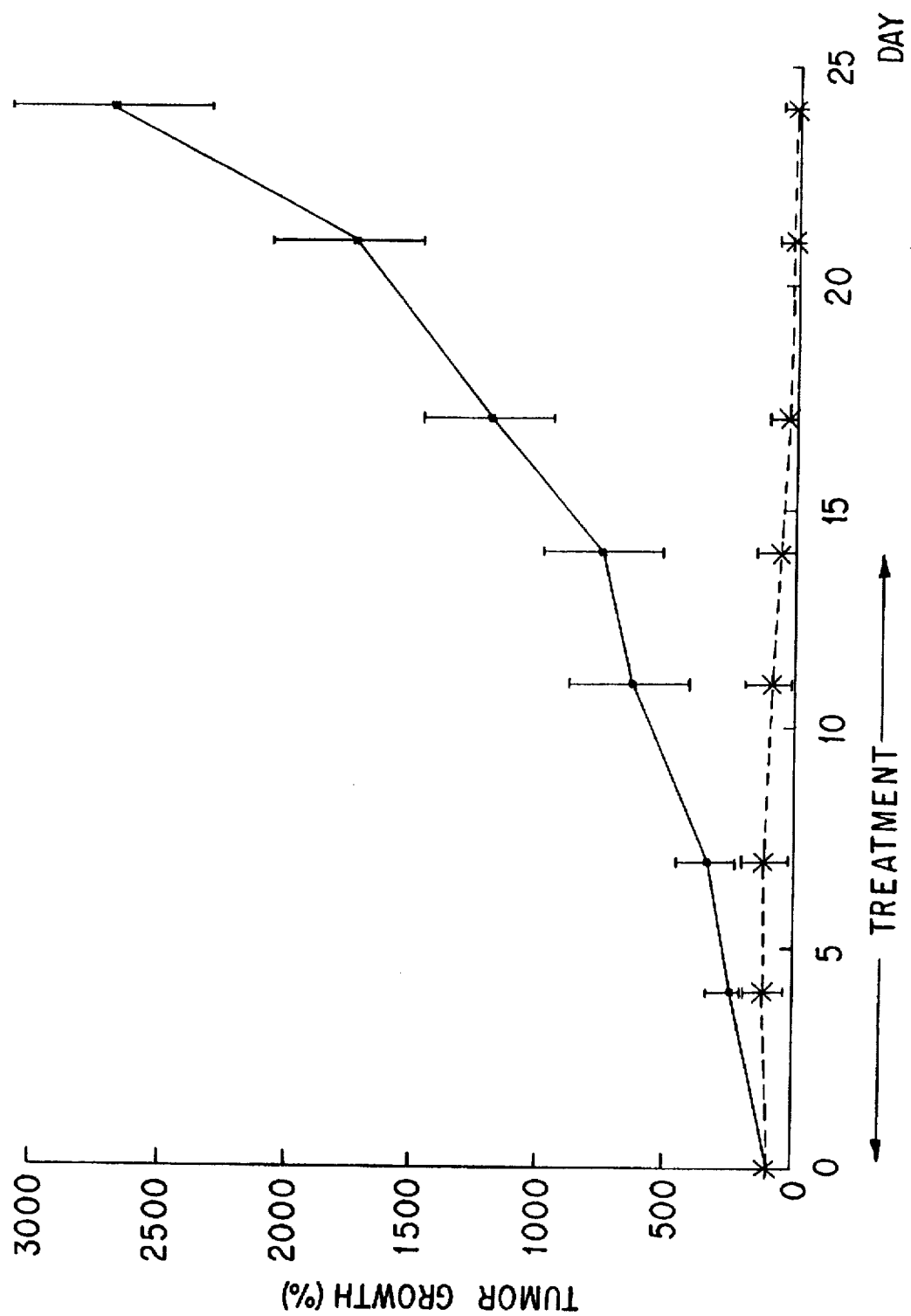

FIG. 10 is a graph depicting the growth of subcutaneous C6VIKWT tumors in nude mice. Treatment was begun after the tumor size had reached 1 cm in diameter (day 0) and continued for 14 days. The tumor growth rate (%) was calculated in comparison with the initial volume (100% at day 0). Tumors were treated with PBS (solid line) or with 50 mg/kg/day ganciclovir (dotted line). Bars indicate standard error of the mean.

Figure 11:
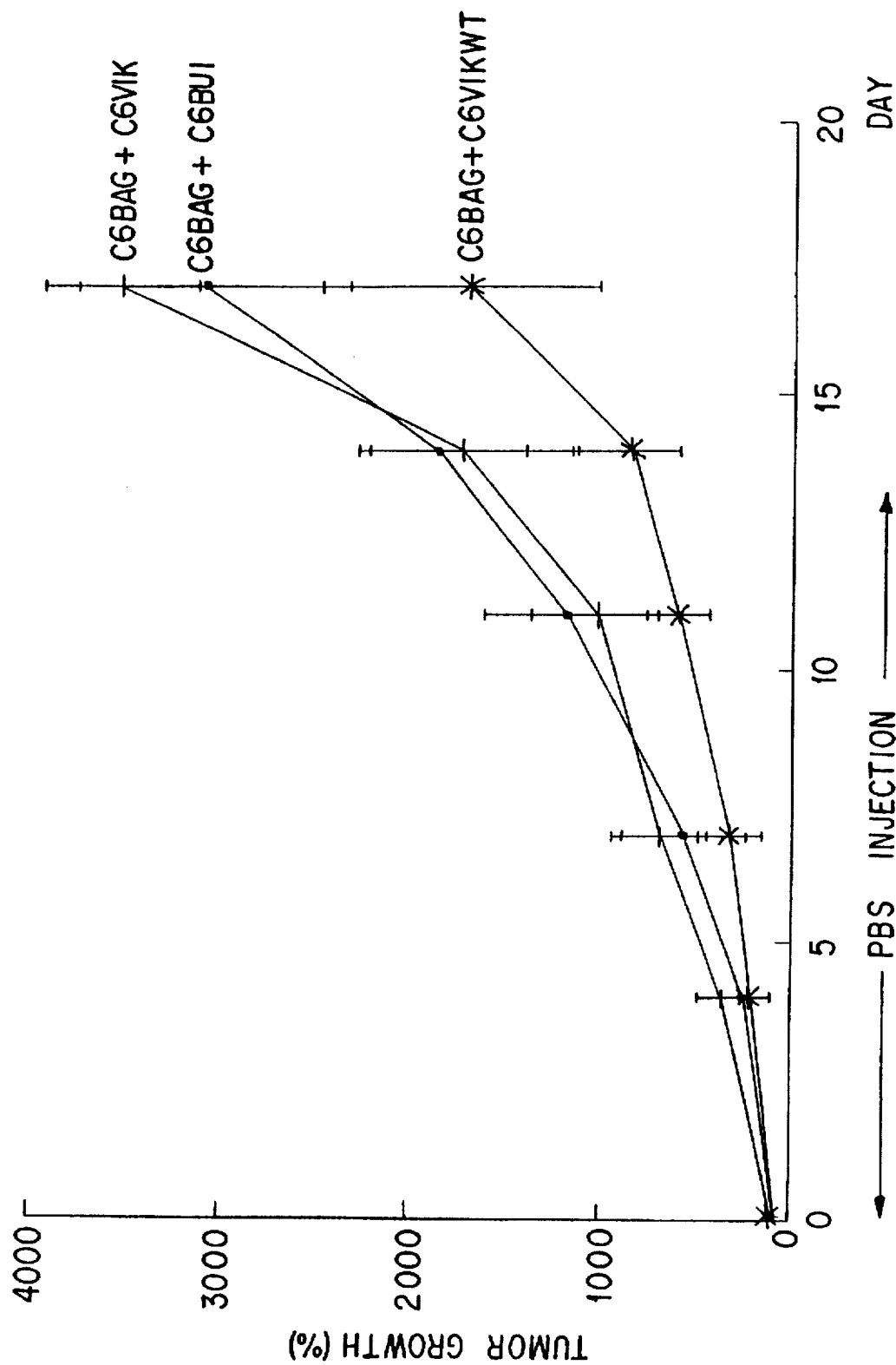

FIG. 11 is a graph depicting the growth of combinations of tumor cells in nude mice. Tumor cells were inoculated simultaneously in different combinations in a ratio of 1 to 10 (recipient (C6BAG) versus donors C6BU1 (n=9), C6VIK (n=9) or C6VIKWT, (n=7)). After tumors reached 1 cm in diameter, animals were treated with PBS for 14 days and then maintained without treatment for an additional 4 days. Bars indicate standard error of the mean.

Figure 12:
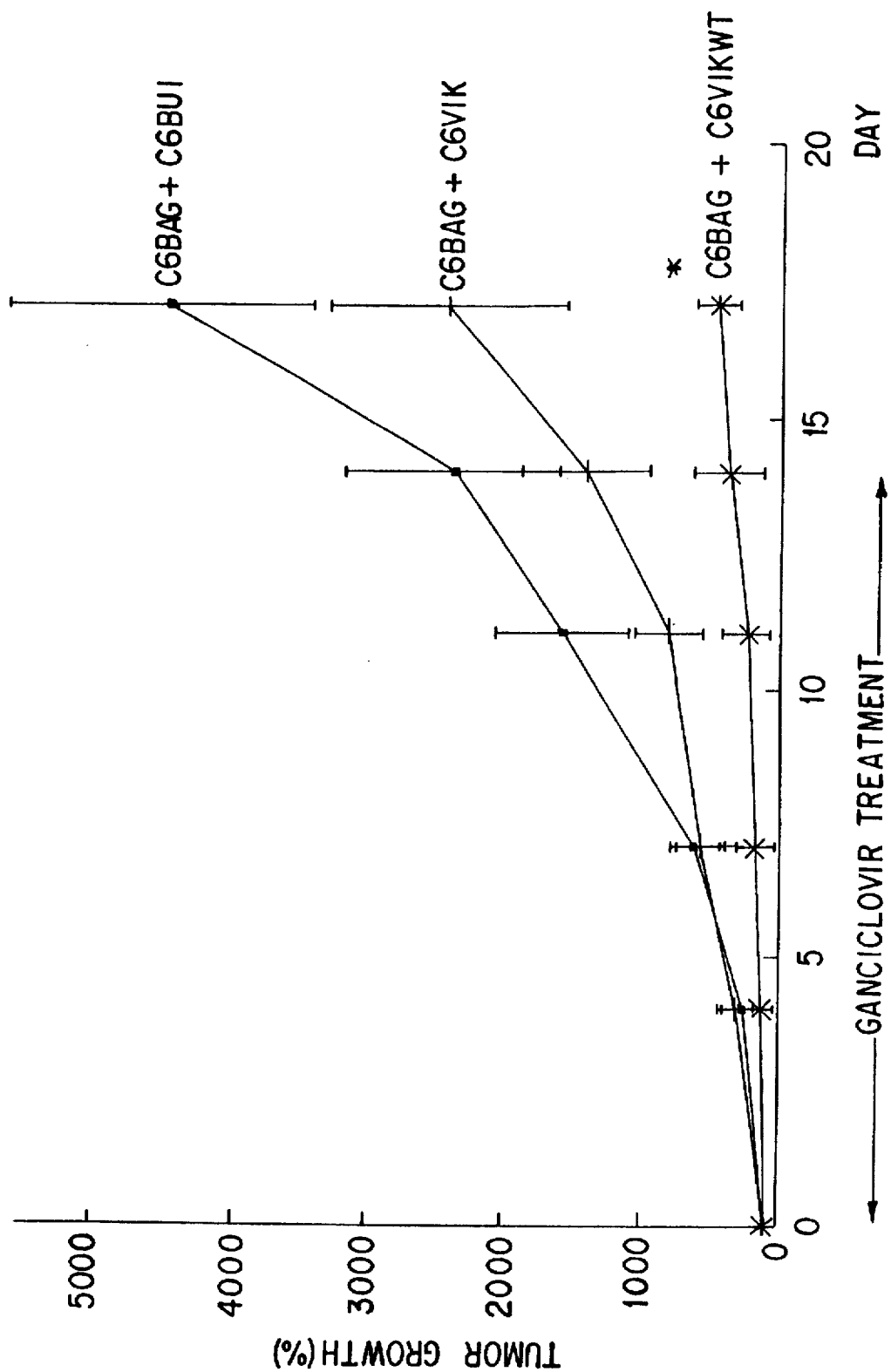

FIG. 12 is a graph depicting the growth of combinations of tumor cells in nude mice. The same combinations of cells as in FIG. 11 were treated in parallel with 50 mg/kg/day ganciclovir for 14 days. *=p<0.01. Bars indicate standard error of the mean.

Figure 13:
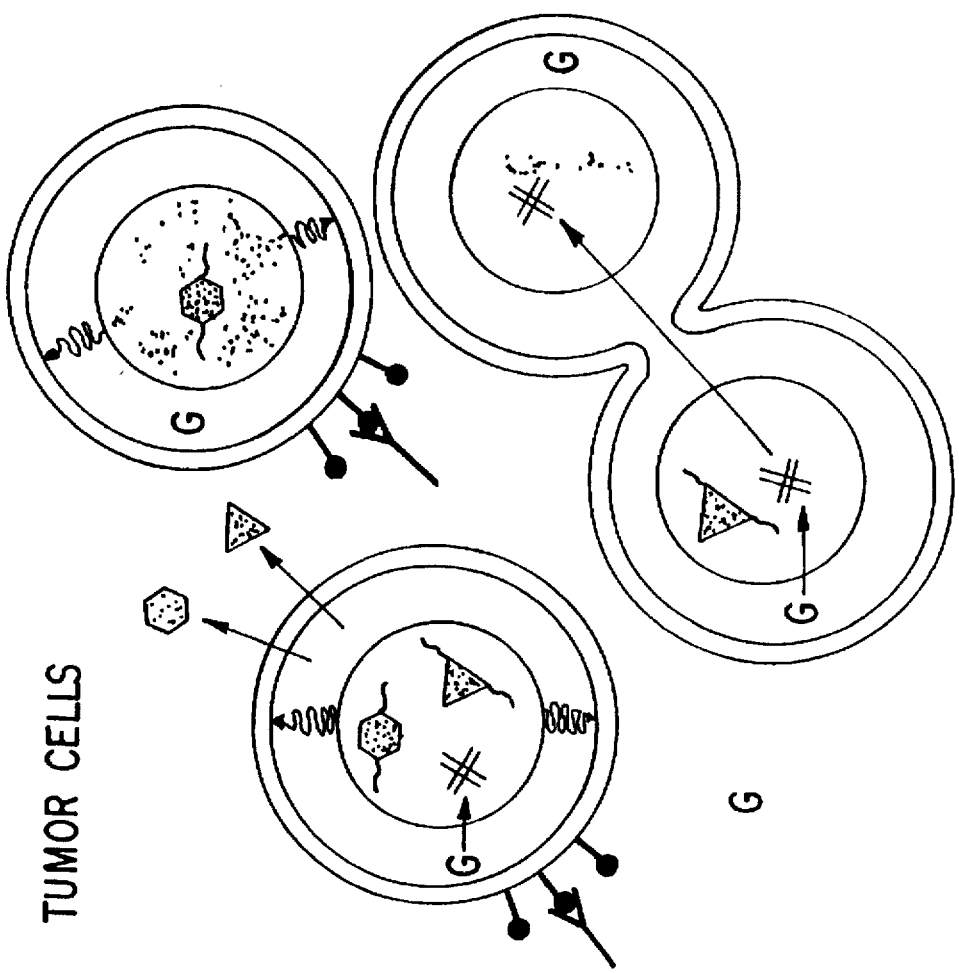
Figure 13:
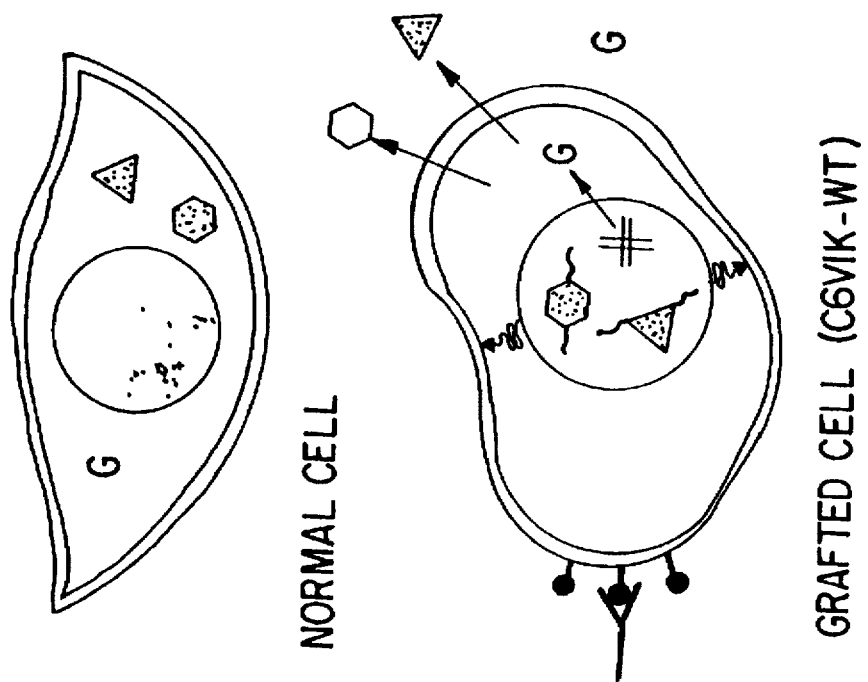

FIG. 13 is a schematic representation depicting the effects of C6VIKWT on tumor cells. In the adult brain, most normal cells are not dividing and thus are resistant to integration of retroviruses and toxic ganciclovir metabolites. Toxic effects of grafted C6VIKWT cells on dividing tumor cells may include: 1) debilitating effects (~>) of replicative infection of wild type MoMLV (hexagon); 2) expression of viral antigens on cells (↓)

which trigger rejection by host antibodies or other immune mechanisms (λ); 3) integration of retrovirus vector (Δ) bearing HSV-TK gene and conversion of ganciclovir (G) to a toxic metabolite (X) which kills cells undergoing DNA replication; and 4) transfer of X from infected tumor cells to uninfected tumor cells through cell contacts.

Figure 14:
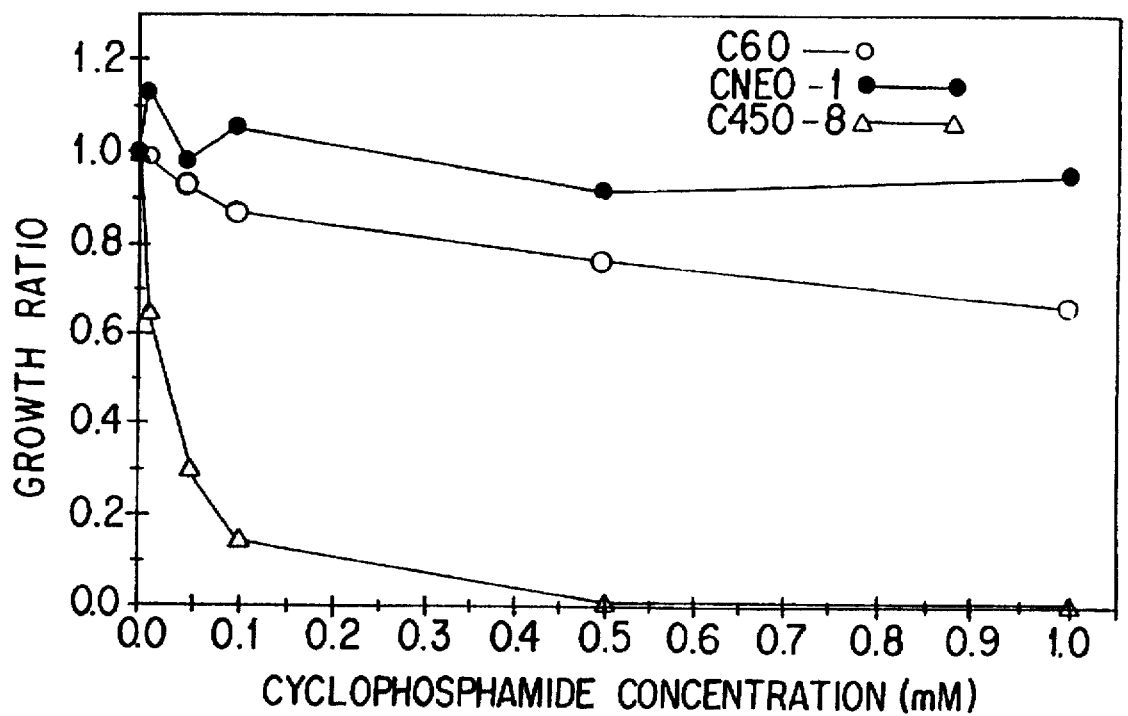

FIG. 14 is a graph depicting the acquisition of CPA sensitivity after transfection of the cytochrome P450 2B1 gene into rat C6 glioma cells.

The growth ratio is the number of cells that survived at a defined CPA concentration divided by the number of cells that survived without CPA for each cell line.

Figure 15A:
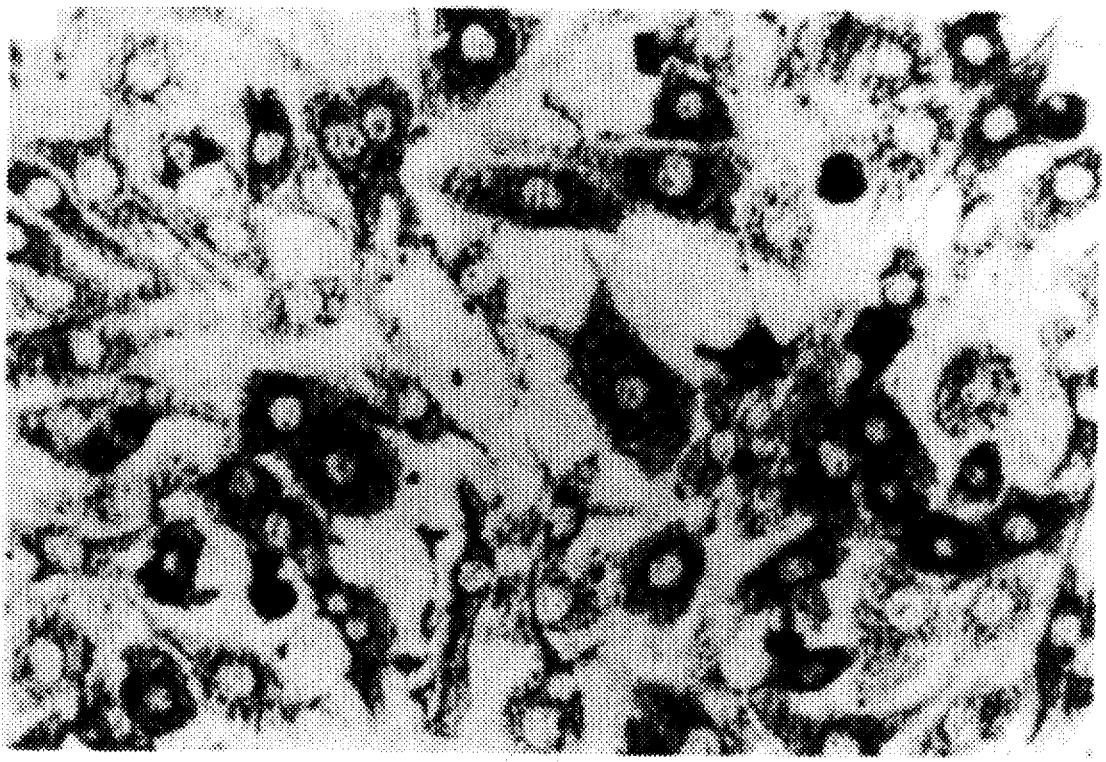

FIG. 15 is a photograph of an immunocytochemical analysis of cytochrome P450 2B1 enzyme in CPA-susceptible C450-8 and in CPA-insensitive C6, CNEO-1, and C450-19.

Figure 15B:
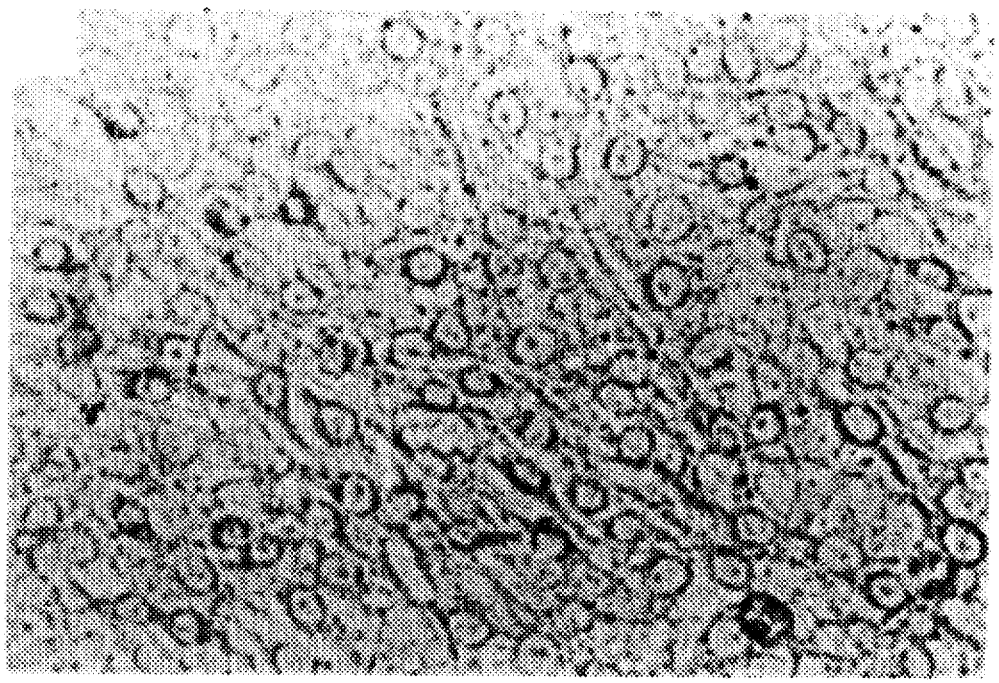

Immunoreactive protein appears as a black precipitate in a lacelike pattern in C450-8 cells (FIG. 15a), whereas no staining is present in CNEO-1 cells (FIG. 15b).

Figure 16:
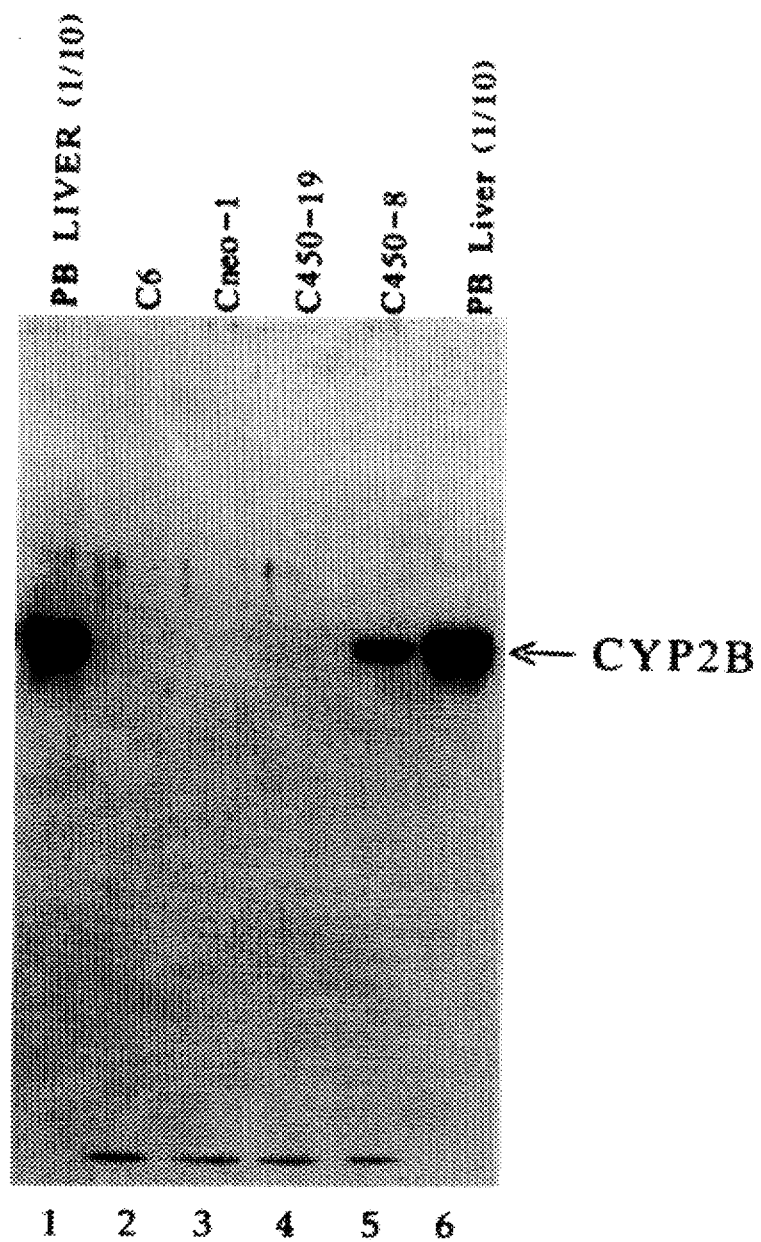

FIG. 16 is a western blot analysis of microsomal fractions (20 μg protein/lane) from C450-8 cells. The western blot confirms the presence of a single immunoreactive species (lane 5), corresponding to cytochrome P450 2B1 (designated by cytochrome P450 2B1). Liver microsomes isolated from phenobarbital-induced rat liver (PB liver, 2 μg protein/lane) are included as a positive control in lanes 1 and 6. Microsomal fractions from C6 (lane 2), CNEO-1 (lane 3), and C450-19 cells (lane 4) were included as negative controls.

Figure 17A:
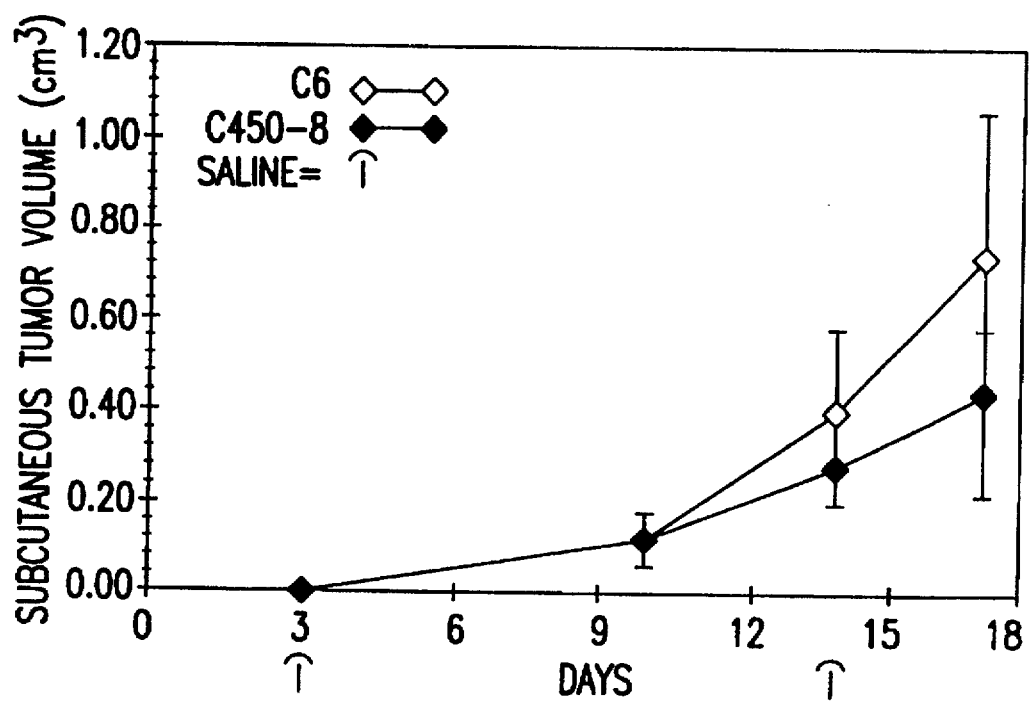

FIG. 17 is a graph depicting the subcutaneous growth of C6 and C450-8 tumors in nude mice with and without CPA therapy.

Figure 17B:
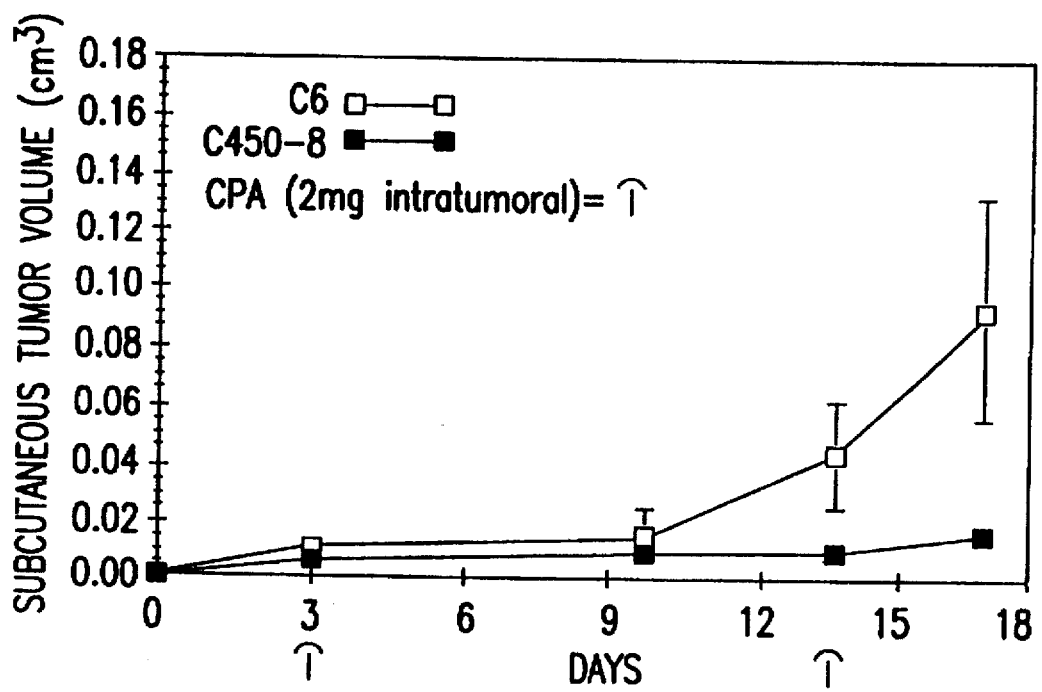

C6 or C450-8 cells ($10^6$ cells in 200 μl) were injected subcutaneously into the flanks of nude mice. Tumors (5 animals per group) were injected on day 3 and 14 with saline (FIG. 17A) or CPA (FIG. 17B). The average tumor volume and standard deviation are shown for each group. Note the Y-axis scale difference between Figures A and B.

FIG. 18 is a photograph depicting meningeal neoplasia of C6 gliomas in mouse brains injected with retrovirus producer fibroblasts and CPA.

Figure 18A:
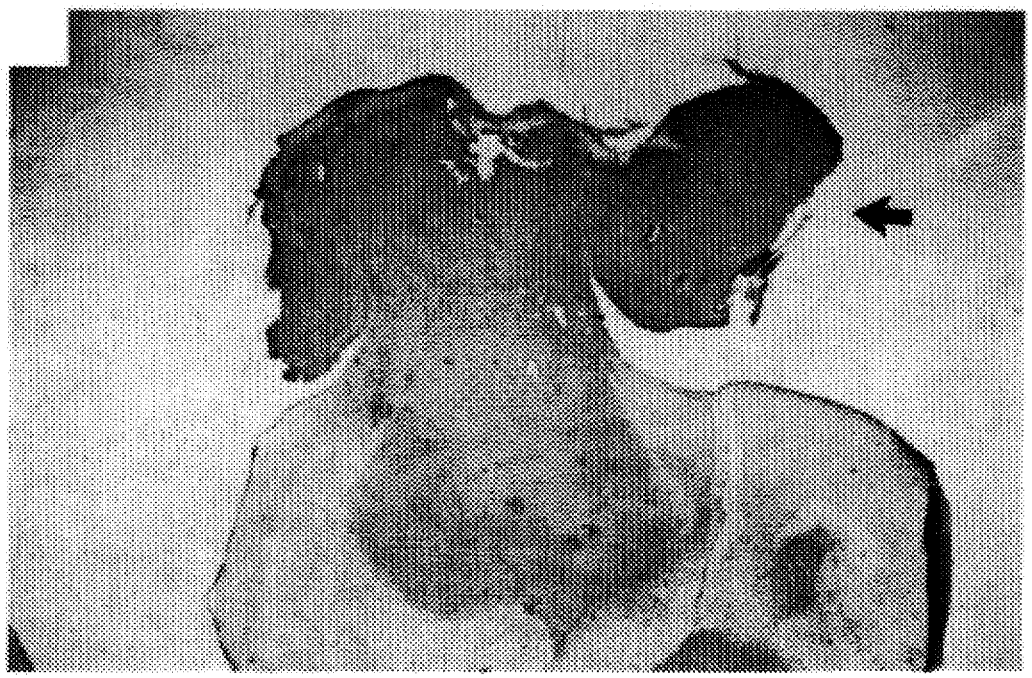
Figure 18B:
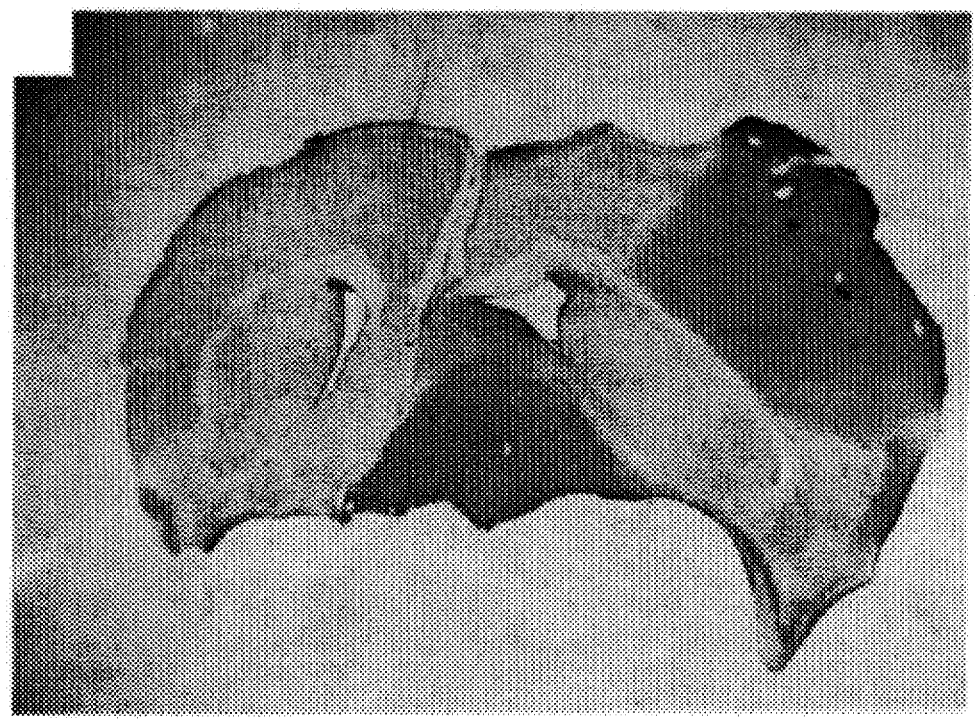

FIG. 18a shows a histopathologic coronal section from the brain of a control nude mouse that had been seeded with rat C6 glioma cells and then treated by stereotactic injection of lacZ-expressing murine cells (CRELacZ) into the brain and meningeal spaces followed by intratumoral administration of CPA. The extensive infiltration of tumor tissue into the meninges is marked by the dark arrow. FIG. 18b shows a histopathologic coronal section from the brain of a nude mouse that had been seeded with rat C6 glioma cells and was then treated by stereotactic injection of cytochrome P450 2B1-expressing murine cells (R450-2) into the brain and meningeal spaces followed by intratumoral administration of CPA.

FIG. 19 is a photomicrograph depicting parenchymal brain tumors from animals grafted with CRELacZ or R450-2 cells with subsequent intrathecal/intratumoral administration of CPA.

Figure 19A:
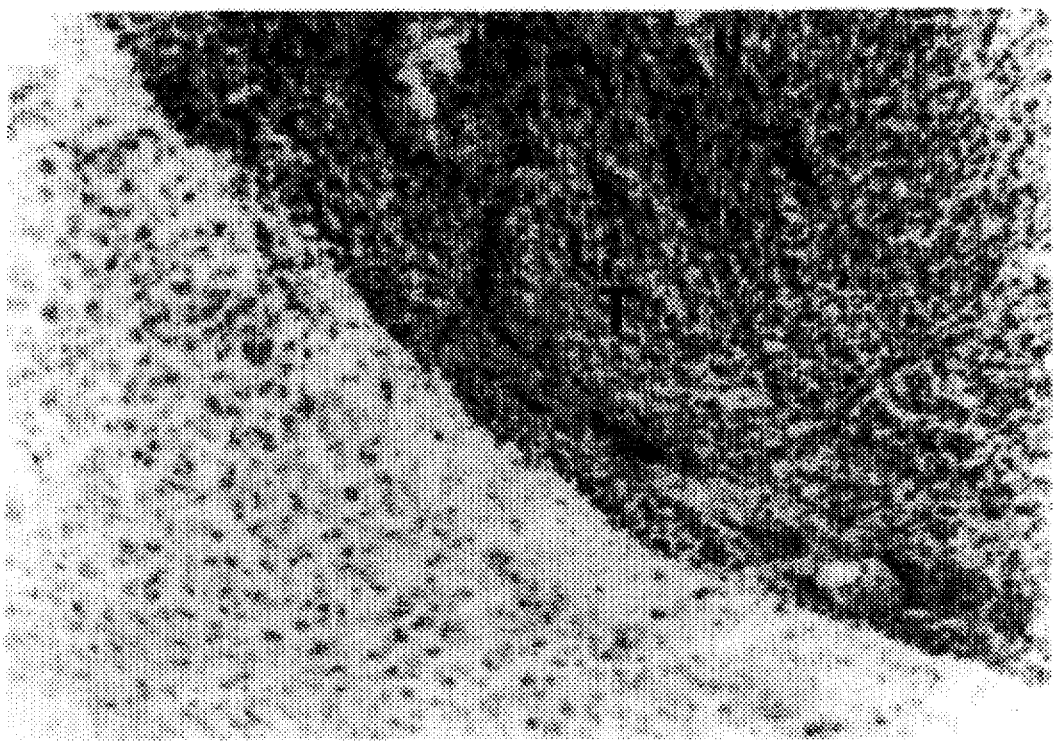
Figure 19B:
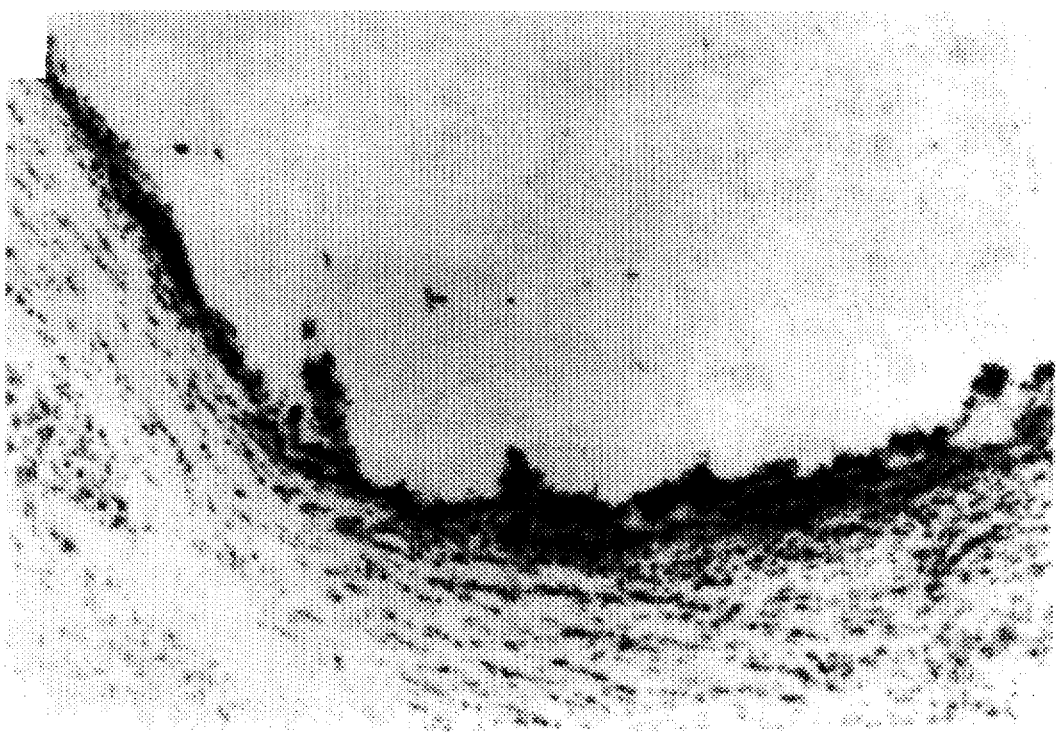

FIG. 19a shows a coronal section from the brain tumor of a mouse treated with CRE-LacZ cells and then CPA. This particular section shows the margin between normal brain on the left side of the photomicrograph and tumor (T) on the right side. FIG. 19b shows a coronal section from the brain tumor of a mouse treated with R450-2 cells and then CPA. This particular section shows the margin between normal brain on the left side of the photomicrograph and the cavity on the right, that originally contained necrotic tumor tissue which could not be mounted due to its friability. Some necrotic tumor cells (exhibiting extensive nuclear fragmentation) are still visible adjacent to normal brain. Magnification is 100×.

Figure 20A:
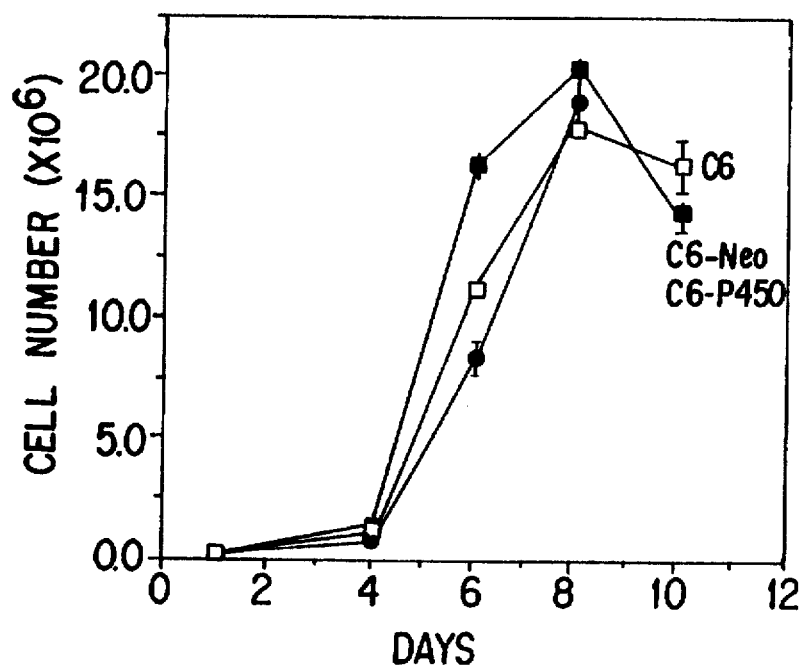
Figure 20B:
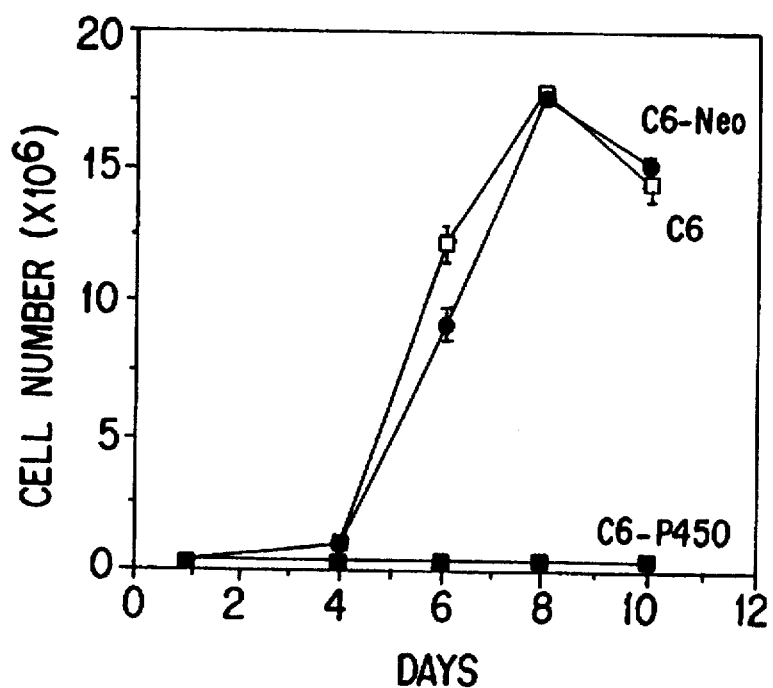

FIG. 20 is a graph depicting cell proliferation assays of C6, C6-Neo, and C6-P450. In FIG. 20A, the proliferation rate of C6, C6-Neo, and C6-P450 cells is shown in the absence of CPA over a 10-day course. In FIG. 20B, the same experiment was performed in the presence of CPA (0.5 mM). Open squares: C6-P450 cells; Squares with central dots: C6 cells; Filled triangles: C6-Neo cells. $2 \times 10^5$ C6 or C450-8 cells were plated onto a 10 cm dish in triplicate. The next day, 0.5 mM CPA or medium was added to all dishes. At each time indicated, cells were trypsinized and counted. The average cell number was given (mean±SEM).

Figure 21A:
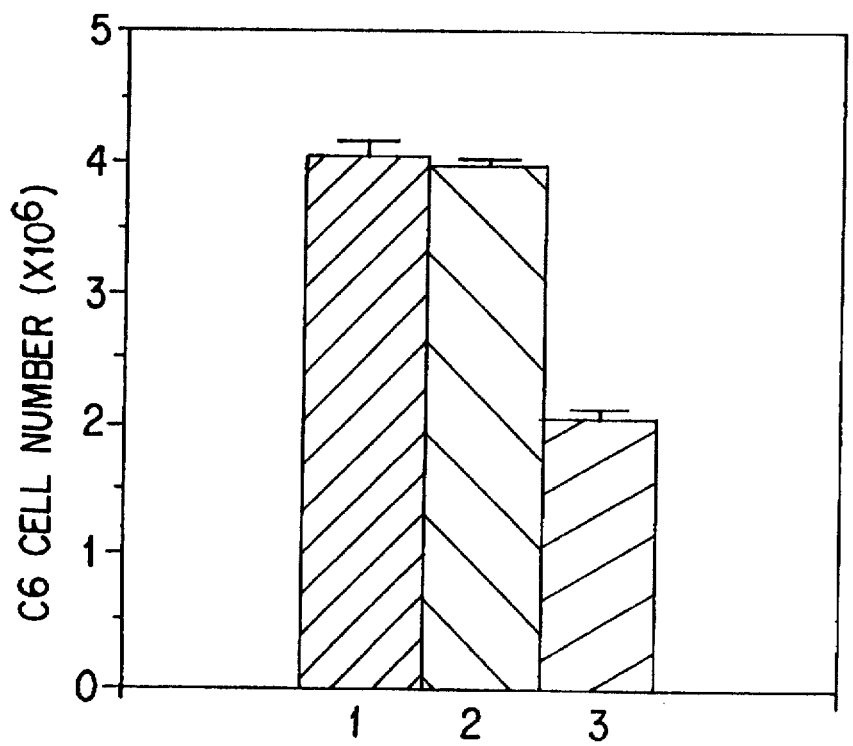
Figure 21B:
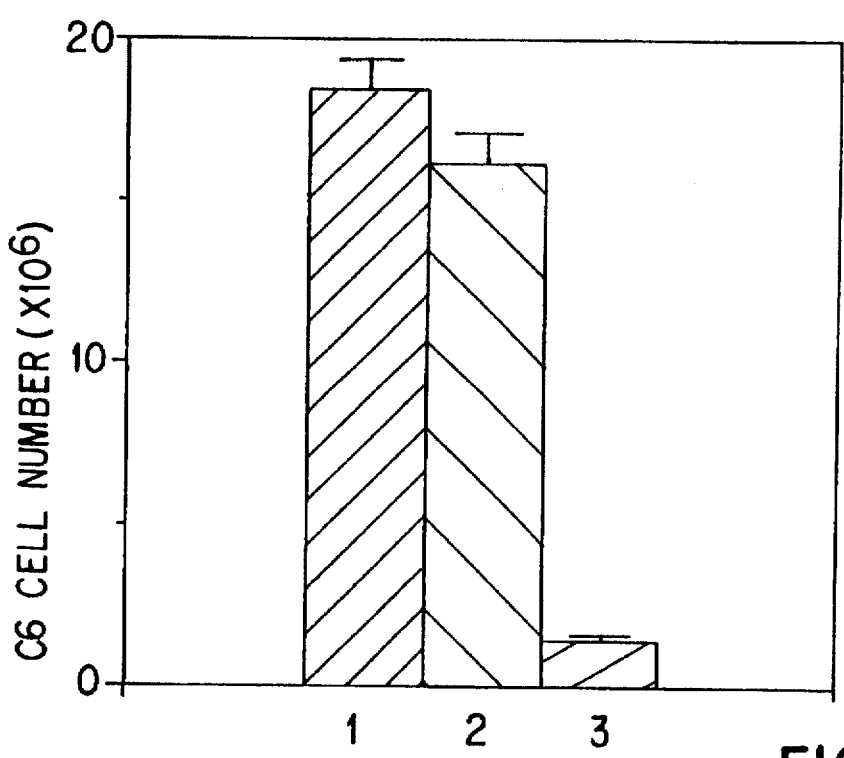

FIG. 21 is a bar graph depicting the secretory effect. In FIG. 21A, C6 ($3.5 \times 10^5$ cells) were co-cultured with C6 ($3.5 \times 10^5$ cells; column 1), C6-Neo ($3.5 \times 10^5$ cells; column 2), or C6-P450 ($3.5 \times 10^5$ cells; column 3) on a dish separated by a 0.45μ filter ("insert" system by FALCON) in the presence of 0.5 mM CPA. Five days later the number of C6 cells was determined by Coulter counting. In FIG. 21B, the surviving C6 cells from the previous experiment were trypsinized and replated at a density of $2\times10^5$ cells per dish. C6 cell numbers were then counted nine days later.

Figure 22A:
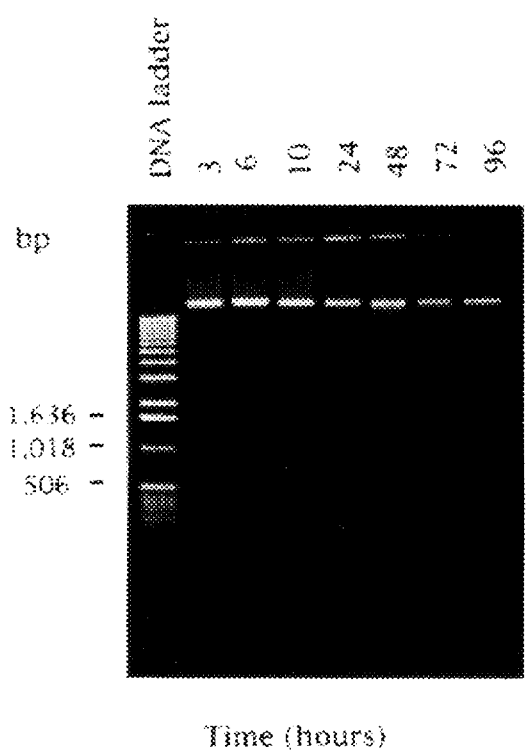
Figure 22B:
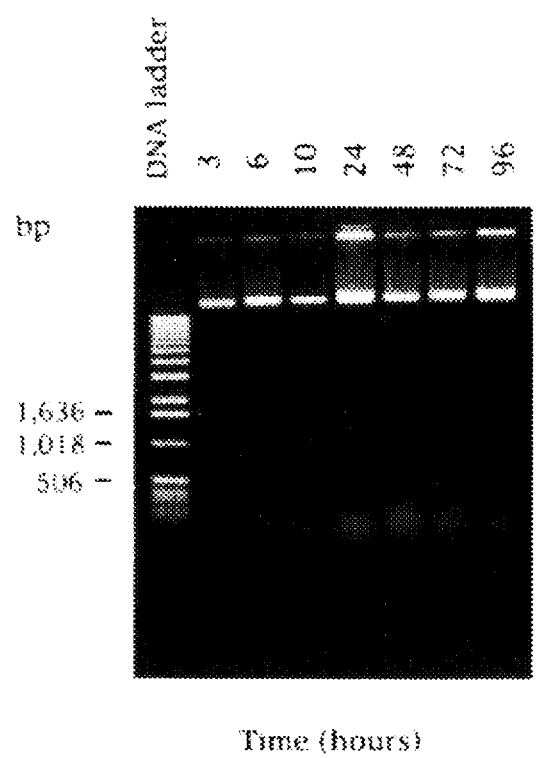

FIG. 22 is a photograph of a 1% agarose electrophoresis gel depicting nucleosomal laddering of C6-P450 cells treated with CPA. Genomic DNA (1 µg) from C6-P450 (FIG. 22A) or C6 (FIG. 22B) cells exposed to CPA was purified at the indicated times and isolated on a 1% agarose gel by electrophoresis.

Figure 23A:
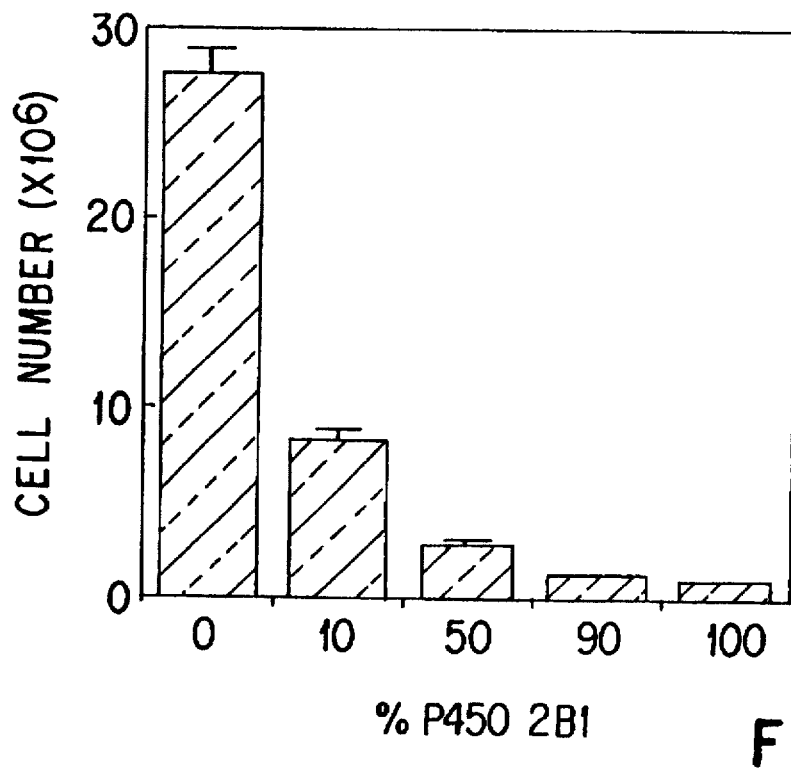
Figure 23B:
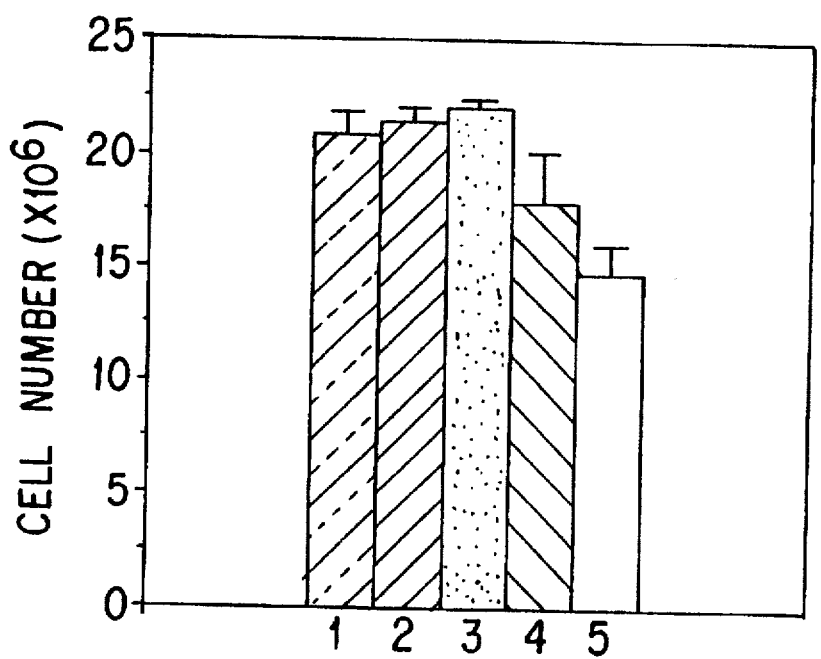

FIG. 23 is a bar graph depicting the cell-mediated effect. In FIG. 23A, the proliferation of C6 cells was assayed in the presence of 0.5 mM CPA when 0, 10, 50, 90, and 100% of the cells contained the P450 2B1 gene. The total number of cells per dish at the start of the experiment was $2\times10^6$ cells. Cells from each dish were counted five days later. The final values represent the average from three plates (mean±SE). In FIG. 23B, C6 cells were cultured alone ($2\times10^6$ cells) (bar 1), together with C6 cells that expressed the Neo gene (bar 2), irradiated C6 cells (bar 3), irradiated C6-Neo cells (bar 4), irradiated C6 cells that expressed the P450 gene (bar 5). In all instances, the total number of cells per dish was $2\times10^6$ and C6 cells accounted for 90% of cells in the dish at the start of the experiment. All cells were grown in the presence of 0.5 mM CPA for four days.

Figure 24:
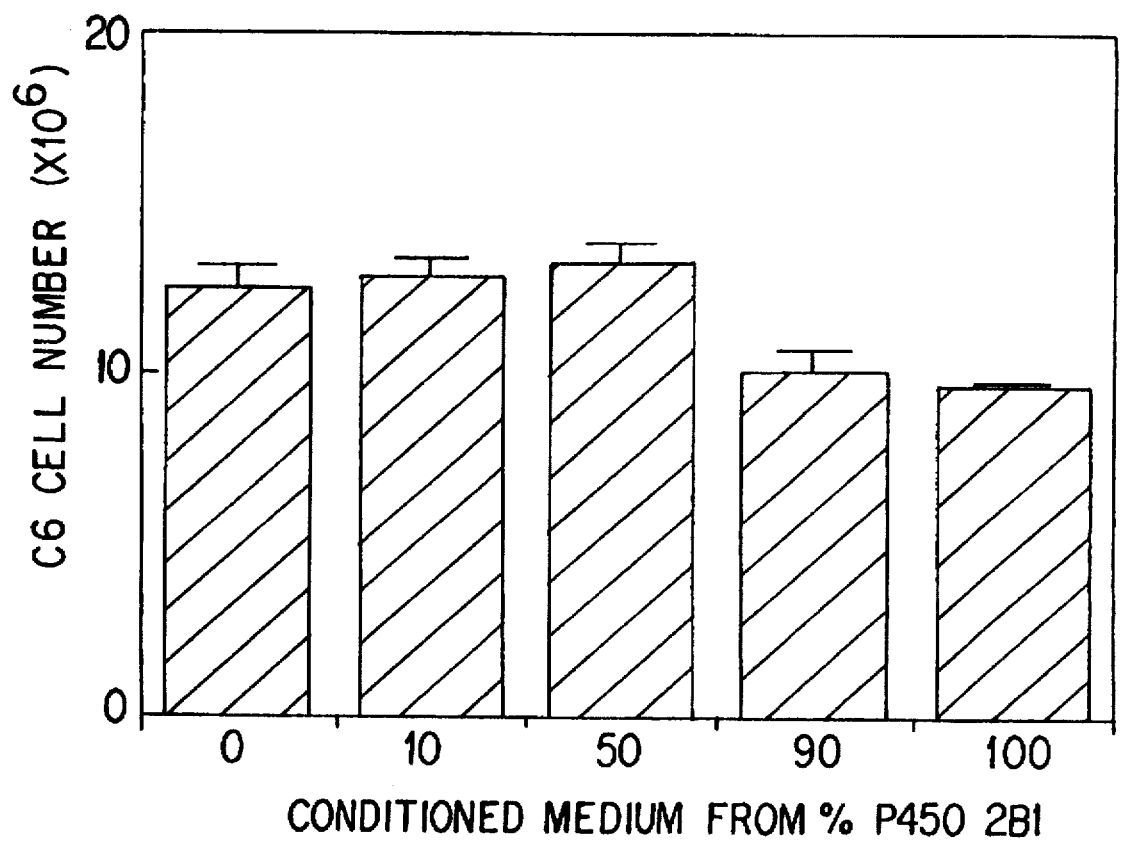

FIG. 24 is a bar graph depicting a comparison of killing efficacy between cell-mediated and secretory effects. Conditioned medium from each of the four day old co-culture assays shown in FIG. 23A was harvested, filtered and added to $2\times10^6$ C6 cells. C6 cell number was then measured five days later. The counts represent the average (±SE) from triplicate plates.

Figure 25:
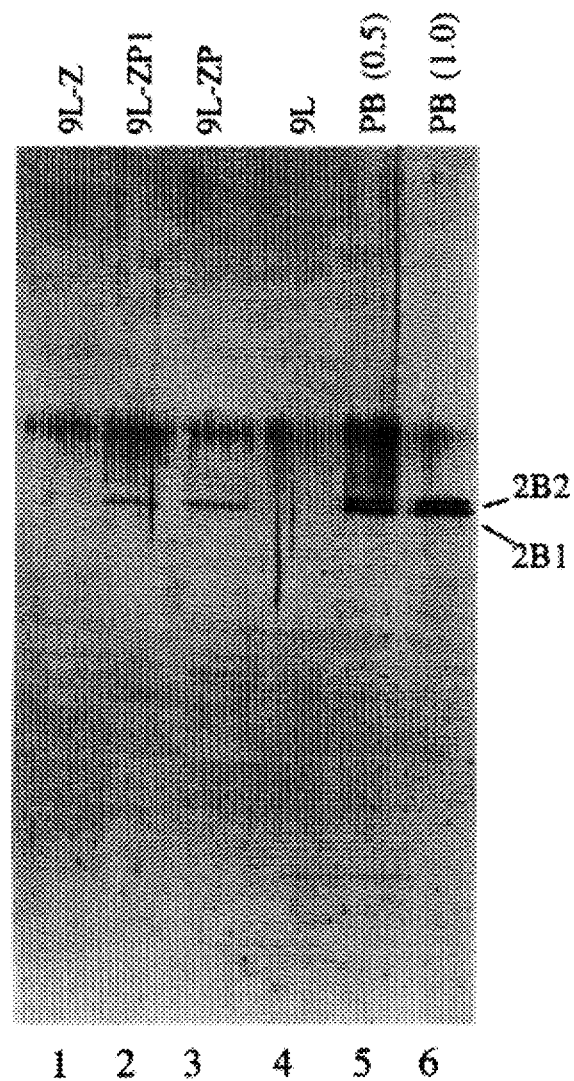

FIG. 25 is a Western blot analysis of cytochrome P450 2B1 in parental 9L cells and in 9L cells that stably express cytochrome P450 2B1. Microsomal proteins prepared from cultured cells (20 µg protein/lane) were electrophoresed on 10% SDS/polyacrylamide gels, transferred to nitrocellulose and probed with polyclonal rabbit anti-cytochrome P450 2B1 antibodies as described under Methods. 9L-ZP1 (lane 2) corresponds to a second clone derived from the same selection as 9L-ZP. It expresses cytochrome P450 2B1 and exhibits an oxazaphosphorine sensitivity very similar to that of 9L-ZP. Phenobarbital-induced rat liver microsomes (0.5 or 1 µg, lanes 5 and 6, respectively) were used as a standard for cytochrome P450 2B1 (lower band of doublet in lanes 5 and 6).

Figure 26A:
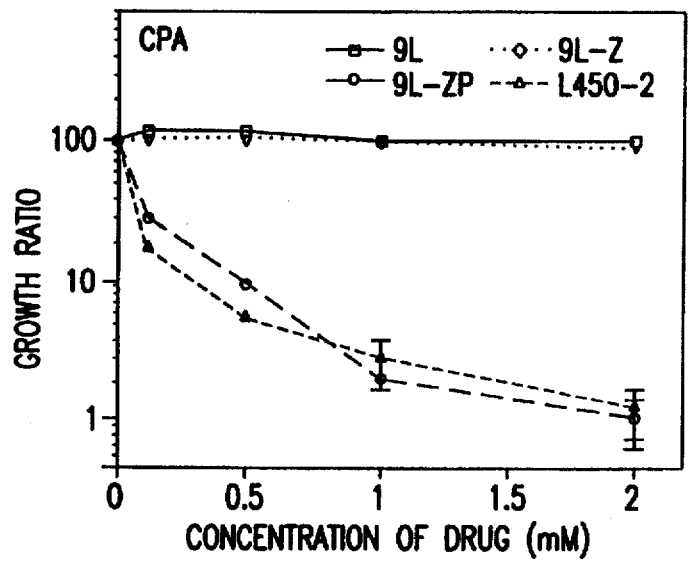
Figure 26B:
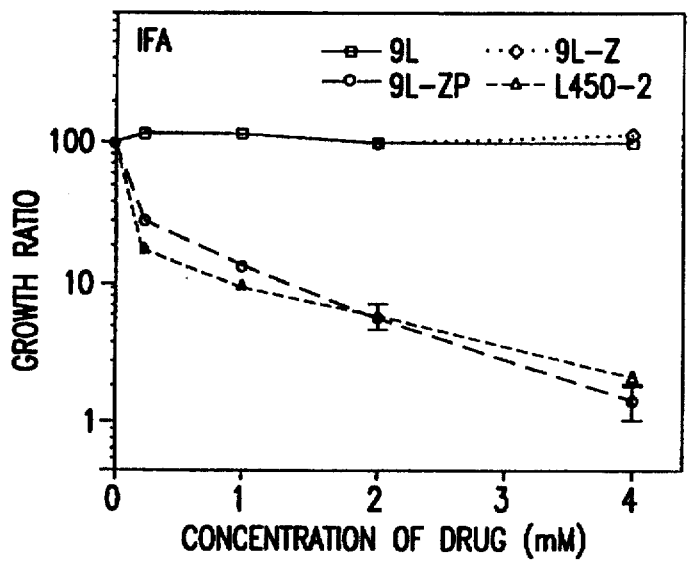
Figure 26C:
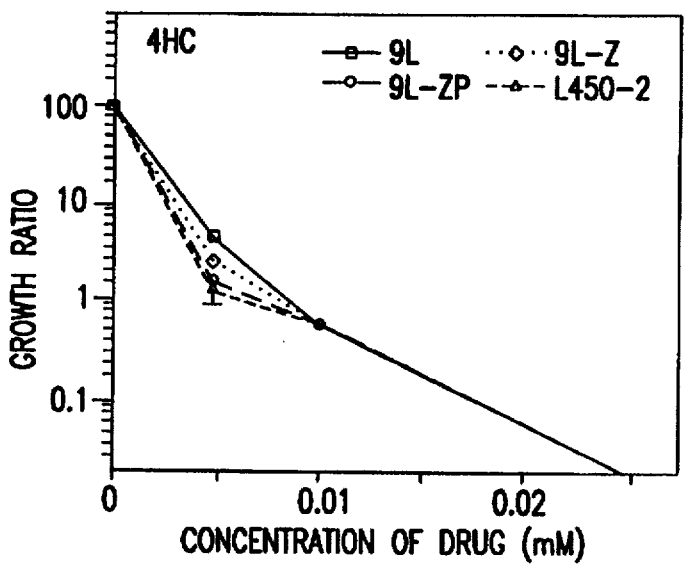

FIG. 26 are graphs showing cytotoxicity of oxazaphosphorines toward cytochrome P450 2B1-negative cells (parental 9L and 9L-Z) and cytochrome P450 2B1-positive cells (9L-ZP and L450-2). Cells ($1\times10^5$) plated in duplicate in 30 mm tissue culture plates were treated with the indicated concentrations of cyclophosphamide (CPA), ifosphamide (IFA), or 4-hydroperoxy cyclophosphamide (4HC) (FIGS. 26A–26C, respectively). Surviving cells were counted 5 days after beginning drug treatment as described under Methods. The effect of drugs on cell survival was expressed as growth ratio (%), i.e., cell number in plates containing drug as a percentage of the corresponding drug-free controls (mean±range for duplicate determinations). Final cell number ($\times10^4$) in drug-free controls=140±8 (9L), 135±7 (9L-Z), 140±10 (9L-ZP), 130±6 (L450-2) for each of the indicated cell lines.

Figure 27:
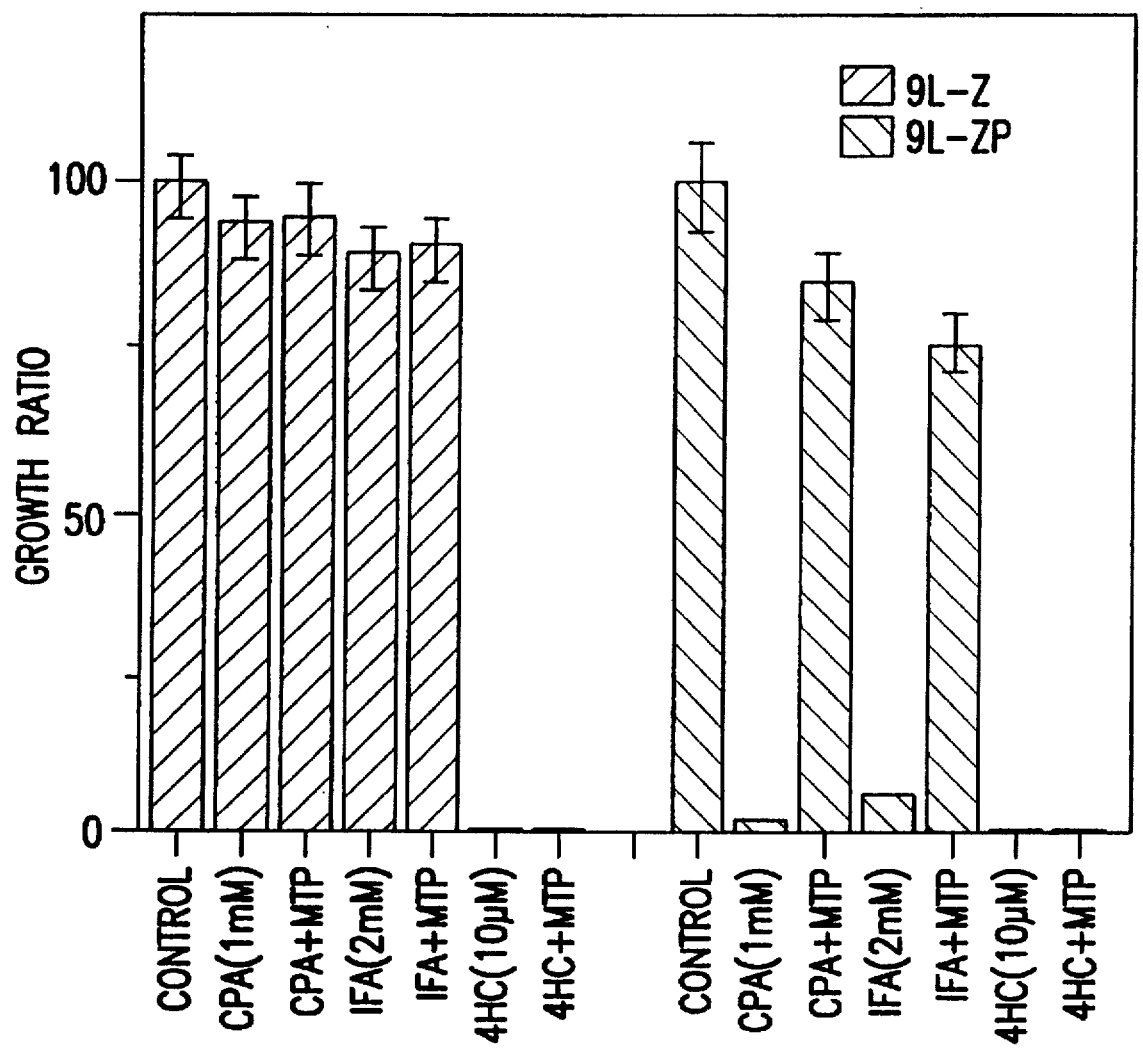

FIG. 27 is a bar graph showing that the cytochrome P450 2B1 enzyme inhibitor metyrapone (MTP) blocks the cytotoxic effects of cyclophosphamide (CPA) and ifosphamide (IFA) but not 4-hydroperoxy cyclophosphamide (4HC) on cytochrome P450 2B1-expressing cells. 9L-Z and 9L-ZP cells ($1\times10^5$) were treated with either 1 mM cyclophosphamide, 2 mM ifosphamide, or 10 µM 4-hydroperoxy cyclophosphamide in the absence or presence of 10 µM metyrapone, as indicated. Controls received no drug treatment. Cells numbers were determined 5 days after beginning drug treatment. Data (mean±range for duplicate determinations) are expressed as growth ratio (%) relative to drug-free controls.

Figure 28:
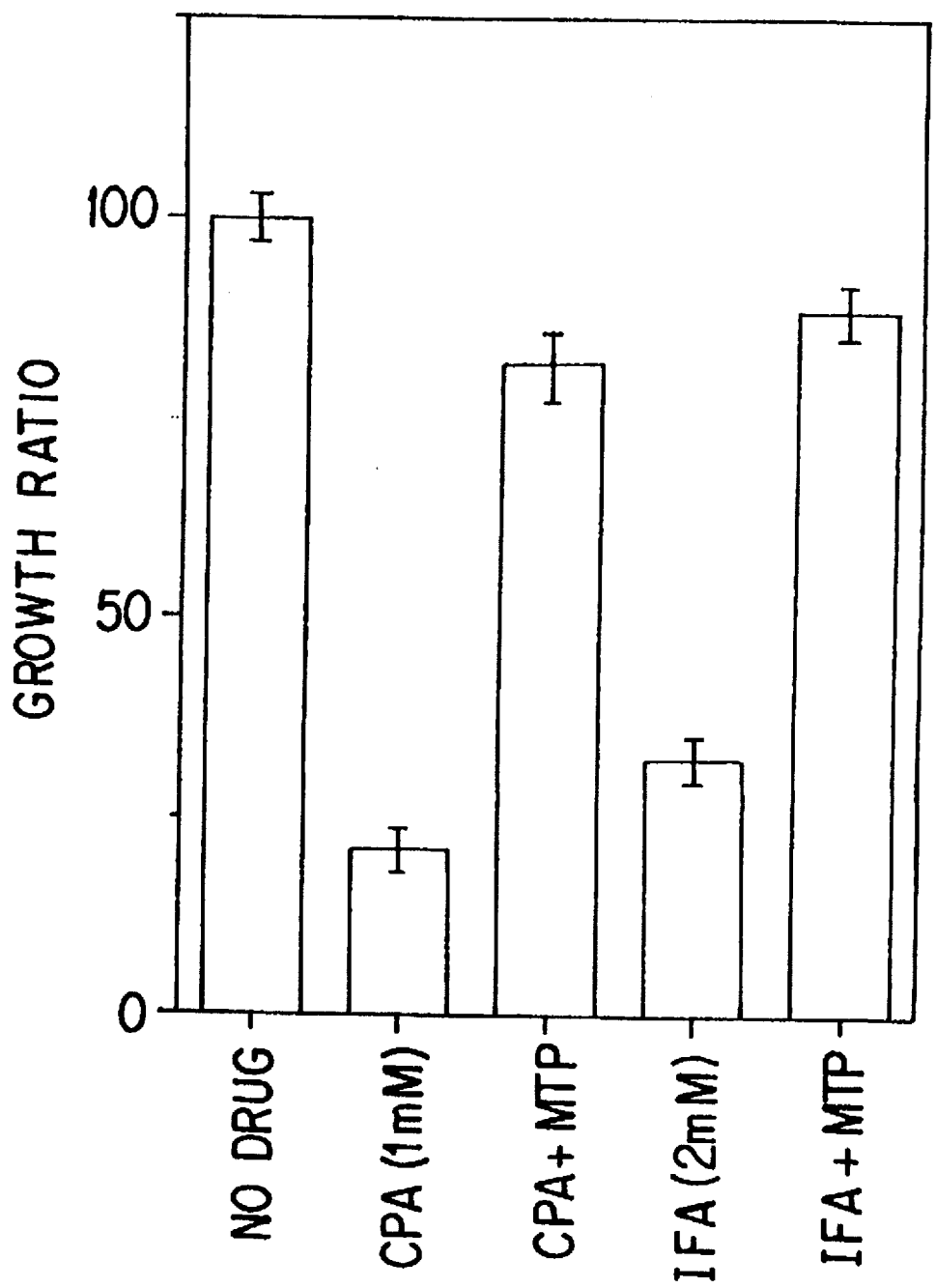

FIG. 28 is a bar graph depicting the cytotoxicity of oxazaphosphorines toward mixed cultures of 9L and 9L-ZP cells. Equal numbers of parental 9L cells were mixed with 9L-ZP cells (total initial cell number=$1\times10^5$/30 mm tissue culture dish). Cells were untreated or were treated with either 1 mM cyclophosphamide (CPA) or 2 mM ifosphamide in the absence or presence of 10 µM metyrapone (MTP), as indicated. Cell numbers were determined 5 days after beginning drug treatment. Data (mean ±range of duplicates) are expressed as growth ratio (%) relative to drug-free controls. In control experiments, cyclophosphamide exhibited no cytotoxicity toward mixed cultures of 9L and 9L-Z cells (data not shown).

Figures 29A, 29B, 29C:
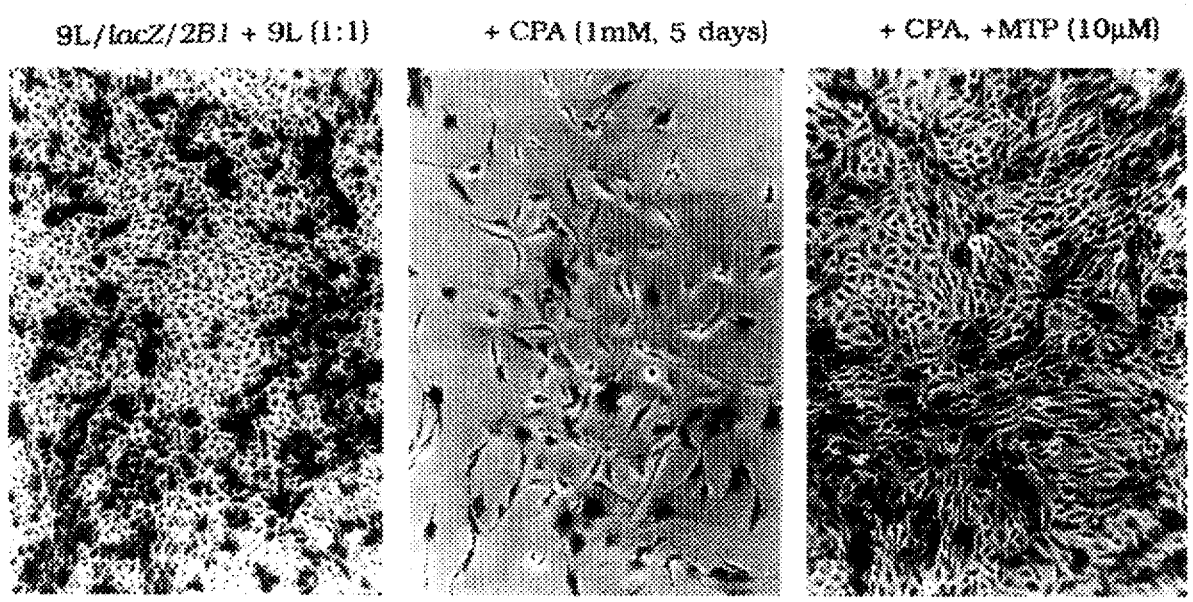

FIG. 29 is a histochemical analysis of lac Z-marked cytochrome P450 2B1-positive cells and unmarked cytochrome P450 2B1-negative cells in a mixed cell population. Equal numbers of parental 9L cells ($1\times10^5$) were mixed with lac Z-marked cytochrome P450 2B1-expressing 9L-ZP cells ("9L/lacZ/2B1") (FIG. 29A) and the effect of cyclophosphamide (CPA) (FIG. 29B) or cyclophosphamide with metyrapone (MTP) (FIG. 29C) on the surviving cells was assayed as in FIG. 23. Shown are cells fixed in 0.5% glutaraldehyde five days after beginning drug treatment and then stained with x-gal for 4 hours to visualize the 9L-ZP cells, shown here by dark staining.

Figure 30B:
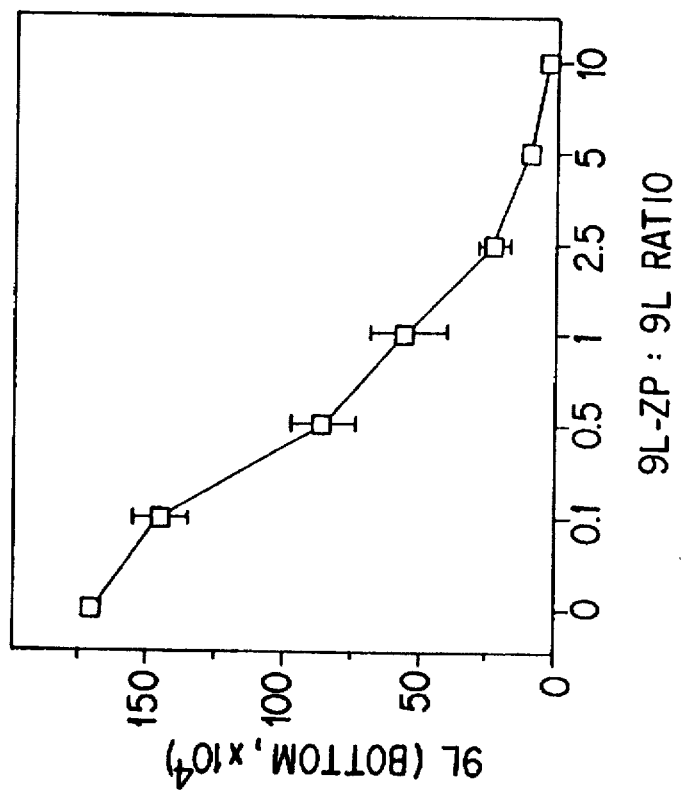
Figure 30A:
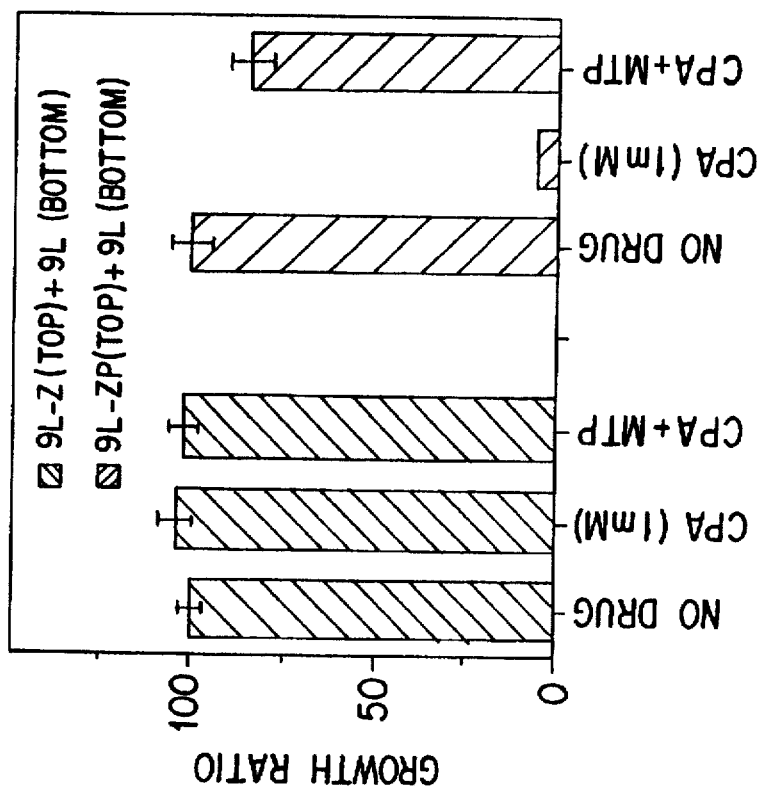

FIG. 30 consists of two graphs showing that soluble factors are involved in the bystander cytotoxicity of cyclophosphamide toward cytochrome P450 2B1-negative cells. In FIG. 30A, parental 9L cells ($1\times10^5$) were plated in the bottom well of 30 mm culture plates. Upper chambers of Falcon culture inserts were seeded with 9L-Z or 9L-ZP cells ($1\times10^6$), as indicated. The two cell populations were thus separated by a 0.45 µm pore size membrane, which prevents direct contact between the two cell populations. Cells were treated with 1 mM cyclophosphamide (CPA) with or without 10 µM metyrapone (MTP), or received no drug treatment, as control. Cell numbers were determined 5 days after beginning treatment. In FIG. 30B, the experimental system is the same as in panel A, except that the initial number of 9L-ZP cells in the top chamber (shown on the x-axis) was varied from $10^4$ to $10^6$, i.e., a ratio of 0.1 to 10 relative to the initial number of 9L cells in the bottom chamber. Shown on the y-axis are the final number of 9L cells in the bottom chamber 5 days after growth in the presence of 1 mM cyclophosphamide. Data (mean±range of duplicates) are presented as growth ratio (%) relative to drug-free controls.

Figure 31:
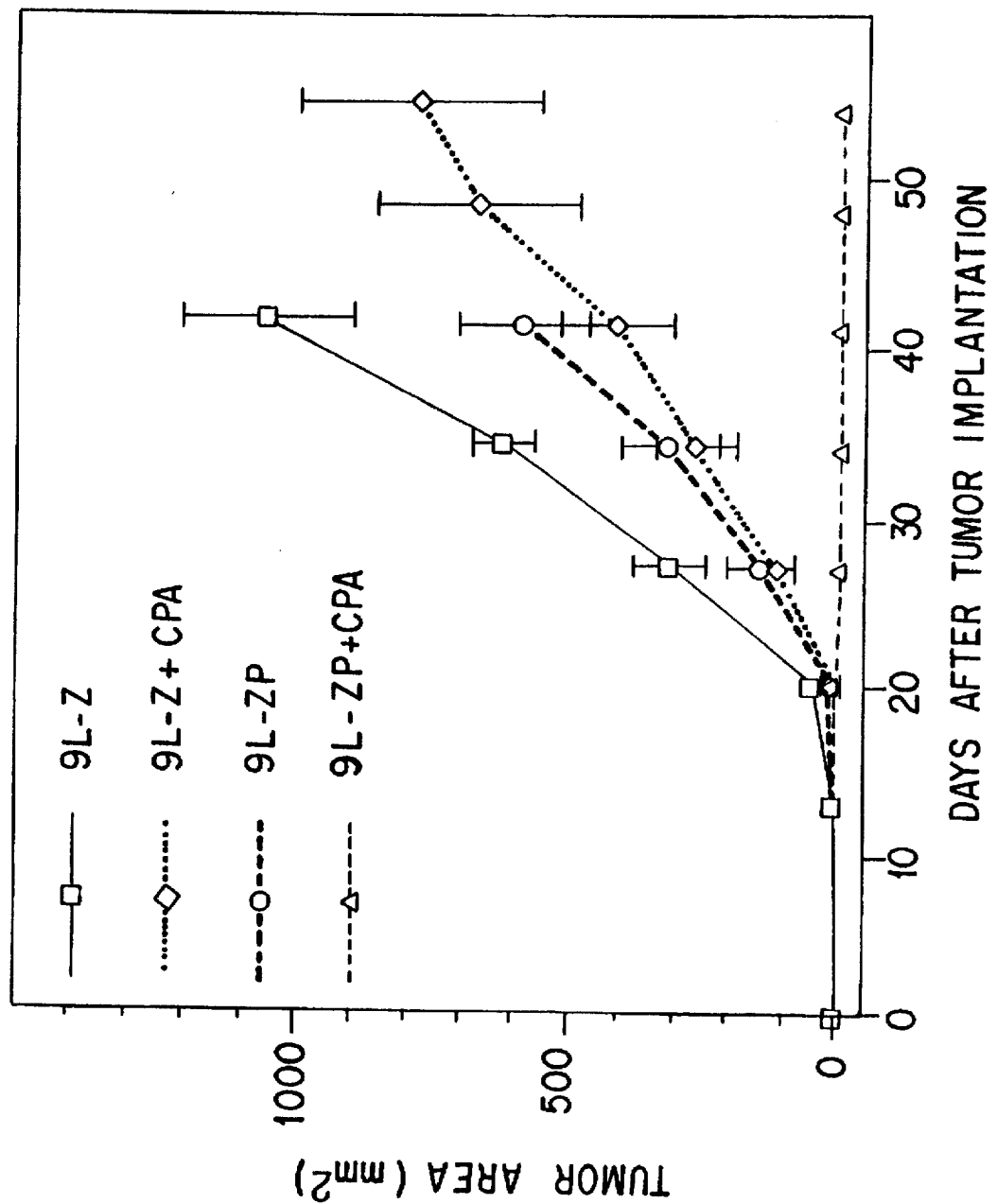

FIG. 31 is a graph depicting the growth inhibitory effects of cyclophosphamide toward 9L-Z and 9L-ZP tumors grown in vivo. Female Fisher 344 rats were inoculated with $2\times10^6$ 9L-Z or 9L-ZP cells by subcutaneous injection into the outer thighs (9L-Z cells on the right thigh and 9L-ZP cells on the left thigh). Seven days after tumor implantation, each rat received a single interperitoneal injection of cyclophosphamide (100 mg/kg body weight) or saline as control. Tumor areas were measured until the rats were sacrificed. Data shown are mean±SEM for n=5 tumors per group.

Figure 32:
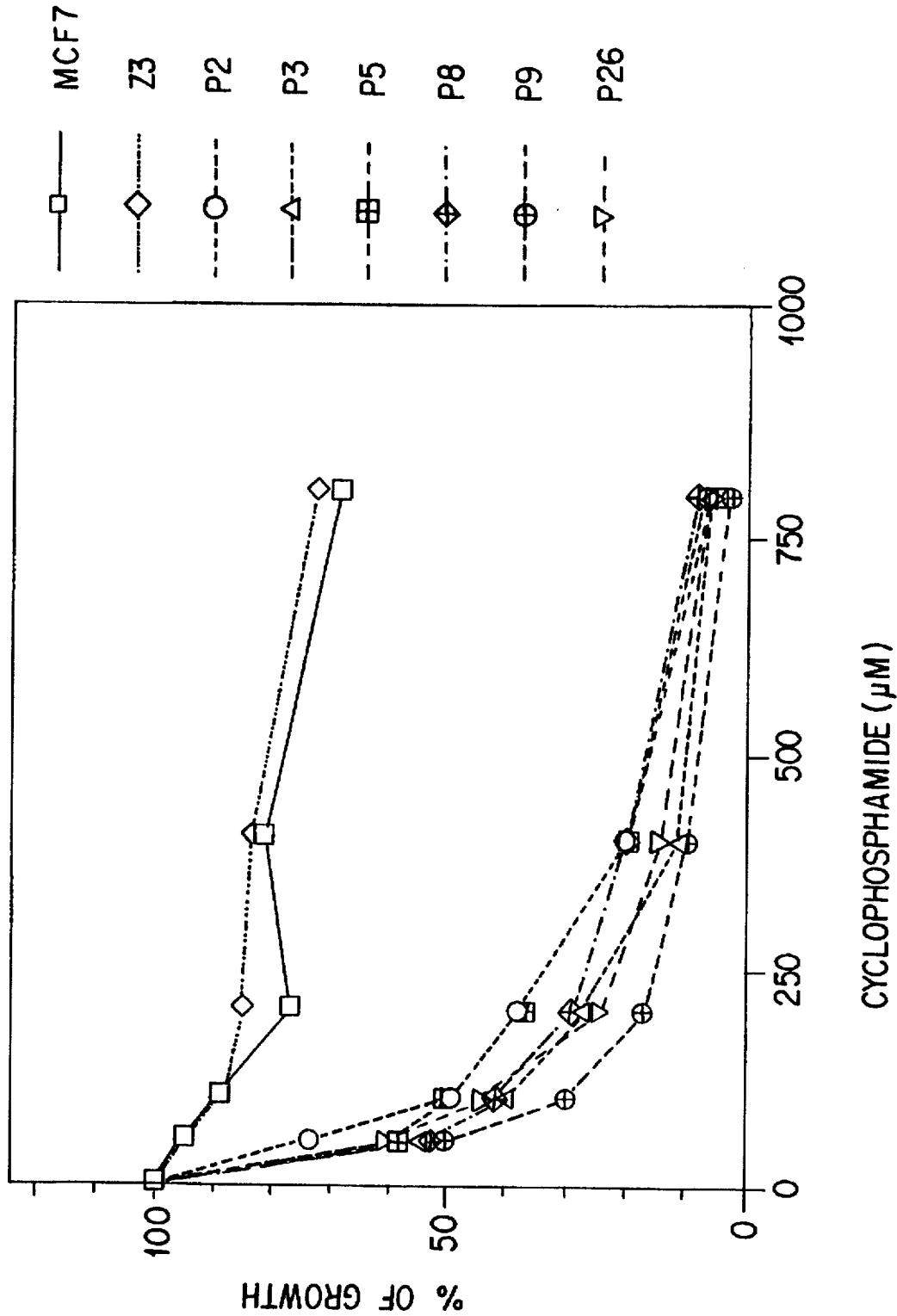

FIG. 32 is a graph depicting the high sensitivity of six cytochrome P450 2B1 -expressing MCF-7 human breast carcinoma cell lines to cyclophosphamide, in culture. The experimental design is the same as that described for FIG. 26.

Figure 33:
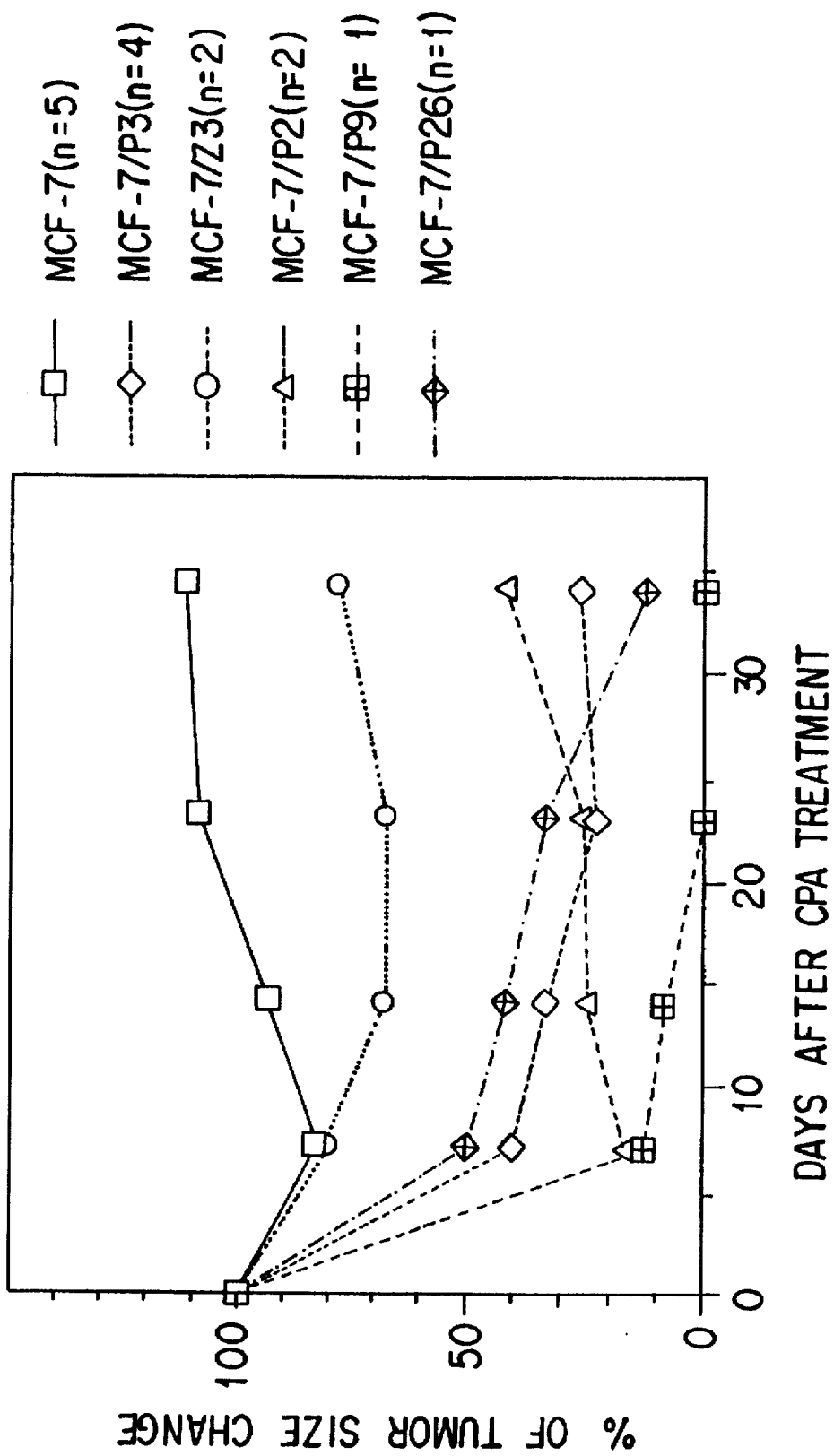

FIG. 33 is a graph comparing in vivo tumor cell kill obtained with four P450-expressing MCF-7 tumors (designated P3, P2, P9, and P26) to that of control tumors MCF-7 Z3, which express beta-galactosidase. Female homozygous nude athymic Swiss mice (nu+/nu+), 20–25 g were inoculated with each of the individual MCF-7 or cytochrome P450 2B1-expressing tumors shown in FIG. 32 by subcutaneous injection of $1 \times 10^7$ cells into the outer thighs. Shown is the effect of cyclophosphamide (CPA) on tumor growth in animals treated with cyclophosphamide given at 100 mg/kg body weight×2, by intraperitoneal injection on day 0 and again on day 2.

DESCRIPTION OF THE PREFERRED EMBODIMENTS

The present invention is drawn to the selective killing of neoplastic cells, and in particular, neoplastic cells of the nervous system. Viral vectors carrying a gene whose gene product is capable of targeting the neoplastic cells for selective cell death are utilized.

By neoplastic cells is intended dividing cells, usually rapidly dividing cells. For purposes of the invention, neoplastic cells include cells of tumors, neoplasms, carcinomas, sarcomas, leukemias, lymphomas, and the like. Of particular interest are central nervous system tumors. These include astrocytomas, oligodendrogliomas, meningiomas, neurofibromas, ependymomas, Schwannomas, neurofibrosarcomas, glioblastomas, etc. The neoplastic cells of particular concern to the invention are those cells of brain tumors. Adult brain tumors are unique in that they constitute masses of dividing cells within a background of essentially non-dividing cells. Therefore, the present invention utilizes these metabolic differences to exploit the development of a targeted approach to selective killing of neoplastic cells.

The invention can also be utilized to selectively kill both benign and malignant neoplastic cells in the periphery, as well as the brain. As used herein, the term periphery is intended to mean all other parts of the body outside of the brain. Thus, a peripheral tumor is intended to mean a tumor in a part of the body outside of the brain.

By viral vectors is intended DNA viruses, such as adeno-associated virus, adenovirus, herpesvirus, such as herpes simplex virus and Epstein-Barr virus, and retroviruses, such as MoMLV. Advantageously, the retroviral vectors of the invention can integrate only into the genome of dividing cells. Thus, the vectors provide a useful vehicle for selective targeting of dividing cells. Retroviral vectors offer further advantages as there are no limitations in host range and these vectors have already been used successfully to infect many different cell types. For example, see Cepko, C., "Lineage analysis and immortalization of neural cells via retrovirus vectors," in *Neuromethods* 16, The Humana Press, Clifton, N.J. (1989), pp. 177–219; Gilboa, E., *BioEssays* 5(6) :252–257 (1987); Friedmann, T., *Science* 244:1275–1281 (1989). One disadvantage, however, of retroviral vectors is the low production titer of the retrovirus.

In general, retroviral vectors are well known in the art. See, Breakefield et al., *Molec. Neuro. Biol.* 1:339 (1987); and, Shih et al., in *Vaccines* 85, Cold Spring Harbor Press, Cold Spring Harbor, N.Y. (1985), pp. 177–180. Further, co-pending U.S. patent applications Ser. Nos. 07/304,619 and 07/508,731 are drawn to herpes simplex virus expression vectors. The disclosures of these applications are herein incorporated by reference. These applications provide further information on the construction and use of retrovirus vectors.

As indicated above, generally, the retrovirus vectors of the present invention are replication-defective and can be packaged into infectious retroviral particles by transfected cell lines that contain retroviral sequences coding for the proteins necessary for the packaging of retroviral RNA, but which cannot package their own RNA. See, Mann et al., *Cell* 33:153–159 (1983); Danos and Mulligan, *Proc. Natl. Acad. Sci. USA* 85:6460–6464 (1988). Since retrovirus and vectors derived from them integrate into the host cell genome, their sequences are transmitted to all daughter cells. This feature of retroviruses has been successfully used for example, to trace cell lineages in the nervous system (Price et al., *Proc. Natl. Acad. Sci. USA* 84:156–160 (1987); Luskin et al., *Neuron* 1:635–647 (1988); Walsh and Cepko, *Science* 241:1342–1345 (1988)).

Genes for transfer into the neoplastic cells by the retroviral vectors are selected from those that target the host cell usually by the expression of a gene product in the host neoplastic cells. "Gene product" broadly refers to proteins encoded by the particular gene. However, for purposes of the invention, gene product also includes transcription products of the gene, particularly for use as anti-sense RNA. The host cells targeted by the present vectors are those cells into which the virus infects and expresses the desired gene product. The host cells thus constitute neoplastic cells infected by the retroviral vectors.

Genes are selected whose gene products serve to identify host cells, slow down or temporarily stimulate host cell growth in order to render the host cell more sensitive to chemotherapeutic agents, and/or whose products target the host cell for cell death. Cell death can be accomplished by contacting the host cells, comprising the gene product, with a subsequent treatment, either physical or chemical treatment. Alternatively, the gene products themselves may serve to kill the host cells or slow down cell growth. Gene products which temporarily stimulate cell growth include, for example, growth factors, including, for example, basic fibroblast growth factor (bFGF).

In this respect, one example of a useful gene product comprises imaging compounds that may be utilized for tumor location. The retrovirus is thus utilized as a means to diagnose the location and extent of the neoplastic growth. See, for example, Glatstein et al., *Int. J. Radiat. Oncol. Biol. Phys.* 11:299–314 (1985).

Genes are also selected whose products themselves are capable of selective cell killing. For example, the gene product may comprise anti-sense nucleic acid for essential cell proteins, such as replication proteins, which serve to render the host cells incapable of further cell growth and division. Anti-sense regulation has been described by Rosenberg et al., *Nature* 313:703–706 (1985); Preiss et al., *Nature* 313:27–32 (1985); Melton, *Proc. Natl. Acad. Sci. USA* 82:144–148 (1985); Izant and Weintraub, *Science* 229:345–352 (1985); Kim and Wald, *Cell* 42:129–138 (1985); Pestka et al., *Proc. Natl. Acad. Sci. USA* 81:7525–7528 (1984); Coleman et al., *Cell* 37:683–691 (1984); and McGarry and Lindquist, *Proc. Natl. Acad. Sci. USA* 83:399–403 (1986).

Other genes that find use for slowing cell growth include tumor suppressor genes, genes that encode transcription factors that suppress cell growth, toxic proteins that are released by cells, and the like. For example, see Heinbrook et al., *Proc. Natl. Acad. Sci. USA* 87:4697 (1990), which describes a fusion protein with toxin coupled to the EGF ligand. Toxin genes have also been described, for example, Barker et al., *Gene* 86:285–290 (1990); Ito et al., *Microb.*

*Pathog.* 8:47–60 (1990); Gannon et al., *J. Gen. Microbiol.* 136:1125–1136 (1990). Genes can also be inserted that alter cell growth characteristics or modulate cell growth, for example, a tumor suppressor gene, such as, the Rb gene in retinoblastoma (Huang et al., *Science* 242:1563–1566 (1988)) or the p53 gene in colon cancer (Baker et al., *Science* 249:912–915 (1980)). Other suppressor or modulating genes can also be utilized.

Genes whose products serve to render the host cells more antigenic also find use in the invention. This antigenic effect can be accomplished by introducing new antigens on the surface of the host cells, thus augmenting the immune system in recognizing the tumor as a foreign body. The introduction of new antigens to the surface of the host cells is referred to as xenogenization of the cells (Austin et al., *Ad. in Cancer Res.* 30:301–345 (1979); Kobayashi et al., *Ad. in Cancer Res.* 30:279–299 (1979)). Any nonhuman surface antigen can be utilized including those described in Araki et al., *Gene* 89: 195–202 (1990); Takle et al., *Mol. Biochem. Parasitol.* 37:57–64 (1989); Raney et al., *J. Virol.* 63:3919–3925 (1989); Tondravi, M. M., *Curr. Genet.* 14:617–626 (1988); and Miyanohara et al., *Proc. Natl. Acad. Sci. USA* 80:1–5 (1983).

The expression of nonhuman or unique surface antigens in neoplastic cells can also be utilized to locate such neoplastic cells by subsequent binding with labelled antibodies. See, for example, Le Doussal et al., *Cancer Res.* 50:3445–3452 (1990); Palabrica et al., *Proc. Natl. Acad. Sci. USA* 86:1036–1040 (1989); Berends et al., *Cancer Immunol. Immunother.* 26:243–249 (1988); and Welt et al., *Proc. Natl. Acad. Sci. USA* 84:4200–4204 (1987).

In another embodiment, a gene or coding sequence can be selected whose gene product offers a conditional killing mechanism for dividing cells. In this manner, the expression of a particular protein followed by the subsequent treatment is effective in killing the neoplastic cells. The subsequent treatment comprises chemical and physical treatments. Agents for chemical treatments comprise the use of enzymes or other compounds that react with the gene product to kill the host cell. Physical treatments comprise subjection of the cells to radiation, UV light, and the like.

For example, the herpes simplex virus type I (HSV-1) thymidine kinase (TK) gene offers such a conditional killing mechanism for dividing cells. The selective advantage of using HSV-1-TK derives from the higher affinity the enzyme has for certain nucleoside analogues, such as acyclovir, ganciclovir, and FIAU, than mammalian TK (McLaren et al., in *Herpes Virus and Virus Chemotherapy*, R. Kono, ed., Elsevier, Amsterdam, (1985), pp. 57–61). These drugs are converted to nucleotide-like precursors and incorporated into the DNA of replicating cells, thus disrupting the integrity of the genome, and ultimately leading to cell death. Several studies have successfully made use of the conditional toxicity of TK in development studies of transgenic mice (Borrelli et al., *Nature* 339:538–541 (1989); Heyman et al., *Proc. Natl. Acad. Sci. USA* 86:2698–2702 (1989)), as a selectable marker against non-homologous recombination events in cultured cells (Capecchi, M. R., *Trends in Genetics* 5(3):70–76 (1989)), for killing cells harboring wild type herpes viruses (Corey et al., *N. Engl. J. Med.* 314:686–691 (1986); Corey et al., *N. Engl. J. Med.* 314:749–756 (1986)), and in selecting for herpes virus mutants lacking TK activity (Coen et al., *Science* 234:53–59 (1986)).

In a preferred embodiment, the cytochrome P450 gene is utilized to sensitize neoplastic cells to the cytotoxic effects of a chemotherapeutic agent that is activated by one or more cytochrome P450 genes. The term cytochrome P450 gene, as used herein, shall mean a mammalian cytochrome P450 gene such as, P450 2B1, P450 2B6, P450 2A6, P450 2C6, P450 2C8, P450 2C9, P450 2C 11, or P450 3A4. Each of these genes has been linked to activation of the anticancer drugs cyclophosphamide or ifosphamide (Clarke et al., *Cancer Res.* 49:2344–2350 (1989); Chang et al., *Cancer Res.* 53:5629–5637 (1993); Weber and Waxman, *Biochemical Pharmacology* 45:1685–1694 (1993)), and the cDNA sequences of these genes have also been published (Nelson et al., *DNA and Cell Biology* 12:1–51 (1993) and references cited therein; Yamano et al., *Biochem.* 29:1322–1329 (1990); Yamano et al., *Biochem.* 28:7340–7348 (1989)). Persons of ordinary skill in the art should be able to utilize the method of the present invention with numerous other anticancer drugs that are activated by members of the cytochrome P450 family of enzymes (LeBlanc and Waxman, *Drug Metab. Rev.* 20:395–439 (1989)), as well as with drug-metabolizing cytochrome P450 genes from other species (e.g., mouse, rabbit, hamster, dog, etc.) that are homologous to cytochromes P450 2B1, P450 2B6, P450 2A6, P450 2C6, P450 2C8, P450 2C9, P450 2C 11, or P450 3A4, and whose cDNA sequences are known (Nelson et al., *DNA and Cell Biology* 12:1–51 (1993)).

In a particularly preferred embodiment, the cytochrome P450 2B1 gene is utilized to sensitize central nervous tumor cells to the cytotoxic effects of cyclophosphamide (CPA). Most malignant tumors of the central nervous system do not respond well to chemotherapy. The anticancer drug cyclophosphamide (CPA) is largely ineffective against central nervous system neoplasms as its conversion to DNA-alkylating, cytotoxic metabolites is restricted primarily to the liver and these metabolites do not readily cross the blood-brain barrier. It has now been shown that brain tumor cells can be sensitized to the cytotoxic effects of CPA, both in culture and in vivo, by introduction of the hepatic enzyme cytochrome P450 2B1, which is responsible for the activation of the inert prodrug, CPA. Stable transfection of rat C6 glioma cells with the P450 2B1 gene rendered the tumor cells sensitive to CPA in culture. Further, C6 cells bearing this gene were more sensitive than parental cells to the cytotoxic action of CPA when grown subcutaneously in the flanks of athymic mice. Murine fibroblasts producing a retrovirus vector encoding P450 2B1 and expressing this enzyme were then prepared and grafted into the brains of athymic mice seeded with rat C6 gliomas. The intrathecal administration of CPA prevented the development of meningeal neoplasia and led to partial regression of the parenchymal tumor mass. By contrast, C6 glioma-bearing control mice receiving fibroblasts expressing the *E. coli* lacZ gene followed by CPA exhibited both extensive meningeal tumors and parenchymal solid brain tumors.

In summary, expression of the cytochrome P450 2B1 gene in C6 glioma cells was found to lead to tumor cell destruction following CPA treatment in culture, and in subcutaneous tumors in athymic mice. In addition, experimental brain tumors in mice were sensitized to CPA after grafting retrovirus-producing fibroblasts expressing P450 2B1 into the tumor mass. Previous reports have also shown that Chinese hamster ovary cells stably transfected with the cytochrome P450 2B1 gene acquired chemosensitivity to cyclophosphamide, ifosphamide, and aflatoxin B1, and can be used to assay for the toxicity of these agents (Doehmer et al., *Proc. Natl. Acad. Sci. USA* 85:5769–5773 (1988); Doehmer et al., *Environ. Health Prospect* 88:63–65 (1990)). Previous reports have also shown that transgenic Drosophila larvae expressing the P450 gene are hypersensitive to cyclophosphamide (Jowett et al., *EMBO J* 10:1075–1081 (1991)), and that human lymphoblastoid cell lines that stably express cytochrome P450 2B6 or P450 2A6 are chemosensitive to cyclophosphamide and ifosphamide (Chang et al., *Cancer Res.* 53:5629–5637 (1993)). The inventors' findings now demonstrate that the cytochrome P450 2B1 gene is an effective drug-conditional killing gene for dividing cells, with novel applications to tumor gene therapy and to a variety of procedures that require a negative-selection mechanism.

The in situ activation of CPA by cytochrome P450 2B1 provides a novel approach not only for brain tumor gene therapy, but also for the negative, drug-conditional selection of other defined cell populations. Thus, in another preferred embodiment, the cytochrome P450 2B1 gene is utilized to sensitize peripheral tumors to the cytotoxic effects of CPA.

In this regard, the inventors employed 9L gliosarcoma cells that are stably transfected to express cytochrome P450 2B1 to evaluate the cytochrome P450 2B1/oxazaphosphorine system for cancer gene therapy. In vitro experiments and an in vivo tumor growth delay study comparing the CPA sensitivity of parental 9L cells to that of cytochrome P450 2B1-expressing 9L tumor cells demonstrated that a subcutaneous solid tumor can be rendered highly susceptible to oxazaphosphorine treatment in cases where intratumoral prodrug activation can be achieved by the tumoral expression of the cytochrome P450 2B1 gene. In addition, the inventors have demonstrated that MCF-7 human breast carcinoma cells, transfected to express cytochrome P450 2B1, were sensitized to cyclophosphamide in cell culture and in a nude mouse model.

It is reasonable to believe that the method of the invention should allow more tumor toxicity at the same drug concentration, thus allowing for higher tumor doses without increasing toxicity to normal cells. Further, chemotherapeutic treatment of systemic tumor populations may also be improved by using the method of the present invention because lower doses of the drug may be possible by virtue of increased efficiency.

The gene product may also encode a chemical or protein which renders the host cells radiosensitive and thus more susceptible to killing by radiation. Thus, upon subsequent subjection to radiation, the host cells are selectively killed. For example, the combination of the HSV-TK gene and ganciclovir, can be used. Cells bearing the HSV-TK gene show increased sensitivity to radiation in the presence of ganciclovir, as its metabolites interfere with DNA repair as well as DNA synthesis. See Snyderman et al., *Arch. Otolaryngol. Head Neck Surg.* 112:1147–1150 (1986); and Sealy et al., *Cancer* 54:1535–1540 (1984). Other strategies include selective transfer of cell surface antigenic markers, in conjunction with the development of tumor-specific immunoconjugates to improve targeting of chemotherapeutic agents. See, Reisfeld, R. A., in *Molecular Probes Technology and Medical Applications*, Albertini et al., Raven Press, New York (1989).

It is recognized that the gene of interest can be modified by any method known in the art. For example, the gene can be placed under the control of heterologous regulatory regions, including the use of viral promoters, neoplastic cell or tumor specific promoters or control elements. For example, the DF3 gene, expressed in the majority of human breast cancers, can be used to direct expression of "suicide genes" in breast cancer cells (Manome et al., *Cancer Res.* 54:5408–5413 (1994)). These methods could be readily applied to the cytochrome P450 2B1/CPA gene therapy paradigm disclosed herein. In this manner, the gene product is further targeted to specific cell types. Methods for construction of such expression vectors are known in the art.

Generally, methods are known in the art for retroviral infection of the cells of interest. The virus can be injected into the host at or near the site of neoplastic growth. For the most part, the virus is provided in a therapeutically effective amount to infect and kill target cells. Generally, the virus is provided for injection in a concentration in the range of about $10^1$ to about $10^{10}$ plaque forming units (PFU), generally about $5 \times 10^4$ to about $1 \times 10^6$ PFU, more generally about $1 \times 10^5$ to about $4 \times 10^5$, although ranges may vary. More typically, however, the packaging cell line can be grafted near or into the tumor to provide a longer-lasting source of virus. Recently, retrovirus vectors have been successfully packaged with a vesicular stomatitis virus (VSV) envelope protein. These vectors are more stable and can be injected directly, also achieving higher liters of the retrovirus. (Burns et al., *Proc. Natl. Acad. Sci. USA* 90:8033–8037 (1993)).

This selective killing of the retrovirus and delivery of the toxic gene can be enhanced by co-infection with a helper virus. That is, the helper virus augments gene delivery. In this manner, the packaging cell lines for making virus particles of the retrovirus vectors can be coinfected with a helper virus. Packaging cells or viral inoculum is then injected into the host at or near the site of infection. (See, Cepko, C. (1989), supra; Rosenberg et al., *Science* 242:1575–1578 (1988); and Mann et al., *Cell* 33:153–159 (1983)). Such helper viruses include ecotropic wild-type retroviruses, for example MoMLV (See, Danos et al., *Proc. Natl. Acad. Sci. USA* 85:6460–6464 (1988); Cepko, C., in *Neuromethods*, vol. 16, *Molecular Neurobiological Techniques*, Boulton et al., eds., The Humana Press, Inc., Clifton, N.J. (1989); and Mann et al., *Cell* 33:153–159 (1983)).

To utilize a helper virus, the packaging line or retroviral vector-infected line can be subsequently infected with wild-type virus in culture and these cells can be grafted. (See, Rosenberg et al., *Science* 242:1575–1578 (1988) and Wolff et al., *Proc. Natl. Acad. Sci. USA* 86:9011–9014 (1989)). The packaging cells are infected with the helper in the range of MOI of about 0.1 to about 20.

The sensitivity of the tumor cells to toxic agents is increased utilizing helper viruses. The helper viruses turn cells infected with retrovirus vectors into packaging cell lines. The results show that by co-infection with a helper virus, the retrovirus vectors of the invention are able to target more tumor cells, even those tumor cells away from the tumor mass. Furthermore, the tumor cells die faster and show more sensitivity to toxic agents when a helper virus is utilized.

The invention finds particular use in the treatment of glioblastomas. The glioblastoma represents approximately 30% or 50% of all primary brain tumors and, despite surgery, chemotherapy, and radiotherapy, is almost universally fatal. The mean survival is less than a year, and the five-year survival rate is only 3% or 5%. After treatment, recurrence of the disease often appears within two centimeters of the original site. Metastases are extremely rare; neurological dysfunction and death are due to local growth and cerebral invasion. Therefore, the possible efficacy of local (non-systemic) treatments has been explored. A few of these include studies of local hypothermia, photodynamic therapy, and interstitial radiation. However, until the present invention, no therapeutic modality has made a substantial impact on the outcome of patients with malignant gliomas.

The following Examples are offered by way of illustration, not by way of limitation.

Experimental

EXAMPLE 1

Primary human brain tumors (malignant gliomas) are not encapsulated and it is therefore difficult to ensure their complete removal surgically. Many of these tumors are non-metastatic and may, at times, only invade a few centimeters into the surrounding tissue. However, surgery, radiotherapy, and chemotherapy have only had a modest impact on the overall morbidity and mortality of affected individuals. Novel, targeted approaches to the treatment of malignant gliomas are worthy of exploration.

Brain tumors are unique in that they constitute masses of dividing cells within a background of essentially non-dividing cells. These metabolic differences can be exploited in the development of targeted approaches to therapy. Retroviral vectors provide a useful vehicle for selective targeting since (1) they can only integrate into the genome of dividing cells; (2) there are no limitations in host range; and (3) these vectors have already been used successfully to infect many different cell types (for review, see Cepko, C., in *Neuromethods, vol. 16, Molecular Neurobiological Techniques*, Boulton et al., eds., The Humana Press, Clifton, N.J. (1989), pp. 177–218; Gilboa, E., *BioEssays* 5:252–257 (1987); Friedmann, T., *Science* 244:1275–1281 (1989)). The retrovirus vectors are replication-defective and can be packaged into infectious retroviral particles by transfected cell lines which contain retroviral sequences coding for the proteins necessary for the packaging of retroviral RNA, but which cannot package their own RNA (e.g., Mann et al., *Cell* 33:153–159 (1983)); Danos et al., *Proc. Natl. Acad. Sci. USA* 85:6460–6464 (1988)). Since retroviruses and vectors derived from them integrate into the host cell genome, their sequences are transmitted to all daughter cells. This feature of retroviruses has been successfully used, for example, to trace cell lineages in the nervous system (Price et al., *Proc. Natl. Acad. Sci. USA* 84:156–160 (1987); Luskin et al., *Neuron* 1:635–647 (1988); Walsh et al., *Science* 241:1342–1345 (1988)).

The herpes simplex virus type 1 (HSV-1) thymidine kinase (TK) gene offers a conditional killing mechanism for dividing cells. The selective advantage of using HSV-1-TK derives from the fact that this enzyme has a higher affinity for certain nucleoside analogs, such as ganciclovir. These drugs are converted to nucleotide-like precursors and incorporated into the DNA of replicating cells, thus disrupting the integrity of the genome, and ultimately leading to cell death.

In this study, rat C6 glioma cells were used as a model primary brain tumor type. C6 cells rapidly form a non-encapsulated, non-metastatic tumor after injection into the adult rat CNS. Further, derivative cell lines are available, which lack endogenous TK activity (C6-BUI) or bear the lacZ gene (C6-BAG), which are useful experimentally. A retroviral vector was generated in which the HSV-1-TK gene is regulated by the strong, constitutive retrovirus LTR promoter. C6-BUI cells were infected with this vector and selected for TK activity by growth in HAT medium. Parental and infected cells were tested for their dose-dependent sensitivity to ganciclovir in culture and in vivo following inoculation into the rat subrenal capsule.

Material and Methods

Vector Construction: A 2.8 kb BamHI fragment encompassing the full coding sequence and 2 kb of the 3' non-coding region (including the polyA addition site) of the HSV-1 TK gene (from plasmid pBRTK) were cloned into the BamHI site of a retroviral plasmid, pL(X)RNL. The resulting plasmid is called pLTKRNL. The pL(X)RNL plasmid is derived from Moloney murine leukemia retrovirus (MoMLV) and Moloney murine sarcoma retrovirus (MoMSV), and contains the following elements: a retroviral packaging sequence, psi; the neomycin-resistance (neo®) gene from transposon Tn5 placed under the transcriptional control of a Rous sarcoma virus (RSV) promoter; the colE1 bacterial origin of replication; and the bacterial ampicillin resistance gene. The plasmid is basically similar to those reported in Wolff et al., *Proc. Natl. Acad. Sci. USA* 86:9011–9014 (1989); Short et al., *Devel. Neurosci.* 12:34–45 (1990); and Price et al., *Proc. Natl. Acad. Sci. USA* 84:156–160 (1987); except that it uses an RSV promoter to drive neo®.

The BAG retroviral vector contains the *Escherichia coli* lacZ gene under the transcriptional control of a retroviral LTR promoter, the transposon Tn5 neo® gene under the transcriptional control of the SV40 early promoter-enhancer element, and other features as above (Price et al., *Proc. Natl. Acad. Sci. USA* 84:156–160 (1987)).

Cell Culture: An ecotropic retrovirus-packaging line, psi2, was used that was derived from a mouse fibroblast line (Mann et al., *Cell* 33:153–159 (1983)). The C6 rat glioma-derived cell lines used were: C6-BU1 (Amano et al., *Exp. Cell Res.* 85:399–408 (1974)), a line selected in BUdR for loss of endogenous thymidine kinase activity, and C6-BU1-BAG, a derivative of C6-BU1 expressing β-galactosidase activity following infection with the BAG virus. The psi2-derived line psi2-BAG-2-14 (Short et al., *Dev. Neurosci.* 12:34–45 (1990)) was used to obtain BAG virus. All cell lines were grown in Dulbecco's modified Eagle medium (GIBCO) containing 10% fetal bovine serum (FBS brand), 100 units of penicillin, and 100 µg of streptomycin per mL. Neomycin-resistant cells were selected and maintained in the same medium supplemented with 1 mg/mL G418 (neomycin analog, GIBCO). Cells expressing HSV-1-TK were selected by including HAT (hypoxanthine-aminopterin-thymidine, GIBCO) in the growth medium.

Transfections, Virus Production and Infections: To produce replication-defective, HSV-1-TK-bearing retroviral vectors (v-TK), 10 µg of pLTKRNL plasmid DNA were transfected into psi2 cells by the calcium phosphate co-precipitation method using glycerol shock by standard method. Transfected psi2 colonies were selected in medium containing G418. To make virus stocks, cultures were maintained in medium with G418 until they reached 80% confluency, then they were fed medium without G418 and twenty-four hours later, the virus-containing ("conditioned") medium was removed, filtered through a 0.45 µm pore size filter, and stored at −70° C.

All infections were done by replacing medium on a 100 mm tissue culture dish of recipient cells with 2 mL of medium containing 4 µg/mL polybrene (Sigma) and varying amounts of virus stock.

Virus titers of the psi2-v-TK line were determined by infecting C6-BUI cells, and determining the number of HAT-resistant colonies obtained per unit volume of virus stock. Two HAT-resistant clones, C6TK-vTK1 and 3, were used for further studies. For the psi2-BAG lines, virus titers were determined the same way, using NIH3T3 cells, and selecting for G418 resistance.

Histochemical Staining for β-galactosidase: To visualize µ-galactosidase expression, cells were fixed in 0.5% glutaraldehyde in phosphate-buffered saline, pH 7.3, for 5 minutes at room temperature, and then stained with 5-bromo-4-chloro-3-indolyl-B-D-galactoside for 30 minutes to 4 hours at 37° C. (Turner and Cepko, *Nature* 328:131–136 (1987)).

Ganciclovir Sensitivity Assays in Culture: The following cell lines: C6, CC6-BU1, C6-VIK1 and 3, were assayed for dose-dependent toxicity of the nucleoside analog ganciclovir (Cytovene, Burroughs Wellcome). Cells were plated at a density of 100 per 100 mm dish. Seventy-two hours later, ganciclovir was added at varying concentrations to each dish, and the incubation was continued for 9 days, changing the ganciclovir-containing medium every 3 days. The concentrations of ganciclovir tested were: 0, 3, 10, 30, 100, and 300 μm, in triplicate. On the 9th day, the medium was removed, the dishes were washed with PBS, fixed with 100% methanol for 10 minutes, stained with a 1:10 dilution of Giemsa (Fisher) in distilled water for another 10 minutes, washed again with water, then dried (Freshney, R. I., *Culture of Animal Cells—A Manual of Basic Technique*, 2nd ed., New York, Alan R. Liss, Inc. (1987)). Colonies were counted and the number on dishes with no ganciclovir was taken to represent 100% survival.

Results

Vector Construction: The integrity and orientation of the HSV-1 TK gene in the plasmid pLTKRNL were confirmed by restriction mapping. Upon cleavage with BamHI, two bands of approximately 2.8 kb and 6.7 kb were obtained, as expected from the respective sizes of the HSV-1 TK gene and the pL(X)RNL vector. Based on the sequence of the HSV-1 TK gene (McKnight, S. L., *Nucleic Acids Res.* 8(24):5949–5964 (1980)), fragments of the expected sizes were also obtained upon cleavage with the restriction endonucleases, PstI and SmaI. Insertion of the HSV-1 TK gene into the BamHI site of the pL(X)RN L vector placed it under the control of the MoMLV LTR promoter.

Transfection, Infection: The packaging line, psi2-TK, produced $10^4$ cfu/mL. No helper virus production by this clone could be detected. Virus from psi2-TK was used to establish C6-derived (C6-vTK) cell lines, which grew in HAT medium.

Ganciclovir Sensitivity in Culture: The cell lines compared in the sensitivity assay were C6, C6-BU1 and C6VIK-1 and -3.

Ganciclovir Sensitivity in vivo: Nine rats were implanted in the subrenal capsule with C6VIK cells. Four survived the procedure for further study. Tumors were measured 5 days after implantation. Two animals were treated with ganciclovir (20 mg/kg intraperitoneally daily) and two with saline daily. Tumor size was reassessed over a 16-day period. The two control tumors grew four- to twelve-fold. In contrast, the two treated with ganciclovir were smaller after the treatment than before.

Discussion

In these Examples, it is demonstrated that a retrovirus bearing the HSV-1-TK gene can be used to confer drug sensitivity on C6 glioma cell in culture and in vivo. This is the first retrovirus vector described bearing an active HSV-1-TK gene. It should have a number of potential uses. First, as described in detail below it should prove useful in selectively delivering this "killer" gene to tumor cells in the brain. A distinct advantage of the HSV-1-TK gene as compared to other toxic gene products is that it requires a second hit, treatment with a nucleoside analogue, to effect cell death. Further, cellular DNA replication is required for toxicity, so only dividing cells can be killed. Second, it should also be possible to use this retrovirus vector to incorporate the HSV-1-TK gene into genetically modified cells used for grafting (e.g., Rosenberg et al., *Science* 242:1575–1578 (1988). This would allow elimination of the grafted cells at a defined point in the experiment to evaluate the effects of these cells on the surrounding tissue. Third, this vector should prove useful for infecting progenitor embryonic cells to assess the nature and function of their progeny at later stages in development and throughout life. This vector, then, provides a tool to efficiently infect dividing cells in culture and in vivo and to insert into their genome a gene that can be used to kill them or their progeny at a defined time by application of a drug.

Primary brain tumors affect approximately 12,000 new patients in the United States each year. Twenty-five percent of primary brain tumors are glioblastomas which are only temporarily responsive or totally resistant to all forms of currently available therapy. Glioblastomas are almost universally fatal; cures remain anecdotal with only 3–5% of patients living five years beyond diagnosis. However, metastasis from glioblastoma is exceedingly rare. Glioblastomas kill from local growth, and, in many cases treated with radiation or chemotherapy, tumors recur within 2 centimeters of the original site. This finding suggests that some tumors may be treated with a local, targeted therapeutic approach. Various attempts at local therapies have been made including local hyperthermia (Salcman et al. , *J. Neuro. Oncol.* 1:225–236 (1983)), photodynamic therapy (Cheng et al., *Surg. Neurol.* 25:423–435 (1986)), focal irradiation with interstitial radioisotope implants (Gutin et al., *J. Neurosurg.* 67:864–873 (1987)). To date all of these techniques have met with only limited success and have had only a marginal impact on the treatment of glioblastoma.

Because of this limited success, retrovirus vectors were explored as a new avenue of potential therapy. Retroviruses exploit the fact that a malignant glioma is a dividing cell population within the population of non-dividing cells that compose the adult brain. Thus, retroviruses can offer a mode of selectivity for the brain tumor cells by delivering a toxic gene to them. Three toxic gene products have been used for ablation studies in transgenic mice (Bernstein and Breitman, *Mol. Biol. Med.* 6:523–530 (1989)). Two of these, ricin and diphtheria toxin, however, once released into the nervous system, could cause toxicity to brain, blood vessels, bone marrow or other tissues and cells containing them could not be aborted. For this reason, we have chosen to explore a strategy of tumor cell destruction that uses the HSV-1-TK gene, that is by itself not harmful, but which sensitizes cells to exogenously administered drugs, such as ganciclovir. In this way cell destruction can be controlled.

It has been demonstrated that the HSV-1-TK gene can be inserted into rat C6 glioma cells and that these cells are thereby made sensitive to ganciclovir. To demonstrate that C6 glioma cells expressing the HSV-1-TK gene can be killed in vivo, the subrenal capsule assay system in rats was used because it allows direct measurement of tumor volume, permits detection of small (<1 mm) volume changes, and because tumor vascularization is observable and allows for entry of parenterally-administered pharmaceutical agents. This model overcomes the problem of not being able to directly observe the size of an intracerebral tumor implant and the concerns about delivery of ganciclovir through an intact blood-brain barrier. With this subrenal capsule model, it is demonstrated that ganciclovir administered intraperitoneally will kill growing C6 glioma cells.

EXAMPLE 2

Glioblastomas represent approximately 30% of primary brain tumors in adults (Schoenberg, B. S., in *Oncology of the*

*Nervous System*, Walker, M. D., ed., Martinus Nijhoff, Boston, Mass. (1983)). They are invasive, malignant, and resistant to conventional treatment modalities, and therefore are considered virtually incurable (DeVita et al., *Cancer: Principles and Practice of Oncology*, vol. 2, 3rd ed., Lippincott Press, Philadelphia (1989); Shapiro et al., *J. Neurosurg.* 71:1–9 (1989); Onoyama et al., *Am. J. Roentgenol.* 126:481–492 (1976); Salazar et al., *Int. J. Rad. Oncol. Biol. Phys.* 5:1733–1740 (1979); Walker et al., *N. Engl. J. Med.* 303:1323–1329 (1980)). Recurrent disease often occurs within 2 cm of the original site (Hochberg et al., *Neurol.* 30:907–911 (1980)). With a median survival of less than a year and with only 5% of patients living after five years following diagnosis despite numerous multi-modal approaches (Mahaley et al., *J. Neurosurg.* 71:826–836 (1989); Schoenberg, B. S., in *Oncology of the Nervous System*, Walker, M. D. ed., Boston, Mass.: Martinus Nijhoff (1983); Kim et al., *J. Neurosurg.* (in press); Daumas-Duport et al., *Cancer* 62:2152–2165 (1988)), the need for novel treatment strategies cannot be overemphasized.

One strategy is the use of viral vectors to deliver foreign genes to modulate or to destroy glioma cells. Retroviruses provide a potential means of selectively infecting tumor cells in the adult brain, because they can only integrate into the genome of dividing cells and most adult brain cells are in a quiescent, non-receptive stage of cell growth (for review of retroviruses, see Varmus, H., *Science* 240:1427–1435 (1988)). These RNA viruses have been extensively used as vectors to deliver genes to dividing cells in culture and in embryos (for review, see Cepko, C., in *Neuromethods*, vol. 16, *Molecular Neurobiological Techniques*, Boulton et al., eds., The Humana Press, Clifton, N.J. (1989); Gilboa et al., *BioTechniques* 4:504–512 (1986)). Foreign genes and promoter elements can be inserted into plasmid DNA equivalents of the retroviral genome, which retain the packaging signal, psi. These plasmids are then transfected into packaging cell lines, which carry wild-type retroviral sequences lacking the psi element needed for packaging of their own RNA into virion particles (Cone et al., *Proc. Natl. Acad. Sci. USA* 81:6349–6353 (1984); Miller et al., *Mol. Cell. Biol.* 6:2895–2902 (1986); Mann et al., *Cell* 33:153–159 (1983)). The packaging line can insert the psi-bearing RNA encoded in the foreign gene-bearing retrovirus sequences into virion particles. These lines then release into the medium only replication-defective virions containing foreign gene sequences and no replication component virions. These replication-deficient virions can efficiently infect other dividing cells and insert the foreign genes into their genome.

A number of retroviral vectors have been developed for neuroscience applications, including ones bearing the genes for the histochemical marker, lacZ (Price et al., *Proc. Natl. Acad. Sci. USA* 84:156–160 (1987)), nerve growth factor (Wolf et al., *Mol. Biol. Med.* 5:43–59 (1988); Rosenberg et al., *Science* 242:1575–1578 (1988)), tyrosine hydroxylase (Wolff et al., *Proc. Natl. Acad. Sci. USA* 86:9011–9014 (1989); Horellou et al., *Proc. Natl. Acad. Sci. USA* 86:7233–7237 (1989); and other proteins (Fredericksen et al., *Neuron* 1:439–448 (1988); Cepko, C., in *Neuromethods*, vol. 16, *Molecular Neurobiological Techniques*, Boulton et al., eds., The Humana Press, Clifton, N.J. (1989); Cepko, C., *Ann. Rev. Neurosci.* 12:47–65 (1989)). Direct injection of lacZ bearing retroviruses (e.g., BAG) into embryonic tissues in vivo can yield gene delivery into neuroblasts and their differentiated daughter cells, as observed, for example, in epithelium, retina and cerebral cortex (Gray, G. E., *Proc. Natl. Acad. Sci. USA* 85:7356–7360 (1988); Turner et al., *Nature* (Lond.) 328:131–136 (1987); Walsh et al., *Science* 241:1342–1345 (1988); Luskin et al., *Neuron* 1:635–647 (1988)). No labelling of cells has been reported following injection of this type of vector into adult nervous tissue, as anticipated from the low mitotic index of these cells and the relatively short half-life of retrovirus particles (–4 hr in culture; Cepko, C., in *Neuromethods*, vol. 16, *Molecular Neurobiological Techniques*, Boulton et al., eds., The Humana Press, Clifton, N.J. (1989)). Several studies have shown that it is possible to use their retrovirus vectors for indirect "gene delivery" into adult rodent brains, by infecting dividing cells in culture and then grafting these genetically modified cells into the brain (Gage et al., *Neuroscience* 23:795–807 (1987). This procedure has been used with the lacZ vector to follow the fate of grafted rat C6 glioma cells and fibroblasts (Shimohama et al., *Mol. Brain Res.* 5:271–278 (1989)). Rat fibroblast lines infected with NGF and TH-bearing vectors, rat pheochromocytoma cells infected with the NGF vector, and a mouse pituitary line infected with a TH vector, have been used to deliver biologically active NGF and/or L-dopa and dopamine to regions of adult rat brain (Rosenberg et al., *Science* 242: 1575–1578 (1988); Wolff et al., *Proc. Natl. Acad. Sci. USA* 86:9011–9014 (1989); Horellou et al., *Eur. J. Neurosci.* 2:116–119 (1990)). Several new multipotent neural cell lines have been developed following infection with retrovirus vectors bearing myc and SV40T oncogenes (Snyder et al., *Neurosci. Abst.* 9:9 (1989); Lendahl et al., *Cell* 60:585–595 (1990); Ryder et al., *J. Neurobiol.* 21:356–375 (1990)).

A rodent glioma model was used to explore the possible use of retroviral vectors to deliver foreign genes to tumor cells in vivo. The BAG retrovirus vector was used to deliver the reporter gene lacZ into rat glioma cells implanted into the adult rat brain. The inventors have evaluated infection of endogenous brain cells and C6 glioma cells following direct injection of the BAG retrovirus or grafting of the psi 2-BAG packaging line which releases this virus vector. Cultured cells and tissue sections were evaluated by histochemical staining for bacterial beta-galactosidase, as an index of successful gene delivery, and by immunostaining for glial fibrillary acidic protein (GFAP) and S100, as a marker for glioma cells and astrocytes (Bignami et al., *Brain Res.* 43:429–435 (1972)), and for fibronectin, as a marker for the fibroblast-derived packaging line.

Materials and Methods

Cell culture, retrovirus infection and beta-galactosidase staining: The ecotropic retrovirus producer line, psi 2-BAG 2–14, obtained through M. Rosenberg (UCSD) from C. Cepko (Harvard Medical School) (Price et al., *Proc. Natl. Acad. Sci. USA* 84:156–160 (1987); Short et al., *Dev. Neurosci.* 12:34–45 (1990)), was grown in Dulbecco's modified Eagle's medium, 10% fetal calf serum, with 100 units/mL penicillin, 100 µg/mL streptomycin (D10 P/S), and 500 µg/mL of the neomycin analogue, G418. All cell culture materials were obtained from GIBCO. Virus was harvested by replacing the overlying media of nearly confluent cultures with a reduced volume of fresh media without G418. The conditioned media containing viral particles was removed 24–48 hr later, filtered through cellulose acetate membranes (pore size 0.45 µm, Nalgene) and stored at –70° C. The virus was titered as colony-forming units (cfu) on 3T3 cells in the presence of G418. Viral titers were $1-3\times 10^4$ cfu/mL. In some cases, viral stock was concentrated by centrifugation (Price et al., *Proc. Natl. Acad. Sci. USA* 84:156–160 (1987)) to $1-3\times 10^5$ cfu/mL.

Rat glioma cell line, C6 (Benda et al., *Science* 161:370–371 (1968)), was grown in D10 P/S. A C6-BAG line was prepared by infecting C6 glioma cells with the BAG vector and isolating single cell subclones under G418 selection. Cells were assayed for beta-galactosidase activity by histochemical analysis (Price et al., *Proc. Natl. Acad. Sci. USA* 84:156–160 (1987)). A subclone (C6-BAG B2-10) in which >99% of cells were beta-galactosidase positive after at least 6 passages was used in subsequent experiments at passage 2 or 3.

Cell grafting and retrovirus inoculation into adult rat brain: Adult Fischer rats weighing between 151–175 gms were anesthetized with an intraperitoneal injection of Equithesin (Short, C., *Principles and Practice of Veterinary Medicine*, Williams and Wilkins, Baltimore, Md. (1987)). Two to five animals were used for each experimental paradigm, and all experiments were carried out at least twice. Stereotactic coordinates for intracerebral injection were taken from a stereotactic atlas of the adult rat (Paxinos et al., in *Rat Brain in Stereotaxic Coordinates*, 2nd ed., Academic Press, New York (1986)). Cells and virus were injected with 8 μg/mL polybrene, or control medium using a 10 μl Hamilton syringe with a beveled 25 gauge needle. Injections (5 μl) were done over a 5 min interval, and the needle was kept in place for another 2 min prior to removal. Surgery was tolerated well by most animals; only a few animals died during anesthesia.

For grafting experiments, confluent cultures were rinsed with Dulbecco's phosphate-buffered saline (PBS) without $Ca^{++}$ and $Mg^{++}$ and incubated with 0.05% trypsin. Cells were dispensed in D10 and pelleted by centrifugation for 5 min at 1200×g. Cell pellets were resuspended in PBS and collected by centrifugation. Final cell suspensions were made at a density of $10^5$ cells/μl in complete PBS (PBS, which contains 1 μg/mL each $MgCl_2$ and $CaCl_2$, 0.1% glucose, and 5% rat serum (GIBCO)) and maintained at 4° C. until implantation.

Tissue preparation: Prior to perfusion, rats were anesthetized with Equithesin (Short, C., *Principles and Practice of Veterinary Medicine*, Williams and Wilkins, Baltimore, Md. (1987)). Perfusion was done via the ascending aorta with 50 mL of cold PBS containing 10,000 units/mL sodium heparin followed by 250 mL of cold 3% paraformaldehyde in PBS. After post fixation overnight at 4° C., brains were kept in increasing percentages (15, 20, 30) of sucrose at 4° C. until they sank. Brains were frozen on dry ice and kept at −80° C. until sectioning. Sections were either cut at 40 μm on a freezing microtome and kept at 4° C. in 0.5M Tris-HCl, pH 7.4, with 0.1% sodium azide or in 33% polyethylene glycol until staining; or cut at 10–15 μm on a cryostat and mounted directly onto gelatin-subbed (Fisher; 100 Bloom) slides and stored at 4° C. with desiccant until staining.

Histology: For beta-galactosidase histochemistry of tissues (and cells), a modification of the method of Turner and Cepko (Turner et al., *Nature* (London) 328:131–136 (1987)) was used. Briefly, 5-bromo-4-chloro-3-indolyl-B-D-galactoside (X-gal, Boehringer Mannheim) was prepared as a 4% stock solution in DMSO. Free-floating or mounted sections (or cells on tissue culture dishes) were incubated at 37° C. in a solution of PBS containing 2 μM $MgCl_2$, 35 μM $K_3Fe(CN)_6$, 35 μM $K_4Fe(CN)_6$, 0.01% sodium deoxycholate, and 0.02% NP40, pH 7.3; 0.1% X-gal was added just prior to incubation. After incubation overnight at 37° C., cultured cells were viewed directly and sections were rinsed with PBS, mounted on subbed slides and then counterstained with hematoxylin and eosin or neutral red. They were then rinsed in water, cleared in increasing concentrations of alcohol, and placed in water prior to coverslipping with aqueous mounting media, Crystal Mount (Biomedia) or placed in xylene prior to coverslipping with Permount (Fisher).

Some sections were also stained immunocytochemically to identify GFAP, S100, or fibronectin. The sections were rinsed in PBS, incubated for 30 min with blocking serum and then overnight at room temperature with the following antibodies: mouse monoclonal antibodies to human GFAP (Boehringer Mannheim), diluted 1:3; rabbit polyclonal antibody to bovine S100 (Dako) diluted 1:750; or mouse monoclonal antibody to human fibronectin (Cappell) diluted 1:80; all of which crossreact with their respective rat antigens. Antibodies were diluted in 10 μM phosphate buffer, pH 7.4, containing 0.9% NaCl, 0.25% TRITON-X-100 and 3% blocking serum. After thorough rinsing the sections were incubated for 2 hr with either biotinylated horse antimouse IgG, biotinylated goat antirabbit IgG, or rabbit antigoat IgG (Vectastain) diluted 1:200 in the buffer, followed by several rinses in PBS. The sections were then incubated for 30 min with a complex of avidin and biotinylated horseradish peroxidase (Vectastain, ABC elite kit) diluted 1.5:100 in the buffer. The peroxidase was visualized by reacting with 0.05% 3,3-diaminobenzidine tetrahydrochloride, 0.04% $NiCl_2$ and 0.01% $H_2O_2$ in 50 μM Tris-HCl, pH 7.3, for 5–10 min at room temperature. In some cases, sections were initially stained histochemically for beta-galactosidase activity and then immunostained for GFAP. In other cases, serial selections were stained alternatively for beta-galactosidase and GFAP or S100.

Results

Histochemical staining of psi 2-BAG cells in culture demonstrated nearly 100% positive staining for beta-galactosidase and no staining for GFAP, while most C6 cells stained positively for GFAP antigen, and all were negative for beta-galactosidase staining under the neutral conditions used. The ability of the psi 2-BAG cells to release BAG virus that could infect C6 cells was demonstrated by placing coverslips containing each of these two cell types at separate locations within the same culture dish. In the presence of psi 2-BAG cells, an ever-increasing percentage of cells on the coverslip bearing C6 cells stained positively for beta-galactosidase over a 96-hr period. Essentially, all cells on the glioma coverslip were also GFAP-positive. This is consistent with successful integration of the BAG virus released by psi 2-BAG cells into glioma cell genomes.

The efficiency of gene transfer to endogenous brain cells in vivo was tested by direct inoculation of 5 μl BAG retrovirus vector (90–900 cfu) into adult rat hippocampus or caudate. Control animals were similarly inoculated with complete PBS. Animals were sacrificed 7 days after injections. In the animals that received direct injection of virus, as well as in control animals, no cells positive for beta-galactosidase were seen within the parenchyma. Some sections from both groups revealed faint positive staining for beta-galactosidase within the choroid plexus, as noted previously (Shimohama et al., *Mol. Brain Res.* 5:271–278 (1989)). In these control sections, the stain was qualitatively different than in animals in which positively staining cells are present within the tumor mass (see below).

The efficiency of direct inoculation of tumor cells in the brain was tested at varying intervals between the time of the C6 cell implants and injection of the virus, under the assumption that the glioma cells might experience a growth lag after inoculation and thus not initially be in a stage of cell division appropriate for viral integration. The site of implantation and infection was the right frontal lobe. For simultaneous injections of glioma cells and BAG virus, C6 cells ($5 \times 10^5$) were suspended in 5 μl of viral stock (90–900 cfu). Other animals received delayed injections of virus stock into the previous site of the C6 cell implant. Five μl aliquots of virus stock were injected using the same stereotactic coordinates with which the C6 cells had been implanted 3 and 5 days previously. Control animals received grafts of C6 or C6-BAG cells without virus. All animals were sacrificed seven to 10 days after the last viral injection. In simultaneous injections of C6 cells and BAG virus, only a few tumor cells (less than 0.1%) stained for beta-galactosidase activity. In some cases, stained endothelial cells were also noted in vessels within and around the tumor mass. In the animals in which there was a delay between the tumor implant and the virus injection, again only a few positive cells were seen. There was no notable difference between the numbers of positively staining cells in animals that had experienced a delay before the viral injection versus those that received co-injections of C6 and BAG virus. Injections of C6 and C6BAG cells gave rise to tumors of similar size. In the C6 cell injections without virus, no blue cells were seen; in the C6BAG injections, all tumor cells were positive for beta-galactosidase, as noted previously (Shimohama et al., *Mol. Brain Res.* 5:271–278 (1989)).

To examine the fate of grafts of psi 2-BAG packaging cells, animals were injected with psi 2-BAG cells ($5 \times 10^5$ cells) into the right frontal lobe, and as a control, with an equal number of psi 2 cells into the left frontal lobe. Animals were sacrificed at varying times after implantation. After one day, a compact mass of beta-galactosidase positive cells was seen at the site of the right frontal injection. No positively stained cells were seen on the left side on day one, nor in either side in sections taken from animals sacrificed at days 5, 9, 14, and 21 following implantation. There was no evidence of tumor formation or other degenerative changes on the brain over this period.

The efficiency of in situ gene transfer of the lacZ gene into C6 by co-grafting of packaging line, psi 2-BAG, was then tested. For simultaneous co-grafts, the cell suspension contained a mixture of cells, in a ratio of one C6 cell to five psi 2-BAG cells. The site of implantation was again the right frontal lobe. For delayed injections, animals received implants of C6 cells ($2 \times 10^5$ cells) on day one, followed by injections of 5 µl of psi 2-BAG cells ($5 \times 10^5$ cells) on days 3 or 7. In all cases, animals were sacrificed seven days after psi 2-BAG cells had been implanted. Controls of psi 2-BAG and C6 alone were injected into other animals in parallel. In histochemically stained sections from animals that received simultaneous co-grafts of C6 and psi 2-BAG cells, both blue and non-blue cells were seen within the tumor mass. Some of these beta-galactosidase positive cells co-stained for GFAP or S100, indicating they were C6 glioma cells. There were also many GFAP or S100 positive cells within the tumor mass that were not positive for beta-galactosidase. Some of the other beta-galactosidase positive cells could be C6 cells with no or low expression of GFAP, or S100. In fact, in C6 cells implanted alone into the brain, only about half of the cells in the resulting tumor mass were S100-positive and even fewer were GFAP positive. Some of the beta-galactosidase positive cells could also be psi 2-BAG cells that might have survived longer within the tumor mass as compared to the brain parenchyma; however, immunostaining for fibronectin revealed no psi 2-BAG cells in co-grafts after 7 days. Examination of serial sections of these tumors revealed many sections without any beta-galactosidase-positive cells, and our best estimate is that about 1% of the cells in the tumor expressed the lacZ gene in animals receiving simultaneous injection of psi 2-BAG cells and C6 cells. In contrast, sections taken from animals that had received delayed injections of the packaging line into the tumor mass contained many cells positively stained for beta-galactosidase in all sections throughout the tumor, with up to 10% of cells being positive and most positive cells at the periphery of the tumor. Co-staining for the glia-specific antigen S100 and beta-galactosidase revealed that many of the cells within the tumor were glia-derived and some of these were also positive for beta-galactosidase activity. Tumor cells thus appear to have been more efficiently infected when the packaging line was grafted after establishment of tumor cells than when tumor and packaging cells were simultaneously injected. There did not appear to be any significant difference between animals in which the delay between injections was three days as opposed to seven days.

Discussion

In this study, we have demonstrated the efficacy of a replication-defective retroviral vector in delivering the reporter gene, lacZ, to rat glioma cells in culture and the rat brain. In culture, the BAG retrovirus vector released from psi 2-BAG cells successfully infected C6 cells in the same dish, as demonstrated by staining for beta-galactosidase activity. The morphology and immunoreactivity to GFAP confirmed the identity of the beta-galactosidase positive cells as glioma cells. The efficiency of transfer of the lacZ gene to endogenous brain cells or to C6 cells in vivo was then compared by two techniques: direct injection of BAG virus or grafting of the packaging line that releases the virus. The highest efficiency in vivo was obtained by grafting of the retrovirus packaging line into an established bed of C6 tumor cells.

Initial attempts to deliver the reporter gene by direct injection of virus into the parenchyma of a normal adult rat brain produced essentially no beta-galactosidase-positive cells. In these animals, as well as in controls inoculated with complete PBS, hint positive staining was seen in the choroid plexus, but not in the parenchyma. This endogenous positive staining of lysosomal beta-galactosidase has been previously reported (Shimohama et al., *Mol. Brain Res.* 5:271–278 (1989)), and was masked when sections were counterstained with neutral red. The unsuccessful direct gene delivery by the viral vector was not surprising since the majority of cells in adult rats, even in young postnatal animals, are post-mitotic, and cell division is needed for retroviral integration. The site of inoculation, the hippocampus, was chosen to enhance the likelihood of successful integration, since cells in this region are the last to stop dividing after birth (Das et al., *Brain Research* 22:122–127 (1970)). In animals inoculated with the BAG virus either simultaneously with glioma cells or after a delay following the glioma implant, only a few isolated tumor cells were successfully infected. This presumably reflects the relatively short half-life of the retrovirus in vivo and the state of division of the glioma cells. Of the few beta-galactosidase positive cells, most were found at the edges of the tumor where there is thought to be highest mitotic activity. Occasionally stained endothelial cells were observed, which would be expected since endothelial cells continue to divide within the blood vessels of the brain, especially in a vascularized tumor bed.

Both viral titer and the volume of the inoculum represent significant limitations to attaining a higher degree of successful integration using direct virus injection. Attempts to increase viral titer by centrifugation only increased the titer by 10- to 100-fold. When inoculating a glial tumor, which began with about $10^5$ cells, with 5 µl of a retrovirus stock of $10^4$–$10^6$ cfu/mL, the ratio of virus to cell is much less than one to one (multiplicity of infection MOI) $\leq 0.01$). In our hands, the efficiency of infection of rapidly dividing C6 cells in culture with the BAG retroviral vector at an MOI of 3 is approximately 30%. Thus, it is not surprising that direct inoculation of the tumor was inefficient in vivo.

Implantation of the packaging line appears to overcome some of the limitations of direct inoculation by releasing the virus within the tumor over a prolonged period. This Example demonstrates that co-grafting of the packaging line, psi 2-BAG and glioma cells, serves to deliver the reporter gene, lacZ, to these tumor cells more efficiently than direct viral inoculation. The efficiency was greater in animals implanted with glioma cells 3 or 7 days prior to implantation of psi 2-BAG cells as compared to simultaneous grafting of these two cell types. Histochemical analyses of sections taken from the brains of animals, which had received delayed injections, showed that large areas of the tumor were successfully infected. The brains were examined one week after the psi 2-BAG implantation, because in a separate experiment when psi 2-BAG cells were implanted alone, they were undetectable five days later. Further, immunostaining of co-grafts after 7 days revealed no fibronectin positive cells. This suggests either that the psi 2-BAG graft had been immune rejected because of a difference in rat strains or that the retroviral encoded gene, if present, was no longer being expressed (Palmer et al., personal communication). By immunocytochemistry, we have established that some of the cells within the tumor stain for both beta-galactosidase activity and GFAP or S100 antigens, confirming successful infection of glioma cells by the BAG virus released from the psi 2-BAG cells. However, there are GFAP- and S100-positive cells within the tumor that are beta-galactosidase negative, suggesting incomplete infection of tumor cells.

Several means can be envisioned to increase the efficiency of infection of glioma cells in the brain by co-grafting of retrovirus packaging lines. One way would be to carry out a series of injections of the packaging line to increase the number of cells releasing virus within the tumor bed over a longer period. Another way to increase the amount and duration of retrovirus release would be to develop a packaging line that was immune compatible with the host and thus would survive longer following grafting. Release to a larger area including the brain parenchyma surrounding the tumor might also be achieved by using an astrocyte-derived packaging line. Grafted newborn and embryonic astrocytes have been shown to be able to migrate up to 5 mm from their original site of injection and may be better than fibroblasts in reaching infiltrating glial tumor cells (Jacque et al., *Dev. Neurosci.* 8:142–149 (1986); Zhou et al., *J. Comp. Neurol.* 292:320–330 (1990); Hatton et al., *Soc. for Neurosci. Abstracts* 15:1369 (1989)). Additionally, a glial-derived packaging line derived from glia that are endogenous brain cells may have enhanced survival and may be more responsive to in situ cues. In the case of spontaneous brain tumors, one could envision a scheme in which the tumor mass was removed, leaving some tumor cells behind, and the packaging line grafted directly into the lesion. This would serve to increase the number of packaging cells that could be grafted in and the ratio of packaging cells to tumor cells, and hence increase the ability to infect tumor cells.

This Example represents a model system that could be used to deliver genes with therapeutic potential to malignant glial tumors of the central nervous system (CNS), which at this time continue to pose a unique challenge in oncology. Complete surgical extirpation is impossible, since the tumor cells infiltrate within the normal brain. Radiation therapy is limited by the sensitivity of the normal brain to radiation damage. Chemotherapy is hampered by the presence of a blood brain barrier decreasing the usefulness of agents unable to cross this barrier to reach infiltrating tumor cells. Retroviruses represent potential therapeutic agents that can confer genetic susceptibility onto tumor cells. One example would be a retrovirus packaging line that releases virions containing the herpes simplex virus thymidine kinase (HSV-TK) gene (Moolten et al., *J. Natl. Cancer Inst.* 82:297–300 (1990)). When integrated into the mammalian cell genome, the HSV-TK gene confers sensitivity to chemotherapeutic agents, such as the nucleoside analogues, acyclovir, ganciclovir, and FIAU. Cell culture studies have shown that C6 glioma cells and other cells infected with this retrovirus are killed at concentrations of ganciclovir 100-fold less than those required to kill uninfected cells (Moolten et al., *J. Natl. Cancer Inst.* 82:297–300 (1990)).

It may also be possible to kill C6 glioma cells by subsequent co-grafting of the HSV-TK virus packaging line and treatment of animals with a nucleoside analogue. Further, tumor vessels may be an additional target for a proposed killing system using the HSV-TK gene.

EXAMPLE 3

Retroviral vectors can be used to transfer genes into the genome of dividing cells. In order to increase the efficiency of gene delivery and killing effect of ganciclovir, a new packaging line (C6VIK-WT) was developed by infecting C6VIK cells with an ecotropic wild-type retrovirus (MoMLV). See Mann et al., *Cell* 33:153–159 (1983); Price et al., *Proc. Natl. Acad. Sci. USA* 84:156–160 (1987); and Cepko, C., in *Neuromethods, vol. 16, Molecular Neurobiological Techniques*, Boulton et al., eds., The Humana Press, Clifton, N.J. (1989), pp. 177–219. Because tumor cells can migrate deep into brain parenchyme, they should be able to deliver the vector to tumor cells away from the tumor mass. In culture, 50% of C6VIK-WT cells were killed at 0.024 μM GCV, while it took 7.3 μM GCV to kill 50% of C6VIK cells. This suggests that C6VIK-WT cells may have more HSV-TK activity than C6VIK due to multiple integrations of the HSV-TK gene or to an increased sensitivity of C6VIK-WT cells to GCV toxic products. When C6VIK and C6VIK-WT were cultured with C6BAG cells (labelled with the lacZ gene and thus detectable by beta-galactosidase histochemistry), following GCV treatment substantially more C6BAG cells were killed when co-cultured with C6VIK-WT than with C6VIK cells. Presumably C6VIK-WT cells produce both wild-type retrovirus and retrovirus vectors containing the HSV-TK gene (neither of which are produced by C6VIK cells) and death of C6BAG cells might be mediated by retrovirus infection and/or self-generated GCV toxic products. In vivo GCV treatment caused regression of tumors in most nude mice inoculated subcutaneously with C6VIK-WT cells, or with C6VIK-WT and C6BAG cells simultaneously but not with C6BAG cells alone. These findings suggest the efficiency of retrovirus-mediated gene delivery and the sensitivity to toxic agents of tumor cells can be increased using helper virus, which turns cells infected with retrovirus vectors into packaging cell lines.

The use of retroviral vectors for gene delivery need not be restricted to gene systems designed for tumor destruction. Delivery of genes involved in tumorigenesis or tumor modulation may also be a useful strategy to explore. The loss of heterozygosity for DNA markers on chromosomes 17, 10 and, less commonly, chromosome 22, in glial tumors suggests that minor suppressor genes reside in these chromosomal regions (Bigner et al., *Hereditas* 101:103–113 (1984); Bigner et al., *Cancer Res.* 88:405–411 (1988); James et al., *Cancer Res.* 48:5546–5551 (1988); El-Azouzi et al., *Proc. Natl. Acad. Sci. USA* 86:7186–7190 (1989)). Restoration of retinoblastoma gene function has been shown to inhibit growth of retinoblastoma and osteosarcoma cells in culture (Huang et al., *Science* 242:1563–1566 (1988)).

EXAMPLE 4

In order to transfer chemosensitivity to recipient tumor cells at levels which are therapeutically useful, a C6VIK glioma line infected with wild type Moloney murine leukemia virus (WT MoMLV) was used as the vector-producing or "donor" cell line. Glioma cells, being neoplastic, persist longer in vivo and intermingle with other tumor cells. Further, wild type helper virus mediates a more widespread infection of "recipient" tumor cells with the VIK vector than could be achieved with a defective helper. The infected cell line (C6BVIKWT) releases both replication-defective VIK vector and wild type virus. C6BVIKWT cells sensitize recipient C6BAG tumor cells to ganciclovir treatment, both in culture and in vivo.

Methods

Retrovirus: The VIK retrovirus vector contains a 2.8 kb BamHI fragment containing the full coding sequence and 2 kb of the 3' noncoding region (including the poly A addition site) of the HSV-TK gene cloned into the BamHI site of the retrovirus plasmid, pLRNL, (Ezzedine et al., *New Biol.* 3:608–614, 1991). The BAG retrovirus vector bears lacZ transcribed from the 5' LTR and the neo® gene transcribed from an SV40 promoter-enhancer element (Price et al., *Proc. Natl. Acad. Sci. USA* 84:156–160, 1987). The producer cell line "sup", which releases infectious wild type MoMLV, was used (Reik et al., *Proc. Natl. Acad. Sci. USA* 82:1141–1145, 1985).

Cell Culture and Infection: The rat C6 glioma line was derived from a nitrosomethylurea-induced brain tumor (Benda et al., *Science* 161:370–371, 1969). The C6 BAG cell line was generated by infecting C6 glioma cells (Benda et al., 1969) with the BAG retrovirus and cloning under selection in G418 (see below); the cells in this clone uniformly express *E. coli* beta-galactosidase (Shimohama et al., *Mol. Brain. Res.* 5: 271–278, 1989).

The C6BU1 cell line was derived from rat C6 glioma cells by mutagenesis and selection in bromodeoxyuridine for loss of endogenous TK activity (Amano et al., *Exp. Cell. Res* 85:399–408, 1974). C6BU1 cells were infected with either the retrovirus vector, VIK (Ezzedine et al., *New Biol.* 3:608–614, 1991), or the retrovirus vector, BAG (Price et al., *Proc. Natl. Acad. Sci. USA* 84: 156–160, 1987), produced by psi-2 producer lines, and were cloned under selection in the presence of HAT (10 mM sodium hypoxanthine, 40 µM aminopterin and 116 mM thymidine, GIBCO) or the neomycin analogue, G418 (1 mg/mL, GIBCO), respectively, to yield lines C6BVIK and C6BBAG. C6BU1 and C6VIK cells were infected with wild type MoMLV virus (WT) released from the producer line, "sup", to produce C6BWT and C6VIKWT cells, respectively. Other cell lines used in the study were NIH3T3 and TK-negative NIH3T3.

All cell lines were grown in Dulbecco's modified Eagle medium (320-1965, GIBCO) containing 10% fetal bovine serum (GIBCO), 100 units/mL penicillin, and 100 µg/mL streptomycin. All infections were done in the presence of polybrene (Sigma), as described (Mann et al., *Cell* 33:153–159 (1983).

Viral stock was obtained from cultures grown to near 80% confluency in selection medium, then maintained in media lacking G418 or HAT for 24 hrs. Culture medium was removed, filtered through a 0.45 µm filter (Nalgene) and stored at −70° C. (viral stock).

Viral titers of the producer cell lines were measured by infecting NIH3T3 (TK-) or NIH3T3 cells with virus stock and determining the number of HAT-resistant or G418-resistant cells, respectively, per unit volume of stock. Culture medium from C6V1K cells, at the same passage as used here, was shown to be absent of helper virus activity (Ezzedine et al., *New Biol.* 3:608–614 (1991)).

Ganciclovir Sensitivity Assays in Culture: To measure the sensitivity of isolated cells, cells were plated in 24-well plates at a density of $10^4$ cells per well. The next day, medium was replaced with medium containing ganciclovir (Cytovene, Burroughs Wellcome) at varying concentrations (0–1 µM) in quadruplicate. Four days later, cells were harvested using trypsin and counted using a cell counter (Coulter Electronics Ltd., Luton, United Kingdom). Cell growth is expressed as the percentage of cells compared to the number of cells without treatment (100%).

To measure the ganciclovir sensitivity of colony formation, cells were plated in duplicate at a density of 500 cells per 25 cm$^2$ culture flask. Seven days later, ganciclovir was added at various concentrations (0, 0.1, 0.5, 1, 10, 50, 100, 300 µM) in quadruplicate and incubation was for 9–12 days, with medium changes every 3–5 days. Cells were then fixed with 100% methanol, and stained with Giemsa (Freshney, R. I., "Culture of Animal Cells," in: *A Manual of Basic Techniques*, 2d ed., New York, Alan R. Liss, Inc., pp. 170–171 (1987)), and colonies ≧2 mm in diameter were counted.

Co-Culture Experiments: For delayed co-culture experiments, C6BAG or C6BBAG cells (recipients) were plated at a cell density of $10^3$ cells per 25 cm$^2$ culture flask in duplicate and cultured for seven days, at which time sampling showed their numbers had increased to 5×$10^4$ cells per flask. Donor C6VIK or C6VIKWT cells were then added to the cultures at a ratio of 1:2 (5×$10^4$ recipient cells: $10^5$ donor cells). Control cultures consisted of C6BAG or C6BBAG cells alone, or C6BA6 or C6BBAG cells co-plated with "donor" C6BU1 or C6BWT cells, after delay, as above. After 10 days, ganciclovir was added at varying concentrations (0–300 µM) and cells were incubated for another 9–12 days with the drug. Cells were then fixed with 0.5% glutaraldehyde and stained histochemically for beta-galactosidase activity, as described (Price et al., *Proc. Natl. Acad. Sci. USA* 84:1141–1145 (1987)), and colonies were counted.

For simultaneous co-culture experiments, $10^3$ recipient cells, C6BAG or C6BBAG were plated together with $10^5$ C6VIK or C6VIKWT donor cells, in duplicate. Controls were C6BAG or C6BBAG cells co-plated with C6BU1 cells at a similar ratio (1:100). After seven days, ganciclovir was added at varying concentrations (0 to 300 µM) and culture was processed as above. To assess the effects of the ratio of the donor cells to recipient cells, simultaneous co-culture experiments were also done varying the ratio of the donor cell, C6VIKWT, to the recipient cell, C6BAG, from 0.1 to 100.

Toxicity Assay: To assay for the generation of a diffusible cytotoxin from donor cells infected with wild type virus and/or toxic metabolites from cells bearing the HSV-TK gene treated with ganciclovir, medium was harvested from co-cultures of C6BAG and C6VIKWT cells before and during treatment with 300 µM ganciclovir for seven days. Control medium was harvested from C6BAG cells. The media were filtered (as above) and assayed for cytotoxicity to naive C6BU1 cells plated at $10^4$ cells per 25 cm$^2$ culture flask in duplicate. Volumes of media ranged from 0.1 to 1 mL in a total volume of 4 mL/flask. After seven days, the cells were fixed with 100% methanol and Giemsa-stained, and colonies were counted.

Ganciclovir Sensitivity of Tumors In Vivo: C6VIKWT cells ($5 \times 10^5$ cells in 200 μl media) were injected subcutaneously into the flanks of female nude mice (NCr/Sed, nu/nu; MGH breeding colony) (Ezzedine et al., *New Biol.* 3:608–614 (1991)). There were three treatment groups; 25 mg/kg ganciclovir intraperitoneally twice a day for 14 days, n=5; 25 mg/kg ganciclovir intraperitoneally once a day for 14 days, n=4; and 12.5 mg/kg ganciclovir intraperitoneally twice a day for 14 days, n=4. Ganciclovir therapy was begun when tumor size reached 1 cm in diameter as measured by calipers, by intraperitoneal injections up to 25 mg/kg daily for 14 days. The control group received phosphate buffered saline (PBS, 310-4200AJ, GIBCO) intraperitoneally in similar dosing schedules for 14 days. Tumor volumes were measured biweekly during treatment over a 24 day period, and were expressed as a percentage compared to the volume at the time treatment was begun.

Sequential injections of $10^5$ C6BAG cells followed immediately by $10^6$ C6BU1 cells, C6VIK cells, or C6VIKWT cells at the same injection site, were carried out as above using 20 animals for each combination. After the tumors had reached 1 cm in diameter, ganciclovir treatment was begun for 14 days, 25 mg/kg twice a day intraperitoneally in half of each group, with the other half receiving PBS intraperitoneally as a control. Tumor volume was assessed as the percentage increase over the volume at the beginning of treatment through 17 days.

Results

1. Culture Studies

Figure 1:
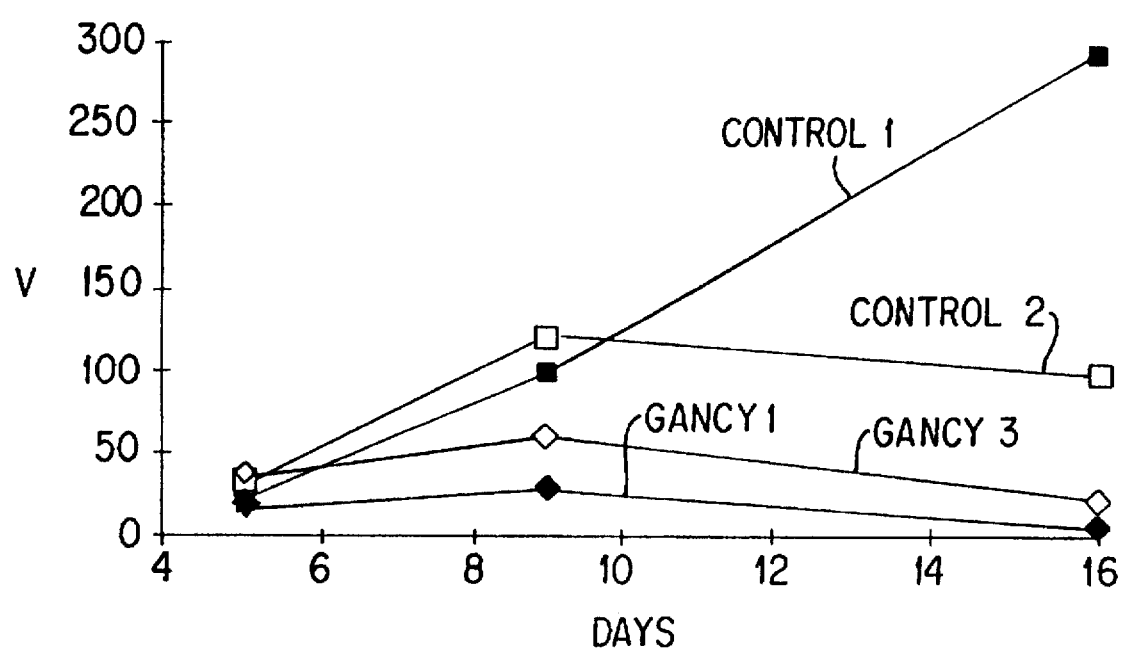
FIG. 1 is a graph depicting an in vivo study of ganciclovir.
Figure 2:
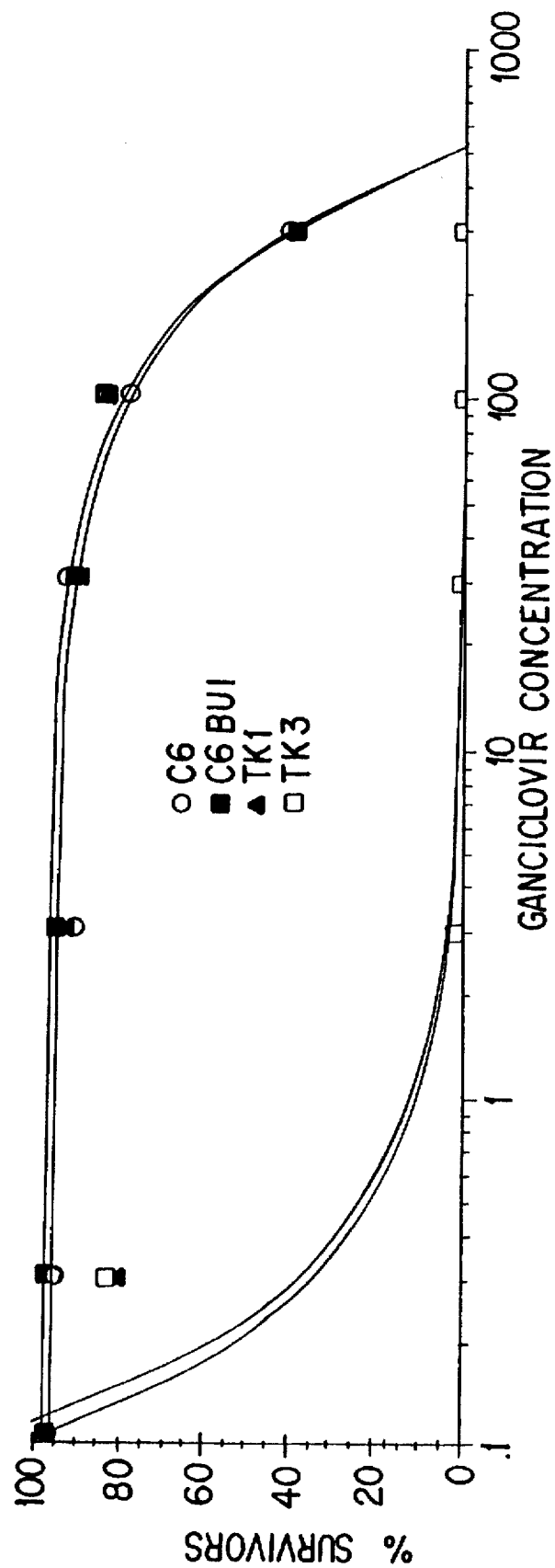
FIG. 2 is a graph depicting the ganciclovir sensitivity assay.
Figure 3:
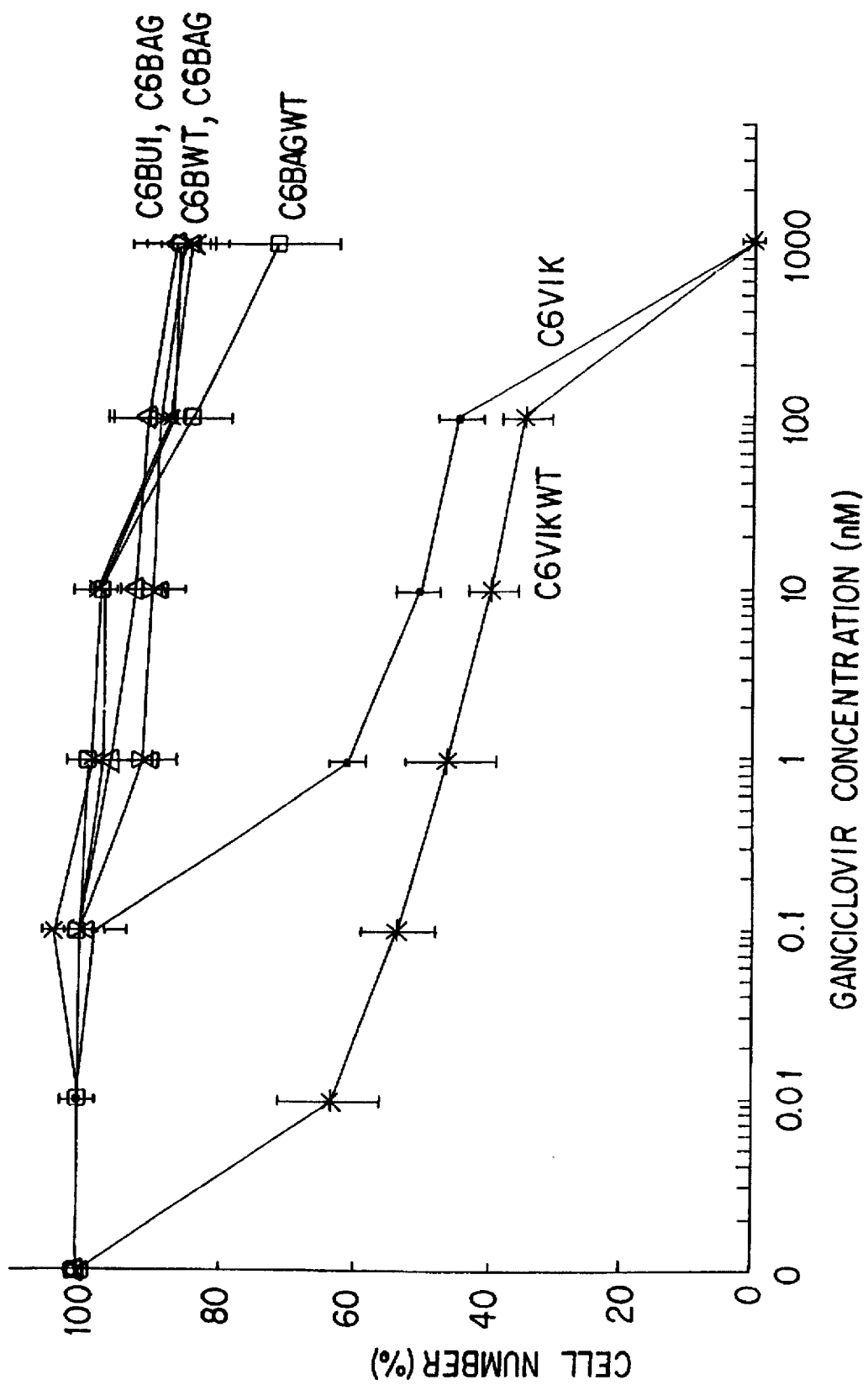
FIG. 3 is a graph depicting ganciclovir sensitivity of C6-derived cells in culture. Growth inhibition of C6VIK, C6VIKWT, C6BU1, C6BAG, C6BBAG, C6BAGWT and C6BWT cells by ganciclovir when treatment was begun the day after plating. Cell numbers were determined four days after plating. Cell growth is expressed as the percentage of cells with treatment compared to the number of cells without treatment (100%). Bars indicate standard error of the mean.
Figure 4:
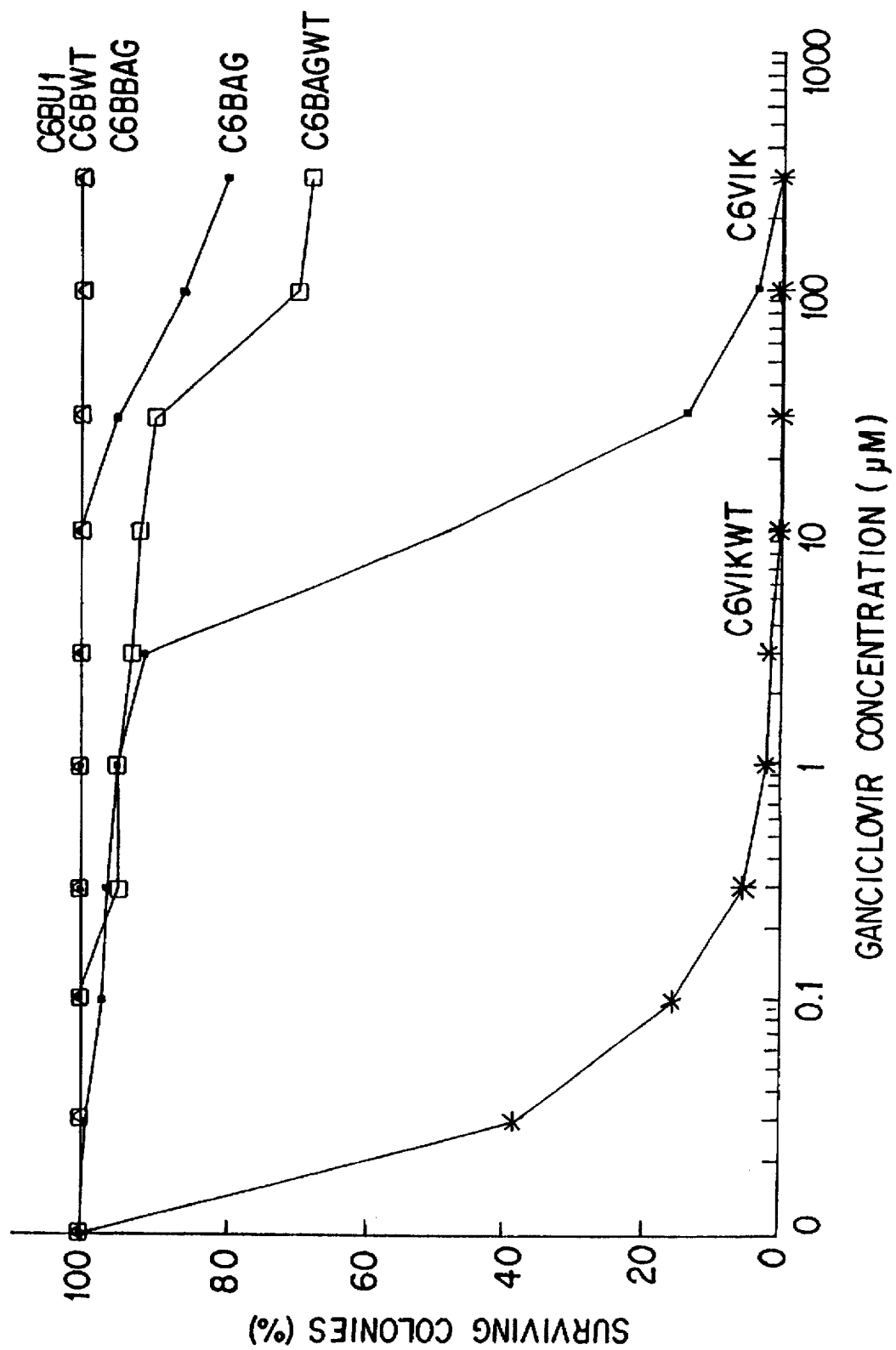
FIG. 4 is a graph depicting ganciclovir sensitivity of C6-derived cells in culture. Ganciclovir treatment was begun 7 days after plating these same cell lines to determine the ganciclovir sensitivity of colony formation. Ganciclovir treatment was continued for 9–12 days and then colonies were stained and counted. Survival colonies are expressed as a percentage compared to the number of colonies without treatment (100%). Studies were done in triplicate with less than 0.5% variability.

Ganciclovir Sensitivity: The dose dependent sensitivity of various cell lines to ganciclovir was evaluated by cell proliferation and colony formation assays. Of the two HSV-TK bearing lines, C6VIKWT cells were more sensitive to ganciclovir than C6VIK cells in the proliferation assay (FIG. 3). Fifty percent inhibition of growth over a four-day period was seen for C6VIK cells at 10 nM, and for C6VIKWT cells was 0.3 nM. No substantial inhibition of growth was found for the C6BU1 (HSV-TK negative), C6BAG, C6BWT, C6BBAG or C6BAGWT cells even at 1000 nM ganciclovir. For colony survival, drug therapy was begun seven days after plating, then nine to 12 days later surviving colonies were counted. The cell line C6VIKWT, was 300-fold more sensitive to the toxic effect of ganciclovir than the parental line C6VIK, when evaluated at the level of 50% surviving colonies (FIG. 4). The much greater sensitivity of C6VIKWT as compared to C6VIK cells is related to the presence of the HSV-TK gene since there was no significant difference in sensitivity of C6BAGWT and C6BWT lines, which had been similarly infected with the wild type virus, when compared with uninfected C6BAG and C6BU1 cells (FIG. 4).

Figure 5:
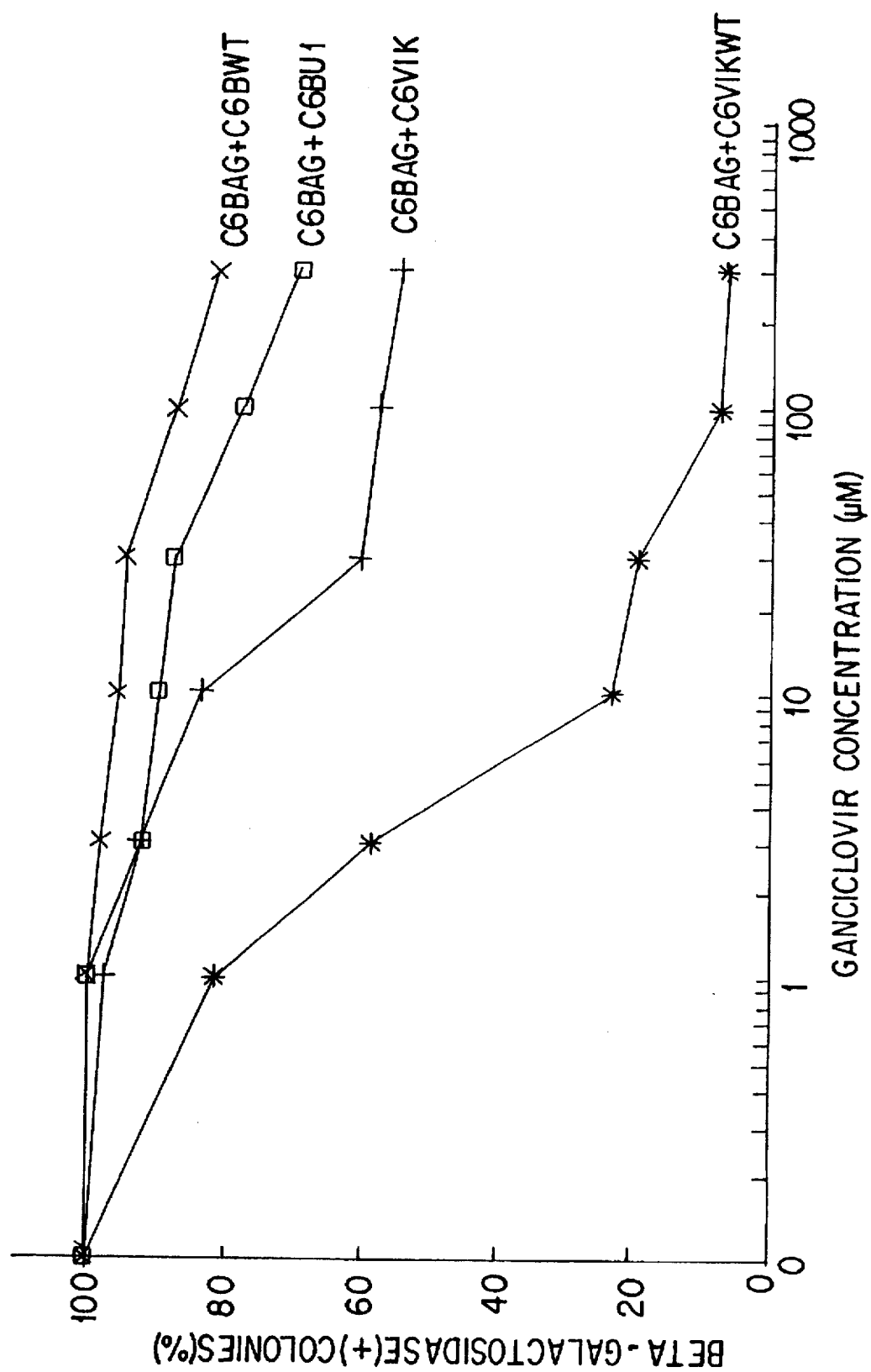
FIG. 5 is a graph depicting ganciclovir sensitivity of C6BAG cells after delayed co-culturing with other C6-derived lines. Seven days after C6BAG cells recipients were plated, C6BU1, C6BWT, C6VIK, or C6VIKWT cells (donors) were plated with them at a ratio of 1:2. Ganciclovir treatment was begun three days later and continued for 9–12 days. Cells were then stained for beta-galactosidase activity and only positive colonies were counted. Colony numbers are expressed as a percentage of those seen for parallel cultures without ganciclovir. Only survival of beta-galactosidase-positive colonies was scored. Studies were done in triplicate with less than 0.5% variability.
Figure 6:
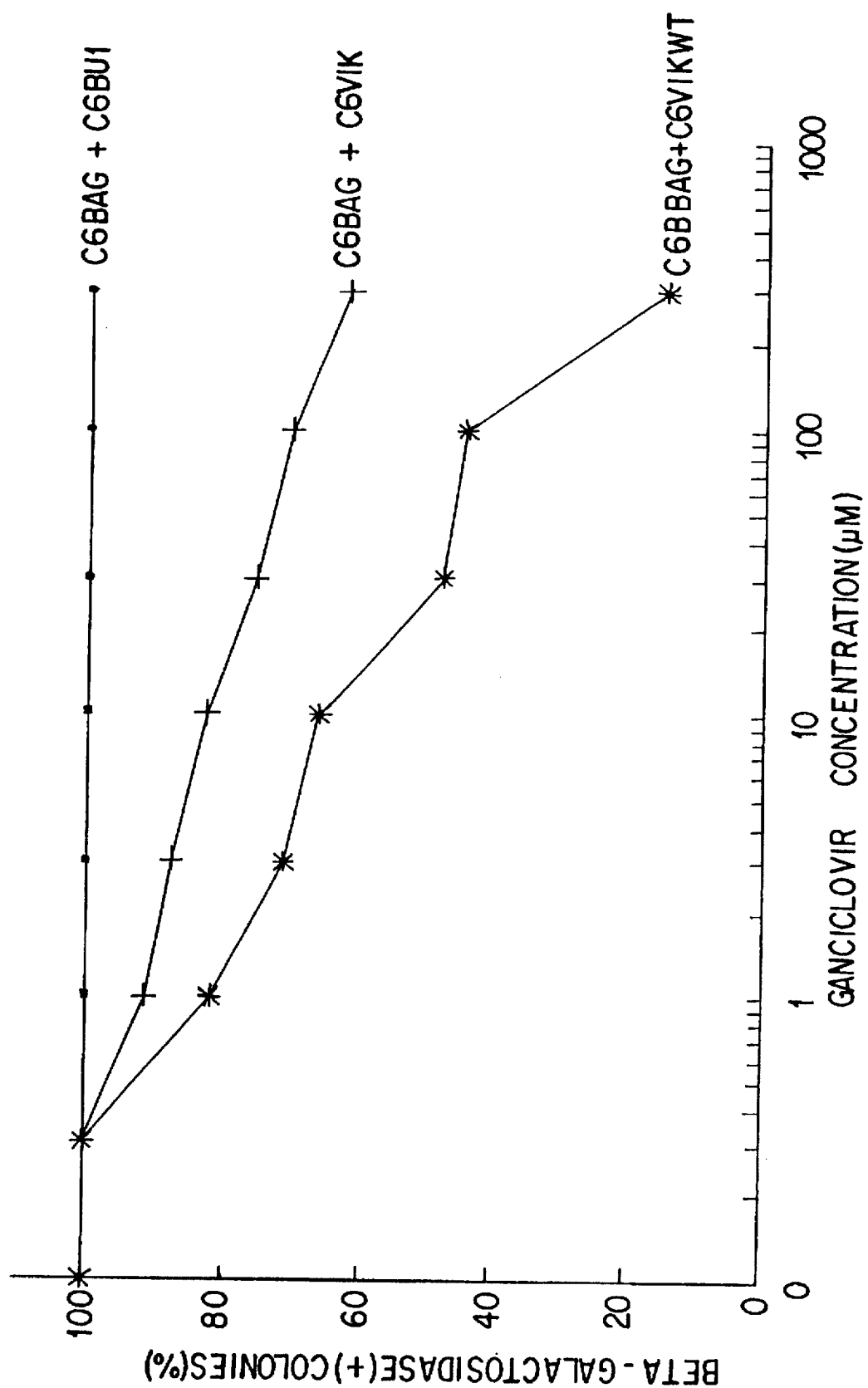
FIG. 6 is a graph depicting ganciclovir sensitivity of C6BAG cells after delayed co-culturing with other C6-derived lines. This analysis was carried out as in FIG. 5 except C6BBAG, which lack endogenous TK, were used instead of C6BAG. Studies were done in triplicate with less than 0.5% variability.

Co-culture experiments were undertaken to determine whether ganciclovir-sensitive "donor" cells carrying the HSV-TK gene, could transfer drug sensitivity to HSV-TK negative "recipient" cells. Sensitization of recipient cells was observed following co-culture with either C6VIK or C6VIKWT (in a ratio of 1:2) (FIG. 5), but the latter was much more effective, resulting in almost complete ablation of the recipient cells, as assessed by the percentage of surviving beta-galactosidase-positive colonies. In a parallel, control experiment, when C6BAG cells were co-cultured with either C6BU1 or C6BWT cells (ratio 1:2), no significant sensitization to ganciclovir was observed. In a similar experiment, recipient C6BBAG cells demonstrated a comparable higher ganciclovir sensitivity when co-cultured with C6VIKWT cells as compared with C6VIK cells. However, the dose of ganciclovir needed to inhibit colony formation by C6BBAG cells was higher than for C6BAG cells (FIG. 6). For example, in co-cultures with C6VIKWT cells, 50% of C6BAG cells grew when in the presence of 3 μM ganciclovir, while 50% of C6BBAG cells grew at 30 μM ganciclovir. This higher sensitivity of C6BAG cells is due to their endogenous thymidine kinase activity, which is lacking in C6BBAG cells.

In co-culture experiments in which recipient C6BAG cells (FIG. 7) or C6BBAG cells (FIG. 8) were plated simultaneously with donor C6VIK or C6VIKWT cells (in a ratio of 1:100), greater sensitization of C6BAG cells to ganciclovir was seen in the presence of C6VIKWT cells as compared to C6VIK cells (FIG. 7). In these simultaneously plated co-cultures, the ganciclovir sensitivity of C6BAG cells appeared to be 10-fold greater than in delayed co-cultures. This may reflect the ratio of donor cells to recipient cells which was 50-fold greater in the simultaneous experiments. The effect of cell ratios was investigated by changing the proportion of donor cells (C6VIKWT) to recipient cells (C6BAG). At 100 μM ganciclovir in ratios of 0.1 and 1, there was no significant difference in the ganciclovir sensitivity of C6BAG cells as compared to cultures of C6BAG cells alone. At ratios of 10 and 100 there was a "dose response" curve of greater sensitivity to 100 μM ganciclovir of C6BAG cells with increasing numbers of C6VIKWT cells (FIG. 9). In subsequent in vivo experiments, a ratio of 10:1 was used for donor cells: recipient cells.

Assays of Gene Transfer: Medium from the wild type-infected line, C6VIKWT, was used to titrate transfer of the HSV-TK gene to NIH3T3 (TK⁻) cells and the neo® gene to NIH3T3 cells. The titer for G418 resistance was $5 \times 10^5$ cfu/mL on NIH3T3 cells. The titer of TK gene transfer as assessed by HAT resistance of LMTK⁻ cells was $3.2 \times 10^3$ cfu/mL. The higher titer of vector yielding G418 resistance, as compared to that for HAT resistance, reflects the greater sensitivity of this assay and/or greater expression of the neo® gene. This high titer indicates that the WT virus, which was not assayed directly, was actually replicating in C6VIKWT cells.

Toxicity Assay: Conditioned medium obtained from C6VIKWT cultures, before and during 300 μM ganciclovir treatment, was assayed on naive C6BU1 cells by the colony survival method. No apparent growth inhibition was noted, indicating that if toxic substances were released into the medium, they were not effective against these naive cells.

2. In Vivo Experiments

Ganciclovir Sensitivity of C6VIKWT: Subcutaneous injection of C6VIKWT cells into the flank of nude mice produced tumor masses which increased in volume on average over 27-fold during a 24 day period (FIG. 10). The growth rate was slower for cells, which were infected with wild type virus, than that observed previously for uninfected C6VIK cells (Ezzedine et at., *New Biol.* 3:608–614 (1991)). Treatment of C6VIKWT tumors with ganciclovir for 14 days, beginning after the tumor had reached a size of 1 cm in diameter, inhibited subsequent growth completely (FIG. 10). There was no apparent difference in inhibition kinetics in the three ganciclovir regimens tested; 50 mg/kg/day ganciclovir in two injections per day regimen, 50 mg/kg/day in one injection per day regimen, or 25 mg/kg/day in two injections per day (data not shown). In all 13 animals in which ganciclovir treatment was stopped after 14 days, slow regrowth of tumors occurred over the next two weeks (data not shown).

When different combinations of cells were tested, there was no significant difference in the volume of tumors in the animals receiving both C6BAG and C6BU1 cells, or C6BAG and C6VIK cells during 14 days treatment with PBS (FIG. 11). Tumors that represented a combination of C6BAG and C6VIKWT cells (1:10); however, were smaller at all time points over this period. In parallel, animals bearing such tumors received a 14 day course of ganciclovir treatment. There was a significant decrease in the tumor volume of those composed of C6BAG and C6VIK cells as compared to those containing C6BAG and C6BU1 cells over this period, and an even greater decrease in the size of C6BAG and C6VIKWT tumors (FIG. 12). Histologic examination of the latter tumors at day 17 revealed extensive necrosis and it was not possible to determine the identity of any remaining tumor cells. Again, there was a slow regrowth of this latter tumor cell combination over a subsequent two-week period, and this regrowth was not blocked by another two weeks of ganciclovir therapy. The surviving tumor might consist of C6BAG cells which did not receive the HSV-TK gene or C6-derived cells bearing this gene in which its expression was "shut-off."

Discussion

It has been demonstrated that the efficacy of retrovirus-mediated gene transfer and the chemosensitivity to the nucleoside analogue, ganciclovir, can be increased in glioma cells by combined infection with a retrovirus vector containing the HSV-TK gene and wild type MoMLV. This treatment was effective at killing tumor cells both in culture and in vivo.

Gene therapy is a new and potentially powerful approach to treatment of cancer and other disorders (Gansbacher et at., *Cancer Res.* 50:7820–7825 (1990); Rosenberg, *Cancer Res.* 51:5074s–5079s (1991); Gilboa, E., "Retroviral Gene Transfer: Applications to Human Therapy", in: *Biology of Hematopoiesis*, Wiley-Liss Inc., pp. 301–311 (1990)). Tumor cells infected with retrovirus vectors bearing the HSV-TK gene can be eradicated by administration of ganciclovir (Moolten, *Cancer Res.* 46:5276–5281 (1986); Moolten et al., *Human Gene Ther.* 1:125–134 (1990); Moolten and Wells, *J. Natl. Cancer Inst.* 82:297–300 (1990); Plautz et al., *New Biol.* 3:709–715 (1991)). Retrovirus infection requires cell division, and the target cells in the normal adult CNS are reported to be glia and endothelial cells (Kay et al., *Proc. Natl. Acad. Sci. USA* 88:1281–1285 (1991)). Neurons can only be infected in the prenatal period, when neuroblasts are actively dividing (Sharpe et al., *Nature* 346:181–183 (1990)). Brain tumors constitute masses of dividing cells within a background of mostly non-dividing host cells and should be ideal candidates for targeted gene therapy by retrovirus vectors. The selective chemosensitization of rat C6 glioma cells in culture and in vivo using a similar retrovirus vector, VIK, has been reported (Ezzedine et al., *New Biol.* 3:608–614 (1991)). Rat C6 glioma cells infected with this vector and cloned in culture, C6VIK cells, were introduced subcutaneously into nude mice. Subsequent treatment of the animals with ganciclovir inhibited tumor growth of C6VIK cells, but had no effect on tumor growth of parental C6 cells.

It has been demonstrated that chemosensitivity to the nucleoside analogue, ganciclovir, can be increased in glioma cells by combined infection with a retrovirus bearing the HSV-TK gene and with wild type MoMLV. This treatment was effective at killing C6 tumor cells both in culture and in vivo. Even more strikingly, this effect can be transferred to "naive" (i.e., uninfected) C6 glioma cells.

In order to treat an actual tumor, transfer of the gene needs to take place in vivo. Previously, a producer cell line (mouse fibroblast-derived), releasing the reporter retrovirus vector, BAG, was implanted near a tumor bed of C6 glioma cells in the adult rat brain. This yielded a level of gene transfer to tumor cells of about 10%. However, the period of gene delivery was curtailed by immune rejection of the vector-producing line.

The duration of vector-mediated gene delivery to tumor cells has been extended in two ways. First, C6VIK glioma cells were superinfected with a "helper" wild type MoMLV. These C6VIKWT cells release both wild type virus and replication-defective virus vectors containing the HSV-TK gene, both of which can infect neighboring tumor cells, provided the latter are proliferatively active. Proliferation is a prerequisite for retrovirus integration (Miller et al., *Mol. Cell Biol.* 10:4239–4242 (1990)).

When neighboring cells are infected either sequentially or simultaneously with the vector and the wild type virus, they can, in turn, become "producer" cells able to release both the wild type virus and the vector to additional cells. This allows extended spread of vector production by dividing tumor cells in the brain, which are able to integrate retroviral DNA in the genome. These glioma-derived "producer" cells can migrate in the adult brain as do glioma cells (Burger et al., *J. Neurosurg.* 58:159–169 (1983)) and astrocytes (Jacque et al., *Dev. Neurosci.* 8:142–149 (1986); Zhou et al., *J. Comp. Neurol.* 292:320–330 (1990); Hatton et al., *Soc. for Neurosci. Abstracts* 15:1369 (1989)), and of intermingling with other tumor cells.

Another means to improve efficacy of gene transfer to glial tumors includes development of a glia-derived packaging line from the same strain in which the tumor is implanted or originates. Such cells will have increased longevity within the CNS and will also obviate the need for WT virus. The absence of WT virus will increase the safety of therapy. It will also remove a potential barrier to universal infection of recipient cells by the vector, since cells infected with the wild type virus are resistant to subsequent infection with either wild type virus or the vector, due to expression of envelope glycoproteins on their surface (Kabat, D., *Curr. Top. Microbiol. Immunol.* 148:1–42 (1989)).

C6VIKWT cells (C6 glioma cells bearing the HSV-TK gene, superinfected with MoMLV virus) were significantly more sensitive to ganciclovir than parental C6VIK cells. This effect is specific to the presence of the HSV-TK gene since C6BU1 cells infected with the MoMLV did not show any greater sensitivity than the parental cell line, C6BU1. This difference in sensitivity between C6VIK and C6VIKWT cells was even greater when assessed by a colony assay. The difference in sensitivity observed using these two assays may reflect a lower sensitivity of isolated cells as compared to those in colonies. Close cell contacts within cells in colonies may increase the transfer of HSV-TK gene allowing multiple integrations per cell or may increase the intracellular concentration of ganciclovir or toxic metabolites derived from it. The effectiveness of C6VIKWT cells was also apparent in their ability to sensitize recipient cells to ganciclovir, as evidenced by co-culture of recipient cells marked with the lacZ gene, C6BAG or C6BBAG cells, and donor cells, C6VIK or C6VIKWT. Since there was no significant difference in the ganciclovir sensitivity of C6BU1 and C6BWT cells, the transfer of the HSV-TK gene in the presence of wild type virus, rather than the wild type virus alone, is responsible for this killing effect. However, some transfer of ganciclovir sensitivity to recipient cells was seen with the C6VIK donor (i.e., even in the absence of WT virus). As a consequence, several assays were done to determine whether the increased sensitivity of recipient cells to ganciclovir was due to transfer of the TK gene, infection with wild type retrovirus and/or the release of a toxic metabolite. Medium from co-cultures was titered for VIK retrovirus and tested for toxicity to naive cells. Assays for gene transfer mediated by media from C6VIKWT cells documented the presence of vectors bearing the neomycin resistance gene and TK gene. No toxicity was noted when naive C6BU1 cells were exposed to media from cultures of C6VIKWT cells with or without ganciclovir treatment. This does not exclude the possibility that sensitivity in the absence of WT virus might be mediated by direct transfer of toxic metabolites by donor cells to recipient cells through cell-to-cell contacts, but suggests that these metabolites are not exchanged through the medium.

The extraordinary chemosensitivity of C6VIKWT cells to ganciclovir was apparent in vivo as well as in culture. The presence of wild type virus contributed to the sensitivity of these cells, as treatment of subcutaneous C6VIKWT tumors with ganciclovir completely blocked tumor growth, whereas in previous studies C6VIK tumors treated with ganciclovir continued to grow at a slow rate (Ezzedine et al., *New Biol.* 3:608–614 (1991)). C6VIKWT tumors grow more slowly than C6VIK tumors, suggesting that wild type retrovirus itself may interfere with the growth of tumor cells. However, injection of the WT MoMLV into subcutaneous C6 tumors appears to have no effect on tumor growth (Y. Takamiya, unpublished data). It has been shown that wild type retrovirus infection can affect the differentiated phenotype of cultured human glioma cell lines (Macchi et al., *Acta Neuropathol.* 81:670–674 (1991)), but it is not clear whether this alters the tumorigenicity of these cells. Co-injection of C6BAG and C6VIKWT cells followed by treatment with ganciclovir revealed a markedly reduced rate of tumor growth as compared with combinations of C6BAG and either C6BU1 or C6VIK cells, with no residual tumor cells seen histologically after therapy. This result is consistent with the transfer of the HSV-TK gene to recipient C6BAG tumor cells mediated by production of the VIK vector by adjacent C6VIKWT cells.

Although wild type MoMLV can cause leukemia and neuropathic effects in young mice (Sharpe et al., *Nature* 346:181–183 (1990); Kay et al., *Proc. Natl. Acad. Sci. USA* 88:1281–1285 (1991)), immune competent adult mice are quite resistant to the pathogenicity of this virus. The present in vivo data reported here, were obtained using nude mice which are immuno-compromised (Gullino et al., *Institute Lab Animal Resources (ILAR) News* 19:M1–M20 (1976)), although in this study all pathogenicity in animals appeared to be related to tumor growth in the brain.

The ganciclovir sensitivity of glioma cells infected with both a retrovirus vector bearing the HSV-TK gene and wild type MoMLV virus, as well as their ability to transfer sensitivity to "naive" cells in their vicinity could be mediated by several factors as schematized in FIG. 13. These include the cellular debilitating effects of wild type retrovirus infection; host production of antibodies in response to viral and tumor antigens (in immune competent animals); integration and expression of the HSV-TK gene in tumor cells, allowing the cells to generate toxic metabolites from ganciclovir; and possible transfer of these toxic metabolites to neighboring cells. A gene therapy strategy utilizing this system thus provides four separate and additive means to kill tumor cells, all of which have no effect on endogenous brain cells. Cells bearing the HSV-TK gene also show increased sensitivity to radiation in the presence of ganciclovir, as its metabolites will interfere with DNA repair as well as DNA synthesis. Further extension of killing can be achieved by creating vectors bearing genes for secretable proteins, which selectively kill or inhibit growth of tumor cells, or for surface proteins which stimulate immune rejection of tumor cells. Several different vectors could thus be used in concert and combined with more traditional therapies.

EXAMPLE 5

Methods

Plasmid Constructions: A rat cDNA containing the full length coding sequence for the rat cytochrome P450 2B1 was isolated from plasmid pSR-P450 (Vallette et al., *Nucl. Acid Res.* 17:723–733 (1989)) (provided by Dr. Milton Adesnik, NYU Medical School) by digestion with NcoI and EcoRI. This fragment was inserted into the pMFG plasmid (Dranoff et al., *Proc. Natl. Acad. Sci. USA* 90:3539–3543 (1993)) (provided by Dr. Richard Mulligan, MIT) downstream of the MoMLV LTR, following digestion with NcoI and BamHI, using a 15 bp EcoRI-BamHI adaptor (New England Biolabs). The resulting plasmid was pM450.

Cell Culture, Transfection and Isolation of Cytochrome P450 2B1-Expressing Cells: Cells were grown in Dulbecco's minimal essential medium (DMEM) with high glucose (cat. no. 10-013-LM, CELLGRO) supplemented with 10% fetal calf serum, 100,000 U/L penicillin and 100 mg/L streptomycin (Sigma) in a 5% $CO_2$ incubator. The pM450 construct was transfected into both rat C6 glioma and ΨCRE cells (Danos et al., *Proc. Natl. Acad. Sci. USA* 85:6460–6464 (1988)) together with pRSVneo (kindly provided by Dr. Michael Comb, MGH), a plasmid that encodes the gene for resistance to neomycin, in a molar ratio of 10:1 using LIPOFECTIN according to the manufacturer's instructions (GIBCO). Stable transfectants were cloned under selection in 1 mg/mL G418 (GIBCO). Neomycin-resistant C6 glioma and CRE cell clones were evaluated for cytochrome P450 2B1 activity by growth in the presence of 500 µM cyclophosphamide (CPA) added 24 hours following plating at a density of $2 \times 10^5$ cells/100 mm dish. One C6-derived clone (C450-8) and one ΨCRE-derived clone (R450-2) were destroyed completely after four days at this concentration of prodrug. These clones were used in further studies. Other CPA-resistant clones, CNEO-1 and C450-19, were used as controls. Titers of retrovirus production were not determined as the lack of a selectable marker in the MFG retrovirus vector precluded titering by counting drug-resistant clones after infection with retroviral supernatants (Cepko, C. in *Current Protocols in Molecular Biology*, Ausubel et al., eds., Wiley and Sons, New York, (1992), pp. 9.11.1–9.11.12). Preliminary experiments suggested that retrovirus titers might be quantified by employing acquisition of CPA-sensitivity by naive cells exposed to R450-2 supernatants.

Cyclophosphamide Dose-Response Assay: For dose-response curves, cells were plated at a density of $2 \times 10^5$ cells/100 mm dish (Corning) in quintuplicate. Two days later CPA was added to final concentrations of 0–100 µM. Five days after plating, the monolayers were rinsed twice with Hank's buffered saline (GIBCO) to remove dead cells. Monolayers were dispersed using trypsin-EDTA (GIBCO), and cell numbers were determined using a Coulter counter (Coulter Electronics Inc.).

Immunocytochemistry and Western blots: A rabbit polyclonal antiserum raised to rat P450 2B1 (Waxman, D. J., *J. Biol. Chem.* 259: 15481–15490 (1984); Waxman et al., *J. Biol. Chem.* 257:10446–10457 (1982)) was used to perform immunocytochemistry using the alkaline phosphatase method as described for the Vectastain reagent kit (Vector Laboratories, Burlingame, Calif.). Western blot analysis was performed on microsomal fractions (20 µg protein/lane) isolated from cultured cells; C450-8, C6, CNEO-1, and C450-19. Liver microsomes isolated from phenobarbital-induced rat liver 2 µg protein/lane) were included as a positive control. Proteins were resolved by electrophoresis in 10% SDS/polyacrylamide gels, transferred to nitrocellulose and probed with a rabbit anti-P450 2B1 antibody (Waxman, D. J., (1984), supra).

Determination of Cytochrome P450 2B1 Activity: Enzymatic activity was determined for each clonal line by assaying the 16β-hydroxylation of [4-$^{14}$C]androstenedione (6 mCi/mmol; Amersham) as described (Waxman, D. J., *Methods in Enzymology* 206:249–267 (1991); Waxman et al., *J. Biol. Chem.* 258:11937–11947 (1983)). Briefly, cells grown in monolayer were harvested and cell pellets were stored at −80° C. until subsequent preparation of microsomes. Enzyme assays were carried out for 30 min at 37° C. in 100 mM HEPES, pH 7.4, 0.1 mM EDTA, 50 AM $^{14}$C-labelled androstenedione, 100 µg of microsomal protein, and 1 mM NADPH in a total volume of 200 µl. The mixture was extracted twice with ethyl acetate, chromatographed on a silica-gel thin-layer chromatographic plate and developed sequentially in multiple solvent systems (Waxman, D. J., (1991), supra). Metabolites were localized by autoradiography and then quantified by liquid-scintillation counting.

Animal Studies: For animal injections, cultured cells in the proliferative stage were replated 24 hours before harvesting, then trypsinized, centrifuged at low speed, washed once by resuspension in Hank's buffered saline, centrifuged, and then resuspended in DMEM without serum at a density of 5×10$^6$ cells/mL. For subcutaneous injections, 10$^6$ C450-8 or C6 cells in 200 µl were injected into the flanks of athymic mice (NCY/Sed, nu/nu; MGH breeding colony; five animals per group). After 3 days, when tumors had reached a volume of about 0.01 cm$^3$ (as measured by external calipers) (Lee et al., *Neurosurgery* 26:598–605 (1990) and again at 14 days, 100 µl injections of either 20 mg CPA (Sigma) per mL saline or 100 µl saline were performed directly into the tumor mass. Animals were sacrificed at 17 days by euthanasia.

For intracerebral injections, mice were anesthetized with an intraperitoneal injection of Ketamin (100 mg per kg body weight) (Parke Davis, NJ) and Xylazine (20 mg per kg body weight) (Mobay Corp., KS). Surgical procedures were performed in a sterile fashion. After immobilizing the rodent in stereotactic apparatus (Kopf), a small incision was made in the skin overlying the skull. C6 glioma cells (10$^3$ cells in 2 µl) were stereotactically inoculated approximately 0.5 mm frontal and 0.5 mm right lateral to the bregma using a Hamilton syringe. The inoculation period was 5 minutes, with 2 minutes allowed for needle retraction. Three days later, the same burrhole was employed for the stereotactic grafting of 5×10$^6$ CRELacZ cells (cell line kindly provided by Dr. R. Mulligan, MIT) or 5×10$^6$ R450-2 cells in 25 µl of DMEM. Four, eight, and eleven days after this last injection, CPA (0.3 mg in 5 µl) was administered stereotactically, through the same skull opening, into the tumor and meningeal space of mice from both CRELacZ and R450-2 groups. Injections were carried out stereotactically over a period of ten minutes, with five minutes allowed for needle retraction. Animals were sacrificed, ten days after injection of the last dose of prodrug, by perfusing through the left ventricle approximately 3–5 mL of 100 mM sodium phosphate in 0.9% sodium chloride, pH 7.3, followed by 4% paraformaldehyde in 100 mM sodium phosphate, pH 7.3. Brains were carefully dissected from the skull and jaws of the animals, prior to placement overnight in 4% paraformaldehyde in 100 mM sodium phosphate, pH 7.3. For cryopreservation, brains were placed in 20% glycerol/10% dimethylsulfoxide in 100 mM sodium phosphate, pH 7.3, and then cut in 50 micron sections with a sledge microtome. Every sixth section was mounted onto gelatin-coated slides and stained with cresyl violet. To calculate brain tumor volumes, a computerized-image analyzer was used to scan tumor areas on each section. This analysis was performed in a blind fashion. Manual contouring was performed to distinguish tumor from normal brain cysts, or processing artifacts. Tumor volumes were obtained by multiplying the average tumor area from all sections in a brain by the distance (0.3 mm) between and including each section.

Results

Cyclophosphamide Sensitivity of C6 Glioma Cells in Culture: The cDNA for rat cytochrome P450 2B1 (Valletie et al., supra) was inserted into plasmid sequences for the MFG retrovirus vector (Dranoff et al., supra). The resulting plasmid (pM450) was then co-transfected with an expression vector bearing the neomycin (neo)-resistance gene into rat C6 glioma cells (Benda et al., *J. Neurosurg.* 34:310–323 (1971)). Two stably transfected, neoresistant clones were chosen for further study: 1) C450-8 cells, which showed the greatest sensitivity to CPA, and 2) CNEO-1 cells, which appeared, like parental C6 cells, to be relatively insensitive to this drug. A dose-response curve revealed that 27 µM CPA reduced the number of C450-8 cells by 50% in a cell proliferation assay (FIG. 14). In contrast, at least 80% of C6 and CNEO-1 cells survived incubation with up to 1 mM CPA. Therefore, chemosensitivity to the prodrug CPA was acquired by C6 glioma cells after transfection with the cytochrome P450 2B1 expression plasmid.

Expression and Microsomal Location of Cytochrome P450 2B1 in C450-8 Cells: Cytochrome P450 2B1 is an integral membrane protein of the hepatocyte endoplasmic reticulum (Monier et al., *J. Cell. Biol.* 107:457–470 (1988)). A rabbit polyclonal antiserum raised to cytochrome P450 2B1 (Waxman, D. J., (1984), supra) was employed to ascertain whether acquisition of CPA sensitivity was associated with P450 2B1 expression. An immunoreactive protein was present in C450-8 (FIG. 15a), but not in CNEO-1 cells (FIG. 15b). The lacelike reticular pattern in C450-8 cells suggested that this immunoreactive protein was correctly associated with endoplasmic reticulum (Monier et al., supra). Furthermore, Western blot analysis confirmed the presence of a single immunoreactive protein species in microsomal fractions prepared from C450-8, but not from C6 or CNEO-1 cells (FIG. 16).

NADPH-dependent androstenedione 16β-hydroxylase activity, which is specific for the cytochrome P450 2B1 enzyme (Waxman, D. J., (1991), supra; Waxman et al., (1983), supra), was tested in microsomal preparations from these cells. This activity was not detectable in C6 and/or CNEO-1 cells, whereas C450-8 cells possessed about 1% the activity of phenobarbital-induced rat liver microsomes (Table I), which are highly enriched for this P450 form (cf., FIG. 16). Addition of exogenous, purified NADPH-P450 reductase (Waxman et al., (1982), supra), the microsomal flavoenzyme that catalyzes an obligatory electron transfer from NADPH to all microsomal P450 enzymes, increased enzyme activity approximately two-fold in C450-8 cells. Taken in conjunction, these results indicate that C450-8 cells expressed enzymatically active cytochrome P450 2B1, which appeared to be localized in the endoplasmic reticulum.

TABLE I

Cytochrome P450 2B1 mediated androstenedione
16β-hydroxylase activity[a].

| Microsomes | Enzyme Activity (pmol/min/mg protein) |
|---|---|
| C6 | 0 |
| CNEO-1 | 0 |
| C450-8 | 53 |
| C450-8 plus exogenous, purified NADPH-P450 reductase[b] | 90 |
| CRE[c] | 0 |
| R450-2 | 20 |
| Phenobarbital-induced rate liver microsomes | 5845 |

[a]Enzyme activity was measured in microsomal fractions prepared from the indicated cell line, or from phenobarbital-induced rat liver microsomes as described under Methods.
[b]NADPH-P450 reductase from rabbit liver was added to the microsomal incubations under conditions where the endogenous microsomal P450 becomes saturated with respect to NADPH-P450 reductase, as described in the Methods.
[c]The activity of CRELacZ cells was not determined, since they were generated by transfection of parental CRE cells (whose P450 2B1 activity is nil). In addition, cultured cells generally lose any cytochrome P450 activity (Jefferson et al., Mol. Cell. Biol. 4:1929–1934 (1984)), further minimizing the possibility that CRELacZ cells could acquire P450 2B1 activity.

Cyclophosphamide Sensitivity of Subcutaneous C6 Glioma Tumors: The CPA-susceptibility of tumors formed by C6 or C450-8 cells was assessed by subcutaneous growth in the flanks of nude mice (FIG. 17). Three and fourteen days after the establishment of subcutaneous tumors, animals were injected intratumorally either with saline or with 2 mg of CPA. Three days after the last dose of CPA (seventeen days after tumor establishment) there was no statistically significant difference between the volumes of C6 and C450-8 tumors treated with saline (C6 tumors=0.747±0.325 cm³; C450-8 tumors=0.447±0.213 cm³; p>0.1). By contrast, a statistically significant difference was noted between the volumes of C6 and C450-8 tumors treated with CPA (C6 tumors=0.093±0.035 cm³; C450-8 tumors=0.016±0.003 cm³; p<0.01). This difference was also significant when the ratio of the mean volumes of CPA-treated to saline-treated C450-8 tumors (0.124 vs. 0.035; p<0.05). The increased susceptibility of C450-8 tumors to CPA as compared to C6 tumors suggests that CPA was convened into its active metabolites within the tumor itself, as well as by the liver.

In Vivo Acquisition of Cyclophosphamide Sensitivity By Brain Tumors: Murine ΨCRE fibroblasts were cotransfected with plasmids, pM450 and pRSVneo. One neo-resistant clone, designated R450-2, was selected on the basis of its chemosensitivity to CPA and its high P450 2B1-dependent androstenedione 16β-hydroxylase activity (Waxman, D. J., (1991), supra); Waxman et al., (1982), supra) compared to parental ΨCRE fibroblasts (Table I). These cells were then tested in a brain tumor model.

C6 glioma cells were inoculated stereotactically into the brains of athymic mice, followed three days later, by stereotactic inoculations of either murine fibroblasts expressing the lacZ gene from E. coli, CRELacZ cells, or R450-2 cells. Four, eight, and eleven days later, CPA was injected, through the same skull opening, into the tumor and meningeal space of mice from both CRELacZ and R450-2 groups. Animals were sacrificed ten days after injection of the last dose of prodrug. Extensive and friable tumor was found in the meningeal covering of the brains of 5/8 animals that had received injections of C6 plus CRELacZ cells followed by the administration of CPA (FIG. 18a). It was not possible to quantitate the meningeal tumor mass as dissection away from the skull and jaws of the animals was difficult and tissue sectioning/mounting resulted in extensive loss of the friable meningeal tumor tissue. In contrast, 7/8 animals that had received injections of C6 plus R450-2 cells followed by the administration of CPA showed no evidence of meningeal tumor (FIG. 18b) with ⅛ exhibiting a small residual mass. This result indicates that the in situ conversion of CPA to its active metabolites by neighboring fibroblasts, and probably by tumor cells infected with P450 2B1 retrovirus vectors, dramatically inhibited meningeal tumor spread when the prodrug was administered intrathecally/intratumorally.

The stereotactic injections of C6 tumor cells described above also resulted in the formation of solid tumors within the brain parenchyma. Histopathologic analysis of six brains from each group revealed essentially no tumor necrosis in control, CRELacZ-treated animals (FIG. 19a) but extensive tumor necrosis in ⅗ brains from the group that received the R450-2 fibroblasts (FIG. 19b). To provide a quantitative evaluation of the extent of tumor regression, parenchymal solid C6 glioma volumes were calculated from serial tissue sections using computerized-image analysis. Table II reveals that brain tumor volumes in three of the animals that had received the R450-2 retrovirus-producer cells were approximately 1/20, 1/5 and ½ that of the average brain tumor volume in rats that had received the lacZ-retrovirus producer cells. The other three R450-2-treated animals had tumors within the same size range as that seen in control animals. This result suggests that the combination of the cytochrome P450 2B1-expressing producer cells and CPA administered intrathecally/intratumorally also produces some regression of the parenchymal solid portion of the brain tumor.

TABLE II

Volumes of parenchymal brain tumors after R450-2 or CRELacZ grafts and cyclophosphamide administration[a].

| C6 + CRELacZ (mm³) | C6 + R450-2 |
|---|---|
| 47.5 | 3.2 |
| 51.5 | 14.2 |
| 54.7 | 28.4 |
| 62.4 | 87.4 |
| 72.6 | 105.3 |
| 85.1 | 171.4 |

[a]Tumor volumes were measured by computer-assisted contouring, as described in the methods.

Discussion

Over the last few years several experimental approaches involving expression of therapeutic genes have been shown to mediate the regression of experimental brain tumors in vivo (Moolten et al., Cancer Res. 46:5276–5281 (1986); Moolten et al., Hum. Gene Ther. 1:125–134 (1990); Moolten et al., J. Natl. Cancer Inst. 82:297–300 (1990); Short et al., J. Neurosci. Res. 27:427–433 (1990); Ezzedine et al., New Biol. 3:608–614 (1991); Culver et al., Science 256:1550–1552 (1992); Takamiya et. al., J. Neurosci. Res. 33:493–503 (1992); Yamada et al., Jpn. J. Cancer Res. 83:1244–1247 (1992); Ram et al., Cancer Res. 53:83–88 (1993); Oldfield et al., Hum. Gene Ther. 4:39–69 (1993); Takamiya et al., J. Neurosurg. 79:104–110 (1993); Caruso et al., Proc. Natl. Acad. Sci. USA 90:7024–7028 (1993); Boviatsis et al., Hum. Gene Ther. 5:183–191 (1994); Chiocca et al., "Virus-Mediated Genetic Treatment of Rodent Gliomas," in Gene Therapeutics, Wolff, J. A., ed., Birkhauser Publishers, Boston, Mass. (1994), pp. 245–262; Trojan et al., Science 259:94–97 (1993); Yu et al., Cancer Res. 53:3125–3128 (1993)).

In this Example, the inventors used the "killing" gene, cytochrome P450 2B1, which renders cells sensitive to CPA, for gene therapy of central nervous system neoplasms. The drug-conditional, killing action of P450 2B1 is not necessarily restricted to the gene therapy of central nervous system neoplasms, but could be applied for negative selection of other cell populations in culture or in vivo. Furthermore, the therapeutic paradigm presented herein is not restricted to the use of the cytochrome P450 2B1 gene with CPA. This approach can be applied to other cytochrome P450 enzymes that are involved in the biotransformation of other chemotherapeutic agents (LeBlanc and Waxman, *Drug Metab. Rev.* 20:395–439 (1989)).

The P450 2B1/CPA gene therapy approach appears to have features that may be more advantageous than the current treatment approaches which utilize a pharmacologic analogue of cyclophosphamide, 4-hydroxyperoxycyclophosphamide (4-HC).

This analogue spontaneously decomposes into 4-hydroxycyclophosphamide which then generates phosphoramide mustard (PM) without the need for enzymatic bioactivation (Peter et al., *Can. Treat. Rep.* 60:429–435 (1976); Colvin et al., (1981), supra; Friedman et al., *Cancer Res.* 46:2827–2833 (1986); Sladek, N. E., supra; Friedman et al., *Cancer Res.* 48:4189–4195 (1988)). Although 4-HC has exhibited therapeutic effectiveness in animal models of meningeal neoplasia (Arndt et al., *Cancer Res.* 47:5932–5934 (1987); Fuchs et al., *Cancer Res.* 50:1954–1959 (1990); Phillips et al., *Cancer Res.* 52:6168–6174 (1992); Friedman et al., *Proc. Amer. Assoc. Cancer Res.* 34:269 (1993)) and parenchymal solid brain tumors (Schuster et al., *Cancer Res.* 53:2338–2343 (1993a); Schuster et al., *Proc. Amer. Assoc. Cancer Res.* 34:269 (1993b)), it has also been associated with considerable neurotoxicity (Schuster et al., (1993a and b, supra)), since its conversion into cytotoxic metabolites has no anatomic or cellular selectivity.

In contrast, the treatment regimen described herein employs a stable, inert, lipophilic prodrug (CPA) which requires enzymatic conversion to exert its potent anticancer effect. It has been hypothesized that through introduction of the P450 2B1 gene into tumor cells, the cellular and anatomic location of CPA's enzymatic conversion will be effectively restricted to the neoplasm, thereby minimizing undesirable side-effects to normal cells in the brain and periphery.

In the approach described herein, the use of genetically engineered cells possesses features analogous to biodegradable implantable polymers for the local controlled delivery of activated anticancer agents, such as BCNU and 4-HC (Brem et al., *J. Neurosurg.* 80:283–290 (1994); Buahin et al., *Polymer. Adv. Tech.* 3:311–316 (1992); Tamargo et al., *Cancer Res.* 53:329–333 (1993)). Both the polymer and the genetically engineered cell method should allow sustained, high, and local activated drug levels within the tumor with minimal systemic and CNS toxicity. In addition, the generation of a retroviral vector from the genetically engineered cells should offer an additional therapeutic boost compared to the implantable polymer approach, by spreading the anatomic extent of tumor cells susceptible to the chemotherapeutic agent.

In contrast to other genes conferring drug-conditional lethality (i.e., the HSV-TK gene, the *E. coli* cytosine deaminase gene (Mullen et al., *Proc. Natl. Acad. Sci. USA* 89:33–37 (1992); Huber et al., *Cancer Res.* 53:4619–4626 (1993) and the *E. coli* gpt gene (Mroz et al., *Hum. Gene Ther.* 4:589–595 (1993)), tumor killing with the P450 2B1 gene should occur regardless of cell-cycle phase, since the active CPA-derived metabolites "mark" cells by interstrand cross-links in DNA. Maximum cytotoxicity occurs when the "marked" tumor cell replicates its DNA, which could occur at or subsequent to the time of drug treatment. This may present an advantage compared to the gene therapy paradigms that employ metabolites that have to be incorporated into replicating DNA strands for cytotoxic effects. For instance, HSV-TK produces phosphorylated ganciclovir (or acyclovir) molecules that act as nucleotide analogs and become incorporated into replicating DNA chains (Fyfe et al., *J. Biol. Chem.* 253:8721–8727 (1978)). These nucleotides are most effective for tumor cells when generated in the S phase of the cell cycle, since they have a relatively short half-life (Elion, G. B., supra). The large majority of cells in malignant brain tumors are not in the S phase (Nagashima et al., supra; Yoshii et al., supra), and thus may not be ideal targets for HSV-TK/ganciclovir gene treatments. It is also believed that the cytochrome P450 genes have a "memory" component in that metabolites of CPA bind tightly to DNA and all will die when it tries to replicate at a later date following drug treatment. In addition, since the P450/CPA mechanism of cell destruction is different from that of HSV-TK/ganciclovir and of other therapeutic genes (Trojan et al., supra; Yu et al., supra), it may be possible to combine these to achieve additive effects. The use of viral vectors that do not require DNA replication for gene expression might also provide another means to infect brain tumor cells that are not actively dividing. Treatment by delivery of multiple chemosensitivity genes into tumors should allow further refinements in current clinical regimens of chemotherapy for human tumors.

The mouse fibroblast line (R450-2) used for our studies expresses P450 2B1 activity. It is also assumed to generate defective retrovirus vectors bearing the cytochrome P450 2B1 gene. It is not clear at this time whether the tumor regression mediated by grafting of these cells into the tumor was caused by release of toxic CPA metabolites from P450 2B1-expressing fibroblasts and/or by retrovirus-mediated transfer of the P450 2B1 gene to neighboring tumor cells. Presumably, tumor cells could be killed either by uptake of active metabolites or by intracellular generation of these metabolites. In either case, it should be possible to transfer the cytochrome P450 2B1 gene into a variety of peripheral and brain tumors by using both viral and nonviral vectors (Short et al., supra; Boviatsis et al., supra; Chiocca et al., supra). The intracellular generation of CPA active metabolites appears to produce a very potent tumor "killing" effect; it has been demonstrated in Example 5 that activation of CPA within P450 2B1-expressing cells can transfer cytotoxicity to neighboring cells in a manner analogous to the "bystander" effect seen with HSV-TK (Moolten et at., (1990), supra; Ezzedine et al., supra; Takamiya et al., (1992), supra; Freeman et al., *J. Cell. Biochem.* 16F:47 (1992) and Freeman et al., *Cancer Res.* 53:5274–5283 (1993); Culver et al., supra; Li Bi et al., *Hum. Gene Ther.* 4:725–731 (1993)).

Introduction of fibroblasts expressing the cytochrome P450 2B1 gene into the parenchymal gliomatous tumors was most effective against meningeal neoplasia in mouse brain. Meningeal spread of tumor cells from peripheral (melanomas, lung and breast carcinomas), hematologic (lymphoma), and glial origin (ependymoma and glioblastoma) is a rapidly fatal type of cancer, referred to as meningeal neoplasia and/or carcinomatosis (Beerman, W. F., *JAMA* 58:1437–1439 (1912); Olson et al., *Arch. Neurol.* 30:122–137 (1974)). Whereas the growth of parenchymal solid tumors can be temporarily curtailed by surgery and/or radiation, tumor spread into the meninges is not well controlled by these therapeutic modalities. Drug therapies have had limited success due to systemic and central nervous system toxicity, poor penetration of the blood-brain barrier, and development of cellular resistance (Henson et al., "Meningeal Carcinomatosis," in *Cancer Medicine*, Holland et al., eds., Lea and Febiger, Philadelphia, Pa. (1993), pp. 2268–2286). The brain tumors developed in the animal model employed in our studies consisted primarily of C6 gliomas, because no tumors were formed by CRELacZ fibroblasts grafted alone into the parenchyma of athymic mice (unpublished results). In our experiments, the relative difference in the ability of CPA to effect regression of meningeal as compared to parenchymal brain tumors probably resulted from two factors: 1) the fluid-filled and loose spaces enclosed by the pial, arachnoidal and dural layers of the meningeal covering of the brain allowed more effective interaction of tumor cells with the fibroblasts, retrovirus vectors, CPA, and/or secreted cyclophosphamide metabolites; and 2) the elevated interstitial pressure within the parenchymal brain tumor impeded effective delivery of producer cells and prodrug. It is likely that alternate modes of CPA administration, such as through the arteries feeding the tumor, may result in more effective treatment of a parenchymal solid brain tumors. Better "mixing" between tumor cells and producer cells could be achieved by surgical reduction of the solid tumor mass or by convection delivery of the viral vector.

The use of the cytochrome P450 2B1 gene as a conditional killing gene in cancer gene therapy should enhance the therapeutic effectiveness of CPA by allowing high levels of cytotoxic metabolites to be generated within the tumor itself, with minimal levels of cytotoxic metabolites generated within other cells. This approach may potentially be combined with the inhibition of liver cytochrome P450-catalyzed CPA activation in order to minimize exposure of the patient to systemic toxicity from the prodrug's metabolites. Further it should be more effective than the currently used HSV-TK gene in killing tumor cells which are not dividing at the time of treatment.

EXAMPLE 6

In this Example, the involvement of programmed cell death (PCD) and the extent of additional cytotoxic effects in cultured C6 glioma cells exposed to the CPA/cytochrome P450 2B1 gene therapy paradigm were evaluated. The results demonstrate that CPA leads to PCD of cells that express the cytochrome P450 2B1 gene. Toxicity also occurs in neighboring C6 glioma cells that do not express the CPA-activating P450 2B1 gene product. This cytotoxic "bystander" effect results from two mechanisms: 1) a "cell-mediated" mechanism, which requires proximity of P450-expressing cells and naive tumor cells, and 2) a "secretory" mechanism that is transmitted through the medium from P450-expressing cells to naive tumor cells.

Further, by employing pharmacologic analogs of CPA that are converted into either phosphoramide mustard (PM) or acrolein, it was found that the PM-generating pathway was the major contributor of the cytotoxicity mediated by cell proximity, while the acrolein-generating pathway was primarily responsible for the cytotoxicity mediated by secretion into the medium.

Materials And Methods

Chemicals and cell lines: Cyclophosphamide (CPA) was purchased from Sigma. CPA analogs, trans-4-phenylcyclophosphamide (T4P), and didechlorocyclophosphamide (DCPA) (Cox, P. J., *Biochem. Pharmacol.* 628:2045–2049 (1979); Plowchalk et al., *Toxicol. Appl. Pharmacol.* 107:472–481 (1991)), were kindly provided by Dr. Susan M. Ludeman (The Johns Hopkins Oncology Center, Baltimore, Md.). The cell lines, C6-Neo (previously designated CNEO-1 in Example 5, supra) and C6-P450 (previously designated C450-8 in Example 5, supra) were generated by transfection of rat C6 glioma cells (Benda et al., *Science* 161:370–371 (1969)) with plasmids bearing the neomycin phosphotransferase gene and the cDNA for rat cytochrome P450 2B1, as described in Example 5. This cytochrome P450 is the most active in metabolizing CPA among eleven other rat liver P450 enzymes tested (Clarke et al., *Cancer Res.* 49:2344–2350 (1989)). Cells were grown in Dulbecco's minimal essential medium (DMEM) with high glucose (cat. no. 10-013-LM, CELLGRO™) supplemented with 10% fetal calf serum, 100,000 U/L penicillin and 100 mg/L streptomycin (Sigma) in a 5% $CO_2$ incubator.

Colony formation assay: For colony formation assays, cells were plated at a density of 1,000 cells/10 cm dish in triplicate. The cloning efficiency was approximately 25% for control cultures. The next day, 0.5 mM CPA was added and incubations were carried out for six days. Cells were then rinsed once with Hank's buffered saline (GIBCO), stained with Giemsa (Fisher Diagnostics), and colonies larger than 1 mm in diameter were counted.

Cell proliferation assays: For cell proliferation assays, cells ($2 \times 10^5$ per dish, unless otherwise noted) were plated onto 10 cm dishes. Twenty-four hours later, CPA, T4P, or DCPA were added to a final concentration of 0.5 mM. Incubations were continued for four days and cell numbers were assayed using a Coulter counter (Coulter Electronics Inc.), after harvesting in trypsinEDTA.

Trypsinization and replating assay: To determine the temporal kinetics of CPA-mediated cytotoxicity, $2 \times 10^6$ cells were plated onto each 10 cm dish. Twenty-four hours later, 0.5 mM CPA was added and cells were incubated for the times indicated in each figure. Cells were then trypsinized and replated at a density of $2 \times 10^5$ cells/10 cm dish. Nine days later, cell numbers were evaluated by Coulter counting.

Secretory effect assay: To assess the effect of conditioned medium, cells were co-cultured in dishes using the "insert" system (Falcon). This consists of tissue culture dishes (diameter=3.5 cm), which contain a micropore membrane (pore diameter=0.45 μm) that physically separates cell populations plated into the upper and lower chambers but permits the exchange of components in the medium. C6 cells ($3.4 \times 10^5$ cells) were plated into the bottom chamber, while C6-P450 ($3.4 \times 10^5$ cells) or C6-Neo cells ($3.4 \times 10^5$ cells) were plated into the upper chamber (on top of the filter) in a total volume of 5 mL of medium. After an overnight incubation, 0.5 mM CPA was added to this medium. Four days later, the membrane on which the C6-P450 or C6-Neo cells were growing was removed and then the number of C6 glioma cells in the lower chamber was determined by counting with a Coulter apparatus. Surviving C6 cells were then replated at a density of $2 \times 10^5$ cells per 10 cm dish without CPA. Nine days later, these cells were trypsinized and counted using the Coulter apparatus.

Co-culture assay: Co-cultures of C6-P450 and C6 cells were incubated in triplicate at different ratios (where 0, 10, 50, 90, and 100% of the cells were C6-P450 cells) to achieve a total number of $2 \times 10^6$ cells/10 cm dish. After 24 hours, 0.5 mM CPA was added and four days later, cells were counted as previously described. To compare the killing achieved by cell contact with that obtained by exposure to conditioned medium, the supernatant from each co-culture was harvested, filtered through 0.45 μm membrane filters, mixed in a 1:1 ratio with 5 mL of fresh medium and added to overnight cultures of C6 cells ($2 \times 10^6$ cells/10 cm dish in triplicate). Four days later, C6 cells were washed, harvested and counted. To determine the specificity of the cell-mediated killing effect from the co-culture assays, C6 cells were incubated overnight with C6 cells that expressed the neomycin phosphotransferase gene (C6-Neo), with irradiated C6 cells, with irradiated C6-Neo, and with irradiated C6-P450 cells. γ-irradiation was performed by exposing cells to a total of 6000 rads emitted by a $^{51}$chromium source. Cells exposed to this level of radiation did not proliferate but remained attached to tissue culture dishes for seven days before detaching and losing viability.

Genomic DNA analysis: Genomic DNA was extracted from C6 and from C6-P450 cells exposed to CPA for various time periods by using a commercially available kit (Nucleon™, ScotLab). The DNA was isolated from cells that were attached as well as from those that had lost their viability and were floating in the supernatant. DNA (1 μg) from each time point was analyzed by electrophoresis on 1% agarose gels.

Statistical tests: All tests of significance were performed using the Sigmastat software (Jandel Corporation, SanRafael, Calif.).

Results

Effect of CPA on the proliferation of C6 cells expressing the cytochrome P450 2B1 gene: The generation of cell lines C6-P450 (previously designated as C450-8) and C6-Neo (previously designated as CNeo-1) has been described (Wei et al., Hum. Gene Ther. 5:969–978 (1994)). These cell lines were derived from C6 glioma cells stably transfected with the rat cytochrome P450 2B1 gene and the neomycin phosphotransferase gene, respectively. FIG. 20A shows that C6, C6-P450, and C6-Neo glioma cells proliferate at similar rates in the absence of CPA. However, in the presence of 0.5 mM CPA, there was selective and complete growth inhibition of C6-P450 cells over the course of 10 days.

Death of cells that express the cytochrome P450 2B1 gene occurs within hours of exposure to CPA: To investigate the time course of CPA's killing action, a trypsinization and replating assay was performed: $2 \times 10^6$ cells were exposed for various time periods to 0.5 mM CPA (pulse period). The cells were then washed and trypsinized to remove excess prodrug and/or metabolites, and replated at a density of $2 \times 10^5$ cells per 10 cm dish. Cells were counted nine days later. Table III shows that a 3-hour pulse of CPA was sufficient to completely inhibit the growth of the replated C6-P450 cells. Proliferation of the replated parental C6 glioma cells was unaffected by CPA even after a 96-hour period of drug exposure. This demonstration that the killing effect of CPA on cells is complete within 3 hours indicates that CPA is rapidly converted within the C6-P450 cells into its cytotoxic metabolite(s).

Transfer of cytotoxic metabolites to naive C6 cells through medium harvested from C6-P450 cells: The generation of toxic metabolites could produce a cytotoxic effect on neighboring cells. The inventors thus sought to determine whether conditioned medium could transfer the cytotoxic effect of CPA metabolized by C6-P450 cells onto parental C6 cells. Conditioned medium was harvested from C6 or C6-P450 cells exposed to CPA for the time periods shown in Table IV, and was then added to C6 glioma cells to evaluate their colony forming ability. The results in Table IV show that a 3-hour exposure of C6-P450 cells to CPA was sufficient to generate conditioned medium which, upon addition to C6 cells, decreased their cloning efficiency by approximately 45%. The inhibitory activity of this conditioned medium increased with time of exposure of the C6-P450 cells to CPA. Complete inhibition of C6 cell colony formation was achieved through incubation with medium harvested from C6-P450 cells exposed to CPA for 24 hours (Table IV). This indicates that CPA-treated C6-P450 cells secrete soluble toxic metabolites that accumulate in the medium. Since the CPA metabolite, PM, does not efficiently diffuse across cell membranes (Genka et al., Cancer Chemother. Pharmacol. 27:1–7 (1990)), it is likely that the active metabolites in this conditioned medium were the diffusible metabolites, i.e., 4-HCPA and/or acrolein. The killing of C6 cells by medium conditioned by CPA-treated C6-P450 cells is termed here the "secretory effect."

TABLE III

Trypsinization and Replating Assay[a]

| Trypsinization and replating assay | Time after addition of CPA (hours) | | | | | | | | | |
|---|---|---|---|---|---|---|---|---|---|---|
| | 0.5 | 1.5 | 3 | 6 | 10 | 24 | 32 | 48 | 72 | 96 |
| | Cell number ($\times 10^6$) | | | | | | | | | |
| C6[b] | 11.6 ± 0.4 | 21.7 ± 0.6 | 13.1 ± 1.6 | 12.9 ± 0.7 | 20.4 ± 0.6 | 17 ± 0.7 | 15.4 ± 0.5 | 18.3 ± 1 | 20.2 ± 0.9 | 28.8 ± 0.8 |
| C6-P450 | 12 ± 1 | 24.1 ± 0.6 | 0.2 | 0.1 | 0.1 | 0.1 | 0 | 0.1 | 0 | 0 |

[a]: $2 \times 10^6$ C6 or C6-P450 cells were plated onto 10 cm dishes in duplicate. Twenty-four hours later, 0.5 mM CPA was added to each dish. At the indicated time, cells were trypsinized and replated at a density of $2 \times 10^5$ cells/10 cm dish in fresh medium in triplicate. Nine days later, cells in each dish were trypsinized and counted.
[b]: the cell number is given as the mean ± S.E.

TABLE IV

C6 Colony Formation After Exposure to Conditioned Medium from CPA-Exposed C6 or C6-P450 cells[a]

| C6 exposed to CM from | Time after addition of CPA (hours) | | | | | | | | | |
|---|---|---|---|---|---|---|---|---|---|---|
| | 0.5 | 1.5 | 3 | 6 | 10 | 24 | 32 | 48 | 72 | 96 |
| | Colony numbers | | | | | | | | | |
| C6 | 247 ± 3 | 256 ± 7 | 257 ± 1 | 260 ± 4 | 245 ± 5 | 255 ± 14 | 240 ± 2 | 245 ± 6 | 260 ± 5 | 260 ± 9 |
| C6-P450 | 263 ± 6 | 267 ± 9 | 144 ± 19 | 94 ± 8 | 12 ± 0.3 | 0 | 0 | 0 | 0 | 0 |

[a]: Conditioned medium from C6 or C6-P450 cells exposed to 0.5 mM CPA for the indicated times (0.5, 1.5, 3, 6, 10, 24, 32, 48, 72 and 96 hours) was harvested and added to plates containing overnight plated C6 cells (1000 cells/dish with clonogenic efficiency of approximately 25%). Colony numbers were determined six days later. Colonies greater than 1 mm in diameter were counted. Values represent the mean ± S.E.

To further demonstrate the presence of secreted cytotoxic metabolite(s), C6 and C6-P450 cells (1:1 ratio) were cultured using Falcon co-culture inserts, which provide for a physical separation of the two cell types through the use of a micropore filter, yet allow the free diffusion of their supernatants. As a control, C6 and C6-Neo cells (1:1 ratio) were also plated in this configuration. CPA was added to the culture medium and the number of C6 cells in the lower culture compartment was determined four days later. Under these culture conditions, there was approximately a 50% decrease in the number of C6 cells co-cultured with C6-P450 cells under these conditions in the presence of CPA (FIG. 21A), compared to C6 cells co-cultured with C6-P450 cells in the absence of CPA or C6 cells co-cultured with C6-Neo cells. When these C6 cells were stimulated to proliferate by trypsinization and replating, the toxic effects of CPA metabolites generated by C6-P450 cells were accentuated, resulting in an approximate 90% decrease in C6 cell number. Therefore, small soluble cytotoxic factor(s) or metabolites can be transferred through the culture medium from P450-positive to P450-negative tumor cells.

Endonucleolytic cleavage of DNA in C6-P450 cells exposed to CPA: The inventors next wanted to determine if a programmed cell death (PCD) contributed to the growth inhibitory effects of the CPA/cytochrome P450 2B1 gene therapy paradigm. One of the hallmarks of PCD is the endonucleolytic cleavage of chromosomal DNA (Wyllie, A. H., Nature 284:555–556 (1980)). Genomic DNA was isolated from C6 or C6-P450 cells exposed to CPA for varying time periods. FIG. 22A shows that genomic DNA from C6-P450 cells exhibited the nucleosome laddering characteristic of PCD, seventy-two hours after exposure to CPA. On the contrary, genomic DNA from C6 cells was intact even 4 days after exposure to CPA. PCD is thus involved in the cellular death seen with the CPA/cytochrome P450 2B1 gene therapy paradigm.

A cell-mediated effect also contributes to cytotoxicity: The inventors sought to determine if a cell-mediated effect contributed to the CPA/cytochrome P450 2B1 gene therapy paradigm. FIG. 23A shows that when C6 and C6-P450 cells were co-cultured so that 10% of cells on a dish express the P450 gene there was a 75% decrease in the proliferation of C6 cells (from $28 \times 10^6$ to $8 \times 10^6$ cells) in response to CPA over 4 days. When the number of co-cultured cells containing the P450 gene was increased to 50%, there was a proportional decrease in C6 cell proliferation, to approximately 85% (from $28 \times 10^6$ to $2 \times 10^6$) in response to CPA. When the number of C6-P450 cells was increased further so that they represented 90% of cells on a dish, there was complete inhibition in the proliferation of the remaining C6 cells over a four day period of exposure to CPA. The inventors conclude that growing the two cell populations in close proximity to each other is a powerful mediator of transcellular toxicity in the CPA/cytochrome P450 2B1 gene therapy paradigm.

In a control study, C6 cells represented 90% of cells in the dish, whereas the remaining 10% of cells consisted of: a) C6-Neo cells, b) irradiated C6 cells, c) irradiated C6-Neo cells, or d) irradiated C6-P450 cells (FIG. 23B). It was evident that co-culture with C6-Neo cells did not affect the proliferation of C6 cells (column 2). It was also evident that killing C6 cells by irradiation did not mediate toxicity on the remaining naive C6 cells (column 3). There was a small, but not statistically significant (p >0.1, Student's t-test) decrease in the proliferation of C6 cells co-cultured with irradiated C6-Neo cells (column 4). However, there was a statistically significant decrease (30%) in the proliferation of C6 cells co-cultured with irradiated C6-P450 cells (column 5) (p<0.01, Student's t-test). This suggested that irradiated C6-P450 cells were able to activate CPA at levels sufficient to mediate toxicity onto neighboring C6 cells.

The supernatant from the cell-mediated killing is cytotoxic: To assess whether toxic metabolites were present in the medium of the co-cultures described in FIG. 23A, supernatants from each co-culture were harvested after the four-day exposure to CPA and were added to naive C6 cells ($2 \times 10^6$ cells). Four days later, these cells were counted. FIG. 24 shows that there was no inhibition in the proliferation of C6 cells exposed to conditioned. medium harvested from the co-culture assays in which 0, 10, or 50% of cells contained the P450 2B1 gene. There was an approximate 30% decrease in proliferation of C6 cells exposed to conditioned medium harvested from the assays in which 90 or 100% of cells contained the P450 gene (p<0.05, Student's t-test). These findings indicate that cytotoxic factors were present in the medium of co-culture assays in which there was a large majority of C6-P450 cells and suggest that, after four days of CPA treatment, secreted cytotoxic metabolites were contributing to the cell-mediated death of C6 cells. However, the finding that this medium was cytotoxic only if 90% of the cells on the dish were C6-P450 indicated that growing the two cell populations in proximity for four days resulted in more efficient CPA-mediated killing of the naive C6 cells. The variance in the growth-inhibitory strength of the secretory effect described in the results of FIG. 24 compared to that of Table IV and FIG. 21 can be explained by the relative instability of 4-HCPA and acrolein secreted in the medium. In the experiments listed in Table IV and FIG. 21, these metabolites were freshly produced by P450 2B1-positive tumor cells, and the conditioned medium was likely to provide more extensive toxicity onto P450 2B1-negative tumor cells. In the experiment listed in this paragraph, the conditioned medium was harvested from four day-old cultures and most of the metabolites had probably decomposed, diminishing the extent of the secretory effect.

Characterization of different CPA bio-activating pathways: The bioactivation of CPA by cytochrome P450 2B1 generates 4-hydroxycyclophosphamide (4-HCPA), an unstable compound that is less lipophilic than the parent drug. 4-HCPA then decomposes to generate acrolein and phosphoramide mustard (PM). In order to evaluate the relative contributions of the acrolein- and PM-generating pathways in the cell-mediated and secretory toxicities of CPA, we employed CPA analogs that upon bioactivation generate only one or the other toxic metabolite: T4P is metabolized into PM without formation of acrolein, whereas DCPA is converted into acrolein without formation of PM (Cox, P. J., Biochem. Pharmacol. 28:2045–2049 (1979); Plowchalk and Mattison, Toxicol. Appl. Pharmacol. 107:472–481 (1991)). In a cell proliferation assay, T4P conferred cytotoxicity toward C6 glioma cells (20% inhibition in cell proliferation compared to untreated C6 cells; Table V—part A; p<0.05, Student's t-test), whereas CPA and DCPA had no effect on C6 cell proliferation. However, T4P had an even greater effect on C6-P450 cells, inhibiting their proliferation by 79% compared to untreated C6-P450 cells (p<0.001, Student's t-test). DCPA had no effect on C6-P450 cell proliferation, while CPA had the greatest effect, producing not only complete inhibition of cell proliferation but an actual decrease in cell number (from $2 \times 10^6$ to $1.15 \times 10^6$ remaining cells in the experiment shown).

To further confirm the growth inhibitory effect of T4P and CPA, the trypsinization and replating assay was used (Table V—part B). No significant differences were observed in the proliferation of C6 cells that had been treated with the above compounds. On the contrary, the proliferation of C6-P450 cells treated with CPA or T4P was completely inhibited. DCPA had no effect under these conditions.

A colony formation assay was used to investigate the secretory effect (Table V—panel C). Conditioned medium from each of the treated groups (in Table V—panel A) was added to C6 cells. Nine days later, C6 colony counts revealed that conditioned medium harvested from C6-P450 cells treated with DCPA or CPA was highly toxic to C6 cell growth. On the contrary, conditioned medium harvested from C6-P450 cells treated with T4P had minimal effects on C6 colony formation. Taken together, these results indicate that the acrolein-generating pathway (represented by DCPA) is primarily involved in the secretory effect with minimal involvement of the PM-generating pathway (represented by T4P). However, in a cell proliferation assay, where there is more cell-to-cell contact than in a colony formation assay, the PM-activating pathway corresponds to the more significant operative mechanism of growth inhibition. This suggests that the latter pathway may be an important contributor to the cell-mediated cytotoxicity of CPA.

TABLE V

Effects of Different CPA Analogues on C6-P450 Cells[a]

| | | Control | CPA | T4P | DCPA |
|---|---|---|---|---|---|
| | | Cell proliferation assay[b] | | | |
| A | C6 | 20.73±0.66 | 21.10±1.37 | 16.6±0.87* | 21.51±0.43 |
| | C6-P450 | 26.67±1.39 | 1.15±0.11* | 5.59±0.07* | 22.57±0.44 |
| | | Trypsinization and replating assay[c] | | | |
| B | C6 | 21.65±0.34 | 21.48±0.38 | 19±1.03 | 20.58±0.33 |
| | C6-450 | 22.27±0.32 | 0.11±0.01* | 0.31±0.07* | 21.29±0.17 |
| | | Secretion effect: CM from[d] | | | |
| C | C6 | 310±10.7 | 271±14.2 | 277±1.8 | 301±4.6 |
| | C6-P450 | 296±6.2 | 0 | 279±3 | 5±0.9* |

[a]: $2 \times 10^6$ C6 or C6-P450 cells were plated onto a 10 cm dish in triplicate. The next day, 0.5 mM CPA, T4P, DCPA or control medium were added to each dish. After four days of incubation, cells were trypsinized and counted.
[b]: In panel A, the number of C6 or C6-P450 cells in each dish was predetermined and expressed as an average ($\times 10^6$) ± S.E.
[c]: In panel B, a trypsinization and replating assay was performed by trypsinizing surviving cells at the end of the experiment in panel A and replating them at a density of $2 \times 10^5$ cells/10 cm dish in fresh medium in triplicate. Nine days later, cells were retrypsinized and counted.
[d]: In panel C, a secretory effect assay was carried out by harvesting the conditioned media from each culture at the end of the experiment in panel B and adding it to overnight cultures of 1000 C6 cells/10 cm dish. The colony number was given as mean ± S.E.
*values represent a statistically significant change.

Discussion

Cytochrome P450 2B1/CPA gene therapy for cancer: The inventors have discovered that the insertion of the rat cytochrome P450 2B1 transgene into tumor cells to render them sensitive to the antitumor action of cyclophosphamide holds promise as a novel therapeutic strategy against tumors. Example 5 shows that fibroblasts genetically engineered to produce a retrovirus vector that bears the above gene will induce tumor regression in animal models of peripheral and brain tumors.

In this Example, the inventors have sought to elucidate the cytotoxic mechanisms that contribute to the effectiveness of this gene therapy strategy. The major objectives of this study were (a) to determine if cyclophosphamide-induced toxicity of P450 2B1-positive tumor cells was linked to programmed cell death, (b) to evaluate whether expression of the P450 2B1 gene in tumor cells would also sensitize P450 2B1-negative tumor cells to cyclophosphamide ("bystander" effect), and (c) to characterize the CPA-activating pathways that contribute to this "bystander" sensitization. The results demonstrate that cytotoxicity is transferred to naive tumor cells both through the conditioned medium ("secretory" effect) and by growth in proximity ("cell-mediated" effect), and that this cytotoxicity is ultimately linked to PCD. Current gene therapy techniques do not permit the transfer of a therapeutic gene into all tumor cells, and thus, the findings of this report provide support for a gene therapy approach using the cytochrome P450 2B1/CPA paradigm.

Three assays of cell growth were used to evaluate these mechanisms: a cell proliferation assay, a colony formation assay, and a trypsinization and replating assay. The first assay is probably the least sensitive, since tumor cells were plated at relatively high density and reach confluency within 2–4 days, leaving little time for effective antitumor action from a drug whose cytotoxic potential becomes manifest during cell division. The second assay is more sensitive, since cells are plated at extremely low density (1000 cells per 10 cm dish) and, in order to form a colony, individual cells have to proliferate and resist the drug's cytotoxic action for several days. In the third assay, cells are exposed to the prodrug for a brief time period and then are replated at low density in the absence of the prodrug, allowing measurement of the ability of treated cells to recover from the drug's cytotoxic effect.

Cell-mediated toxicity: The toxicity of CPA can be transferred to tumor cells that do not express cytochrome P450 2B1 both by cell contact (cell-mediated effect) and through the medium (secretory effect). The cell-mediated effect is defined as the killing effect obtained when naive tumor cells are grown in proximity with prodrug-metabolizing cells. The secretory effect is defined as the killing effect obtained by exposing pure populations of naive tumor cells to medium conditioned by prodrug-metabolizing cells.

Several properties seem to define the cell-mediated effect. This effect requires expression of the cytochrome P450 2B1 gene, since co-culture with irradiated C6 or C6-Neo cells in the presence of CPA does not coffer cytotoxicity. This cell-mediated effect is incremental, in that complete inhibition of cell proliferation and a decrease in tumor cell number can be achieved by increasing the percentage of cells that express the cytochrome P450 2B1 gene. This effect also appears to be irreversible, in that cells continue to die even after a brief pulse of CPA followed by washing and replating to remove excess prodrug.

The secretory effect: The presence of a secretory effect differentiates the CPA/cytochrome P450'2B1 gene therapy paradigm from other types, such as the ganciclovir/herpes simplex virus thymidine kinase (HSV-TK) gene therapy strategy (Moolten, F. L., Cancer Res. 46:5276–5281 (1986); Freeman et al., Cancer Res. 53:5247–5283 (1993); Ezzeddine et al., New Biol. 3:608–614 (1991)). In the case of the latter gene therapy strategy, conditioned medium from ganciclovir-treated tumor cells containing the HSV-TK gene is not cytotoxic to untreated, naive tumor cells (Takamiya et al., J. Neurosci. Res. 33:493–450 (1992)), although toxic metabolites can be transferred across cell contacts (Li Bi et al., Hum. Gene Ther. 4:725–731 (1993)). The inventors hypothesize that the formation of secreted cytotoxic metabolites in CPA/cytochrome P450 2B1 gene therapy will provide a therapeutic boost against tumors. Even though the secreted metabolites may lead to some undesirable toxicity to normal cells, their exclusive generation within the tumor by directed gene delivery should maximize neoplastic cell killing and minimize deleterious effects on normal cells.

Comparison of cell-mediated and secretory effects: It is evident that the secretory effect partially contributes to the cytotoxicity of the cell-mediated effect. The latter is active in high-density co-cultures when 10% of tumor cells contain the P450 2B1 gene, while the former becomes apparent in the medium where most of the tumor cells express the P450 2B1 gene. The cell-mediated effect produces complete inhibition of cell growth in the cell proliferation assays (see FIG. 20B and Table V (A)), even after a mere three hour exposure to CPA (see Table III). The secretory effect is apparent only in the more sensitive colony formation assay and complete inhibition of cell proliferation can be achieved by exposing cells to medium from C6-P450 cells treated with CPA for more than 24 hours (see Table IV). Furthermore, even when exposure to conditioned medium was maximized by co-culturing C6 and C6-P450 cells in environments separated by filters, there was only a 50% inhibition in the proliferation of C6 cells over a four day period (see FIG. 21A). It was concluded that the cell-mediated effect is a more general mechanism of tumor cell killing and that the secretory effect partially contributes to this cell-mediated cytotoxicity.

Ultimately, the ability to enhance oncologic chemotherapy through the delivery of genes that would allow the intracellular conversion of prodrugs into active drugs should achieve the objective of maximum cytotoxicity for tumor cells with minimal effects on normal cells. The combination of several prodrug-gene therapy systems that have different modes of action (for example, ganciclovir/HSV-TK targets cells in the S-phase, while cyclophosphamide/cytochrome P450 2B1 targets cells in all phases), as well as the expression of cytokines that expand the immune response, such as interleukin-4 (Yu et al., *Cancer Res.* 53:3125–3128 (1993)), GM-CSF (Dranoff et al., *Proc. Natl. Acad. Sci. USA* 90:3539–3543 (1993)), and antisense RNAs that alter tumor cell metabolism, such as IGF-2 (Trojan et al., *Science* 259:94–97 (1993)), should expand the antitumor effectiveness of cancer gene therapy.

EXAMPLE 7

In this Example, cyclophosphamide (CPA) sensitivity of rat 9L tumor cells, stably transfected to express cytochrome P450 2B1, was studied in culture, and also following subcutaneous implantation, and growth of a solid tumor, in the outer thighs of Fischer rats. CPA treatment of cytochrome P450 2B1-expressing tumors led to complete inhibition of tumor growth. The results demonstrate that a systemic solid tumor growing in the periphery can be rendered highly susceptible to oxazaphosphorine treatment in vivo where intratumoral prodrug activation was achieved by the tumoral expression of the cytochrome P450 2B1 gene.

Materials and Methods

Abbreviations: 9L-Z, 9L cells that stably express *E. coli* β-galactosidase; 9L-ZP, 9L cells that stably express *E. coli* β-galactosidase and rat cytochrome P450 2B1; L450-2, 9L cells that stably express rat cytochrome P450 2B1.

Chemicals: Cyclophosphamide and ifosphamide were obtained from the Drug Synthesis and Chemistry Branch, National Cancer Institute (Bethesda, Md.). 4-hydroperoxy cyclophosphamide was obtained from Nova Pharmaceutical Corporation (Baltimore, Md.). Metyrapone was purchased from Aldrich Chemical Co. (Milwaukee, Wis.)

Stable transfection of 9L cells: Rat 9L gliosarcoma cells (Barker et al., *Cancer Res.* 33:976–986 (1973)) were grown in alpha minimum essential medium (GIBCO/BRL, Inc.) containing 10% fetal bovine serum, 10 units/mL penicillin, and 10 mg/mL streptomycin. Cells were maintained in a humidified atmosphere of 5% $CO_2$/95% air. 9L cells were co-transfected with a rat cytochrome P450 2B1 expression plasmid (pMT2-cytochrome P450 2B1, provided by Drs. Milton Adesnik and Allison Reiss, NYU Medical School) and plasmid pCMV-βgal. Neo (a gift from Dr. H. Li, Dana Farber Cancer Institute), in a molar ratio of 10:1 using Lipofectin (GIBCO/BRL, Inc.) according to the manufacturer's instructions. The plasmid pCMV-βgal. NEO contains a neomycin phosphotransferase gene, which confers resistance to G418, and also the lac Z (β-galactosidase) gene of *Escherichia coli*, which serves as a control and provides a convenient cell marker. Stable transfectants were cloned under selection in 1 mg/mL G418 (GIBCO/BRL, Inc.). Cell lines resistant to G418 were cloned, propagated, and evaluated. L450-2, another cytochrome P450 2B1-expressing 9L gliosarcoma-derived cell line, was prepared by similar methods.

To test for drug sensitivity, $1\times10^5$ cells were plated in 30-mm tissue culture plates (Falcon 3046) in duplicate. Drugs were added 18–24 hours after seeding. Cells were allowed to grow for times ranging up to 5 days after drug treatment, and the final cell number was then determined. Cells were rinsed with phosphate buffered saline or Hank's buffered saline, dispersed using trypsin-EDTA (GIBCO/BRL, Inc.), and then counted with a hemocytometer. Results are expressed as a growth ratio, i.e., the number of cells in plates containing drug as a percentage of the corresponding drug-free controls (mean±range of duplicate determinations).

Co-culture Experiments: Parental 9L cells were plated in the bottom wells of culture plates (Falcon 3502), and cytochrome P450 2B1-negative or cytochrome P450 2B1-positive cells were plated into 25 mm cell culture inserts (0.45 μm pore size, Falcon 3090). Culture media were removed 18–24 hours later by aspiration. Culture medium without drug (1.0 mL) was added to the bottom well, and 1.0 mL medium containing drug was added to the upper cell culture insert. Cell numbers were determined 5 days later, as described above.

Tumor Growth Delay Studies: 9L cells were grown subcutaneously (s.c.) as solid tumors in female Fischer 344 rats. Adult female Fischer 344 rats (120–150g) were inoculated at $2\times10^6$ cells/s.c. site; cytochrome P450 2B1-negative cells (parental 9L or 9L-Z cells) were injected in one thigh and cytochrome P450 2B1-positive cells (9L-ZP or L450-2 cells) in the other thigh. This strategy was employed to control any potential effects that subcutaneous growth of the 9L tumor might have on liver cytochrome P450-dependent cyclophosphamide activation activity. Drug treatment was initiated seven days after tumor implantation. Rats were randomized and divided into two groups. One group was treated with cyclophosphamide at 100 mg/kg body weight given as a single intraperitoneal injection. Another group was injected with saline as control. Tumor size was monitored by caliper measurement at times ranging up to 7–8 weeks, at which point the animals were sacrificed.

Western Blot and cytochrome P450 2B1 Activity Analysis: Microsomal proteins prepared from cultured 9L cells by differential centrifugation were electrophoresed through 10% sodium dodecyl sulfate/polyacrylamide gels (20 μg protein/lane), transferred to nitrocellulose and then probed with polyclonal rabbit anti-cytochrome P450 2B1 antibodies (Waxman and Walsh, *J. Biol. Chem.* 257:10446–10457 (1982); Waxman, D. J., *Methods Enzymol.* 206:249–267 (1991)). Phenobarbital-induced rat liver microsomes (1 μg) were used as a positive control. Cytochrome P450 2B1-dependent enzyme activity was measured by monitoring 7-ethoxycoumarin O-deethylation (Waxman and Walsh, *Biochemistry* 22:4846–4855 (1983)) and testosterone 16β-hydroxylation (Waxman, D. J., *Methods Enzymol.* 206:249–267 (1991)) in isolated 9L microsomal fractions.

Results

Stable expression of cytochrome P450 2B1 gene in 9L gliosarcoma cells: 9L cells were co-transfected with an expression plasmid encoding rat cytochrome P450 2B1 and a β-galactosidase expression plasmid containing a neomycin resistance gene in a 10:1 molar ratio. Cell lines resistant to G418 were selected and cloned. Western blot analysis of isolated 9L cell microsomes using a rabbit polyclonal antibody specific to cytochrome P450 2B1 showed a single protein band of approximately 52 kD, corresponding to the molecular mass of purified cytochrome P450 2B1, in samples prepared from the clonal cell lines designated 9L-ZP and L450-2. No cytochrome P450 2B1 protein was detected in parental 9L cells or 9L-Z cells, which were shown to express β-galactosidase (x-gal staining), but not cytochrome P450 2B1 (FIG. 25). The clonal cell lines 9L, 9L-Z, 9L-ZP, and L450-2 were used for further studies. Analysis of cytochrome P450 2B1-dependent enzyme activity (see Methods) verified that the cytochrome P450 2B1 transformants 9L-ZP and L450-2 both express cytochrome P450 2B1 in an enzymatically active form and at a level corresponding to ~1-2% that of phenobarbital-induced rat liver, while cytochrome P450 2B1 activity (testosterone 16β-hydroxylation) was not detectable in parental 9L cells or in 9L-Z cells.

Effects of oxazaphosphorines on cultured 9L and 9L-ZP cells: The inventors first tested whether 9L cells, which express cytochrome P450 2B1, are sensitive to the cytotoxic effects of cyclophosphamide and ifosphamide. Cytochrome P450 2B1-positive cells (9L-ZP and L450-2) and cytochrome P450 2B1-negative cells (parental 9L and 9L-Z) were cultured with various concentrations of cyclophosphamide or ifosphamide. The number of viable cells present 5 days after drug treatment was then determined. As shown in FIG. 26A, cyclophosphamide inhibited the growth of cytochrome P450 2B1-positive cells in a concentration-dependent manner ($IC_{50}$~70 μM). Growth of cytochrome P450 2B1-positive cells was also inhibited by ifosphamide, but this required a somewhat higher drug concentration ($IC_{50}$~145 μM) (FIG. 26B). These findings are consistent with our earlier observation that cytochrome P450 2B1 activates ifosphamide with a 3–4 fold lower catalytic efficiency (Vmax/Km) than cyclophosphamide (Weber and Waxman, *Biochem. Pharmacol.* 45:1685–94 (1993)). In contrast, parental 9L cells and 9L-Z cells manifested no adverse effects when grown in the presence of millimolar concentrations of cyclophosphamide or ifosphamide. In control experiments, it was established that cytochrome P450 2B1-positive and cytochrome P450 2B1-negative cells are both inherently sensitive to activated cyclophosphamide, which was presented to the cells in the form of 4-hydroperoxy cyclophosphamide (FIG. 26C).

Effects of P450 enzyme inhibition on oxazaphosphorine sensitivity of cytochrome P450 2B1-positive 9L cells: In order to verify that the expression of cytochrome P450 2B1 per se is responsible for the chemosensitivity of the cytochrome P450 2B1-positive cells to cyclophosphamide and ifosphamide, a cytochrome P450 2B1-selective enzyme inhibitor, metyrapone (Waxman and Walsh, *Biochemistry* 22:4846–4855 (1983)), was used to inhibit cellular cytochrome P450 2B1 activity. In the presence of 10 μM metyrapone, the cytotoxic effects of cyclophosphamide and ifosphamide toward 9L-ZP cells were nearly eliminated (FIG. 27). By contrast, metyrapone did not block the cytotoxic effect of the chemically activated derivative, 4-hydroperoxy cyclophosphamide (FIG. 27), a finding that is consistent with metyrapone protection via inhibition of cytochrome P450 2B1-catalyzed oxazaphosphorine activation. Therefore, the chemosensitivity of cytochrome P450 2B1-expressing cells to cyclophosphamide and ifosphamide is dependent on the presence of a functional cytochrome P450 2B1 enzyme within these cells.

Analysis of "bystander" cytotoxicity effect: The inventors next examined whether cytochrome P450 2B1-negative 9L cells can be rendered susceptible to cyclophosphamide cytotoxicity when co-cultured with cytochrome P450 2B1-expressing tumor cells. Parental 9L cells and cytochrome P450 2B1-positive 9L-ZP cells were used for these experiments, since they have similar doubling times in culture. Equal numbers of 9L and 9L-ZP cells were mixed, and the mixed culture was then treated with cyclophosphamide. It was expected that if cyclophosphamide cytotoxicity was restricted to the cytochrome P450 2B1-positive cells, then the total cell number would be decreased by approximately 50% compared to drug-free controls, as predicted on the basis of the selective, but nearly complete (>90%) cytotoxicity of cyclophosphamide toward 9L-ZP cells, which comprise half of the mixed cell population. On the other hand, if the cytochrome P450 2B1-positive cells chemosensitize the adjacent cytochrome P450 2B1-negative cells, then both cell types should be eliminated following treatment of the co-culture with cyclophosphamide.

As shown in FIG. 28, nearly 80% of the total cell population was eradicated when the mixed culture was treated with cyclophosphamide. Moreover, the cytochrome P450 2B1 enzyme inhibitor, metyrapone, could largely abrogate this effect. The cells in the mixed culture showed a similar pattern of sensitivity to ifosphamide, albeit at a somewhat higher drug concentration. In contrast, there was no killing of either cell population when 9L-Z cells were mixed with parental 9L cells. These studies demonstrate that cytochrome P450 2B1-positive cells confer a bystander killing effect on adjacent cytochrome P450 2B1-negative cells by a mechanism that involves cytochrome P450 2B1 enzyme activity.

The effect of cyclophosphamide treatment on both the cytochrome P450 2B1-negative and the cytochrome P450 2B1-positive cells within the mixed cell population was then monitored. Cells marked with the lac Z gene (β-galactosidase), which can be identified as blue cells after staining the cultures with the β-galactosidase substrate x-gal, were employed to distinguish the two types of cells in culture. Equal numbers of parental 9L cells were mixed with lac Z-marked cytochrome P450 2B1-positive cells, 9L-ZP. Following cyclophosphamide treatment, cells were fixed and stained with x-gal to reveal the cytotoxicity of cyclophosphamide to the two cell populations. As illustrated in FIG. 29, cyclophosphamide dramatically inhibited growth of the cytochrome P450 2B1-positive cells (blue stained cells). A substantial, albeit somewhat lower inhibition of the growth of the cytochrome P450 2B1-negative cells (unstained cells) was observed. The few remaining cells showed marked morphologic abnormalities and viability of the remaining cells was questionable. The cytochrome P450 2B1 inhibitor metyrapone protected both cell types from cyclophosphamide killing; however, microscopic evaluation revealed morphologic distortions in some of the cytochrome P450 2B1-positive cells, but not in the cytochrome P450 2B1-negative cells. These findings indicate that 9L cells that express cytochrome P450 2B1 are more susceptible to cyclophosphamide cytotoxicity as a consequence of prodrug activation that occurs within the tumor cell, but that substantial cytotoxicity toward adjacent cytochrome P450 2B1-negative cells also occurs.

The inventors next assessed whether this bystander killing of cytochrome P450 2B1-negative cells by the adjacent cytochrome P450 2B1-positive cells requires direct cell-cell contact, by analogy with the case of HSV-TK-positive and HSV-TK-negative tumor cells and ganciclovir treatment (Ram et al., *Cancer Res.* 53:83–88 (1993); Culver et al., *Science* 256: 1550–1552 (1992); Freeman et al., *Cancer Res.* 53:5274–5283 (1993); Bi et al., *Human Gene Therapy* 4:725–731 (1993)). For these experiments, parental 9L cells were seeded in the bottom chamber of Falcon co-culture inserts, and either cytochrome P450 2B1-positive cells (9L-ZP) or cytochrome P450 2B1-negative cells (9L-Z) were placed in the top chamber of the co-culture inserts. The two cell populations were physically separated in this co-culture system, but shared the same culture medium.

As shown in FIG. 30A, cyclophosphamide treatment for 5 days killed not only the cytochrome P450 2B1-positive 9L cells in the top chamber, but also the parental 9L cells cultured in the bottom chamber. The killing of both cell populations can be effectively blocked by the cytochrome P450 2B1 inhibitor metyrapone. In contrast, there was no killing of either cell population when 9L-Z cells were co-cultured with parental 9L cells.

To assess whether the bystander killing of co-cultured cytochrome P450 2B1-negative cells is dependent on the number of co-cultured cytochrome P450 2B1-positive cells, a variable number of 9L-ZP cells (ranging from 104 to 106 cells) was placed in Falcon culture inserts and co-cultured with $10^5$ parental 9L cells. FIG. 30B demonstrates that the cytotoxicity of cyclophosphamide towards the 9L cells in the bottom culture chamber (shown on the y-axis) is directly correlated with the initial number of 9L-ZP cells in the top chamber (x-axis). Thus, in the case of cytochrome P450 2B1/cyclophosphamide, the bystander killing effect is at least partly due to the transfer of the non-cytochrome P450 expressing cells of soluble cytotoxic metabolite(s) formed via cytochrome P450-catalyzed drug metabolism. This bystander effect is therefore distinct from that of the HSV-TK/ganciclovir system, where intimate cell-cell contact is necessary for bystander cytotoxicity to occur (Freeman et al., *Cancer Res.* 53:5274–5283 (1993); Bi et al., *Human Gene Therapy* 4:725–731 (1993)).

Effects of cytochrome P450 2B1 expression on cyclophosphamide-sensitivity of 9L tumors in vivo: The studies described above establish that 9L gliosarcoma cells that are stably transfected to express cytochrome P450 2B1 become highly sensitive to cyclophosphamide and ifosphamide cytotoxicity. The inventors next employed these cells as an ex vivo gene transfer model to evaluate in vivo the feasibility of employing the cytochrome P450 2B1/oxazaphosphorine system for cancer gene therapy. An in vivo tumor growth delay study was carried out to compare the cyclophosphamide sensitivity of cytochrome P450 2B1-negative 9L tumors to that of cytochrome P450 2B1-expressing 9L tumors. Cytochrome P450 2B1-negative cells (9L and 9L-Z) and cytochrome P450 2B1-expressing cells (9L-ZP and L450-2) were grown subcutaneously as solid tumors in female Fischer 344 rats. Cyclophosphamide treatment of cytochrome P450 2B1-expressing tumors led to complete inhibition of tumor growth (Table VI and FIG. 31). 9L tumors showed some growth delay following cyclophosphamide treatment, but this anti-tumor effect was short-term, with aggressive tumor growth eventually returning. The temporary growth delay of the parental 9L tumors results from activation of cyclophosphamide by cytochrome P450 present in the liver, which in the case of adult female rats is primarily catalyzed by cytochrome P450 form 2C6 (Clarke and Waxman, *Cancer Res.* 49:2344–50 (1989)). These in vivo tumor model studies establish that intratumoral expression of the cytochrome P450 2B1 gene, and the associated intratumoral prodrug activation, can render peripheral solid tumors highly susceptible to oxazaphosphorine treatment in vivo.

TABLE VI

Effect of cyclophosphamide on cytochrome P450 2B1-negative and cytochrome P450 2B1-positive 9L tumors grown subcutaneously in Fischer 344 rats

| Tumor | Complete Tumor Growth Inhibition[a] | |
|---|---|---|
| | Saline | Cyclophosphamide |
| 9L | 0/11 | 0/11 |
| 9L-Z | 0/9 | 0/9 |
| 9L-ZP | 0/9 | 8/9 |
| L450-2 | 0/11 | 11/11 |

[a]Rats were injected with 2 × 10⁶ cytochrome P450 2B1-negative tumor cells (9L or 9L-Z) or cytochrome P450 2B1-positive tumor cells (9L-Z of L450-2). Cyclophosphamide was administered as a single intraperitoneal injection at 100 mg/kg body weight 7 days after tumor implantation. The completeness of tumor growth inhibition in the cyclophosphamide-treated 9L-ZP and L450-2 tumors was assessed by palpation or by anatomical examination 7–8 weeks after cyclophosphamide treatment. Results were combined from three independent experiments and are presented as the number of tumors showing complete tumor growth inhibition/total number of tumors studied. Representative tumor growth curves for an experiment involving 9L-Z and 9L-ZP tumors are shown in FIG. 26.

Discussion

Rat 9L gliosarcoma cells were used as a model to assess the utility of cytochrome P450 gene transfer as a paradigm for chemosensitization of tumors by introduction of genes for drug-metabolizing enzymes that activate known, established cancer chemotherapeutic agents. 9L cells, originated from a rat brain tumor (Barker et al., *Cancer Res.* 33:976–986 (1973)), can be grown in culture, or can be implanted either subcutaneously or intracranially in Fischer 344 rats. 9L cells express cytochrome P450 reductase, which transfers electrons required for all microsomal cytochrome P450-dependent enzyme reactions, but contain little or no endogenous cytochrome P450 enzyme activity, making them well suited as a recipient cell line for experiments involving cytochrome P450 gene transfer. The primary goals of the present studies were (a) to evaluate whether expression of cytochrome P450 2B1 in this tumor cell line sensitizes the tumor cells to oxazaphosphorines, (b) to establish whether adjacent, non-cytochrome P450-containing tumor cells become drug-sensitive via a "bystander effect," and (c) to ascertain whether this chemosensitization in vitro translates into a therapeutic advantage in vivo in the case of a peripheral tumor, and in the context of an intact liver system, which catalyzes oxazaphosphorine activation at a rate that greatly exceeds that of the tumor itself. Transfer of the oxazaphosphorine-activating cytochrome P450 2B1 gene into 9L tumor cells does, indeed, render these cells preferentially susceptible to cyclophosphamide and ifosphamide, both in vitro and in vivo, and therefore, is likely to be useful for application to cancer therapy.

In vitro and in vivo studies of the HSV-TK/ganciclovir system have indicated that HSV-TK transduced cells treated with ganciclovir exert a "bystander killing" of non-HSV-TK transduced cells which they contact (Ram et al., *Cancer Res.* 53:83–88 (1993); Culver et al., *Science* 256:1550–1552 (1992); Freeman et al., *Cancer Res.* 53:5274–5283 (1993); Bi et al., *Human Gene Therapy* 4:725–731 (1993)). The precise mechanistic basis for the bystander killing effect remains unclear, but it appears to involve transfer of activated ganciclovir metabolites or other toxic substances through cell-cell contact. This bystander effect can be of great therapeutic significance because it indicates that eradication of the tumor can, in principle, be achieved even if only a subset of a tumor cell population is effectively transduced with the drug sensitivity gene.

Consequently, experiments were conducted to determine whether cytochrome P450 gene transfer is associated with a bystander effect, i.e., whether cytochrome P450-expressing tumor cells can sensitize adjacent tumor cells to cyclophosphamide. It was observed that cytochrome P450 2B1-positive cells do confer a bystander killing of cytochrome P450 2B1-negative cells by a mechanism that requires enzymatically active cytochrome P450 2B1. This bystander killing effect involves, at least in part, intercellular transfer of soluble cytotoxic metabolite(s), as indicated by the chemosensitivity conferred by 9L-ZP cells to parental 9L cells even when contact between the two cell populations is prevented. Conceivably, the bystander killing that was observed could additionally involve cell-cell contact mechanisms as well. 4-Hydroxycyclophosphamide formed by cytochrome P450 2B1 is believed to be readily diffusible across cell membranes (Sladek, N. E., *Pharmacol Ther.* 37:301–355 (1988)), and it is likely that the release of this primary metabolite, or perhaps its cytotoxic decomposition products, phosphoramide mustard and acrolein, contribute to the lethal effect of cyclophosphamide on neighboring cytochrome P450 2B1-negative cells. Other mechanisms, such as, the transfer of apoptotic signals from dying 9L-ZP cells to 9L cells, could also play a role.

The lack of a requirement for cell-cell contact to achieve cytochrome P450 2B1/cyclophosphamide bystander cytotoxicity may represent an important therapeutic advantage of cytochrome P450 gene therapy over the HSV-TK/ganciclovir system by providing for more extensive distribution of activated drug within a tumor mass. In addition, unlike HSV-TK/ganciclovir, which produces activated metabolites whose cytotoxicity is limited to cells in the DNA synthesis (S phase) of the cell cycle, the cytochrome P450 2B1/oxazaphosphorine system generates metabolites that are effective in killing tumor cells in a cell cycle-independent manner. Thus, the toxicity to tumor cells of phosphoramide mustard-derived interstrand DNA cross-links becomes manifest at whichever point the tumor cells begin to replicate, resulting in a higher fractional tumor cell kill.

Another potential advantage of cytochrome P450-based cancer gene therapy is the possibility of augmenting a drug's local anti-tumor effect, via cytochrome P450 gene transfer, in combination with the selective inhibition of the liver cytochrome P450 enzymes involved in systemic prodrug activation. Since the cytochrome P450 catalysts of oxazaphosphorine activation in human liver (Chang et al., Cancer Res. 53:5629–5637 (1993)) are biochemically distinct from rat cytochrome P450 2B1, liver cytochrome P450 inhibition may therefore be achievable by using appropriate cytochrome P450 isoform-selective inhibitors (Chang et al., Cancer Res. 53:5629–5637 (1993); Guengerich et al., Chem. Res. Toxicol. 4:391–407 (1991); Chang et al., Arch. Biochem. Biophy. 311:437–442 (1994)). This could provide a significant therapeutic advantage by minimizing the host tissue toxicity that results from the liver cytochrome P450-mediated systemic exposure to activated metabolites, which invariably occurs during conventional chemotherapy.

An important finding is that cytochrome P450 2B1/cyclophosphamide is highly effective with respect to its chemotherapeutic potential in vivo, in the case of a solid tumor grown in the periphery, and thus, is a good candidate for further preclinical development as a target for cancer gene therapy. The striking therapeutic advantage conferred by intratumoral cytochrome P450 2B1 expression (FIG. 31 and Table VI) is surprising for several reasons, and could not have been predicted from the findings of brain tumor gene therapy studies cited elsewhere in this application.

First, endogenous cytochrome P450 enzymes active in cyclophosphamide metabolism are already expressed at high levels in liver tissue. Moreover, at the time of cyclophosphamide treatment, 7 days after tumor implantation, the 9L tumors in this study were just palpable, and thus, were small in size compared to liver. In addition, the specific content of cytochrome P450 protein in the cytochrome P450 2B1-transfected tumor cells is low compared to liver (cf., FIG. 25). Thus, the major fraction of activated cyclophosphamide in circulation in the 9L-ZP and the L450-2 tumor-bearing rats is undoubtedly liver-derived rather than tumor-derived. Nevertheless, complete tumor regression following cyclophosphamide treatment was observed in both of these 9L/cytochrome P450 2B1 tumors, but not in the cytochrome P450 2B1-negative 9L and 9L-Z tumors. This indicates that there likely is a very substantial "proximity effect" in the case of intratumoral cyclophosphamide activation. This may indicate that the primary metabolite 4-hydroxycyclophosphamide/aldophosphamide, or perhaps its plasma protein-stabilized sulfhydro adduct (Hohorst et al., Adv. Enzyme Regul. 25:99–122 (1986)), has less access to the tumor vasculature or a lower degree of cell membrane permeability when formed in the liver than would be anticipated on the basis of earlier studies (Sladek, N. E., Pharmacol. Ther. 37:301–355 (1988); Hong et al., Drug Metab. Dispos. 19:1–7 (1991)). Alternatively, given the short intrinsic half-life of 4-hydroxycyclophosphamide [$t_{1/2}$=5.2 and 3.3 min in rat and human plasma, respectively; Id.], significant decomposition of this primary metabolite may occur before it reaches the tumor from its site of generation in the liver. Thus, the effective intratumoral concentration of alkylating metabolites may be substantially higher in the case of cytochrome P450 2B1-expressing 9L tumors as compared to non-cytochrome P450 2B1-expressing 9L tumors, despite the much higher inherent metabolic capacity of liver in these rats.

An additional possibility is that the substantially enhanced cytotoxicity of cyclophosphamide toward cytochrome P450 2B1-expressing 9L tumors results from sensitization of the tumor cells to phosphoramide mustard, the primary DNA-alkylating metabolite, by the protein-alkylating metabolite acrolein. Acrolein, derived from 4-hydroxycyclophosphamide/aldophosphamide by chemical decomposition, is formed in equimolar amounts with phosphoramide mustard, and is an important contributing factor to cyclophosphamide-associated cardiotoxicity (Friedman et al., Cancer Res. 50:2455–2462 (1990))and to the endocrine toxicities that cyclophosphamide can have, as indicated by the depletion of serum testosterone levels and the modulation of liver cytochrome P450 and steroid metabolizing enzyme profiles following cyclophosphamide treatment (Chang and Waxman, Cancer Res. 53:2490–2497 (1993)). Although acrolein derived from liver cyclophosphamide activation does not mediate the parent drug's antitumor activity (Sladek, N. E. (1988), supra), it is conceivable that in our cytochrome P450 gene transfer/intratumoral cyclophosphamide activation model, acrolein formed locally potentiates the cytotoxic effects of phosphoramide mustard, perhaps by a glutathione depletion mechanism (cf., (Friedman et al., Cancer Res. 50:2455–2462 (1990); Gurtoo et al., Cancer Res. 41:3584–3591 (1981)).

In conclusion, this Example demonstrates the therapeutic utility of transferring oxazaphosphorine-activating cytochrome P450 genes into peripheral tumor cells. These studies demonstrate that the killing of peripheral tumor cells may proceed in an efficient manner even if only a subset of a tumor cell population is efficiently transfected with the drug-activating cytochrome P450 gene. A substantial improvement in the therapeutic activity of cyclophosphamide or ifosphamide, as well as N,N',N"-triethylenethiophosphoramide (thio-TEPA), procarbazine, dacarbazine, and other anti-tumor agents activated by this or other cytochrome P450 genes (LeBlanc and Waxman, Drug Metab. Rev. 20:395–439 (1989); Ng and Waxman, International Journal of Oncology 2:731–738 (1993); Ng and Waxman, Cancer Research 51:2340–2345 (1991); Ng and Waxman, Cancer Research 50:464–471 (1990)), against peripheral tumors may thus be expected when these drugs are combined with cytochrome P450 gene transfer. This is predicted even if the efficiency of the cytochrome P450 gene transfer that can be achieved using viral vectors or other novel gene transfer approaches, including use of tumor-specific promoter DNA sequences, is less than 100% with respect to gene transduction into tumor cells. Thus, the utility of the present invention includes the achievement of more optimal drug efficacy by increasing the specificity and selectivity of anti-cancer drugs, such as the oxazaphosphorines, while minimizing the systemic toxicity traditionally associated with the use of these drugs.

Finally, the chemotherapy/gene therapy concepts and strategies developed in this invention may potentially be extended to other established cancer chemotherapeutic agents (LeBlanc and Waxman, Drug Metab. Rev. 20:395–439 (1989); Ng and Waxman, International Journal of Oncology 2:731–738 (1993); Ng and Waxman, Cancer Research 51:2340–2345 (1991); Ng and Waxman, Cancer Research 50:464–471 (1990)) and other cytochrome P450 genes (Nelson et al., DNA Cell Biol. 12:1–51 (1993)).

EXAMPLE 8

In order to determine whether the sensitivity to cyclophosphamide conferred by cytochrome P450 2B1 gene expression in the case of rat 9L gliosarcoma cells will translate into enhanced therapeutic activity in other tumor cell types, a panel of MCF-7 human breast carcinoma cell lines that stably express cytochrome P450 2B1 was prepared and then evaluated for sensitivity to cyclophosphamide both in vitro and in vivo using a nude mouse model.

Methods

MCF-7 is a human breast carcinoma cell line that was initiated from a pleural effusion of a post menopausal nulliparous woman. This human tumor cell line can be grown and passaged both in cell culture and in nude mice, where it grows as a solid tumor. It is a widely studied model for human breast cancer, known to those skilled in the an (Soule et al., *J. Natl. Cancer Inst.* 51:1409–1413 (1973)).

MCF-7 cells were grown as a monolayer in Dulbecco's modified Eagle's medium with 10% heat-inactivated fetal bovine serum, 100 units penicillin/mL, 100 μg streptomycin/mL, 2mM L-glutamine, and 0.25 unit insulin/mL.

Transfection of MCF-7 cells with the cytochrome P450 2B1 expression plasmid, selection of neomycin-resistant clones, characterization of the expressed cytochrome P450 2B1 protein, and sensitivity of cell lines to drugs were carried out as described in Example 7 for the 9L cytochrome P450 2B1-expressing cell lines.

Female homozygous (nu+\nu+) nude athymic Swiss mice (Soule et al., *Cancer Letters* 10:177–189 (1980)), 20–25 g, were obtained from Taconic Inc. (Germantown, N.Y.).

MCF-7 cells or stable MCF-7 cell transfectants expressing cytochrome P450 2B1 or *E. coli* β-galactosidase (lacZ) were grown in cell culture. Cells in the exponential growth phase were harvested and then injected subcutaneously ($1\times10^7$ cells in 0.2 mL) in the flanks of nude mice. A single 17β-estradiol pellet (1.7 mg hormone/60-day release pellet, Innovative Research, Toledo, Ohio) was implanted one day before tumor inoculation. At one month after tumor inoculation, the size of each tumor was measured using a vernier caliper.

Nude mice were then treated with cyclophosphamide given at 100 mg/kg body weight×2, by intraperitoneal injection given on day 0 and again on day 2. Tumor size measurements were then again determined using a vernier caliper, and data are expressed relative to tumor sizes as of day 0, the day of initial cyclophosphamide (CPA) injection.

Results

FIG. 32 demonstrates that parental MCF-7 cells, as well as an MCF-7 transfected control cell line that expresses the bacterial enzyme beta-galactosidase, MCF-7-Z3, are both insensitive to high concentrations of cyclophosphamide. In contrast, six individual cytochrome P450 2B1-expressing MCF-7 cell lines, designated P2, P3, P5, P8, P9 and P26, were each highly sensitive to cyclophosphamide cytotoxicity. Furthermore, when the cytochrome P450 2B1-expressing MCF-7 cells were grown subcutaneously in vivo in a nude mouse tumor model, the P450 expressing cells were preferentially killed following cyclophosphamide treatment.

FIG. 33 compares the in vivo tumor cell kill obtained with four of the P450 expressing MCF-7 tumors (designated P3, P2, P9 and P26) to that of the control tumor MCF-7 Z3, which displayed only a moderate cyclophosphamide sensitivity that was indistinguishable from that of the parental MCF-7 tumor.

Discussion

These experiments establish that the therapeutic advantage of cytochrome P450 2B1 gene transfer is not limited to the 9L or C6 model system, but that it is observed in other tumors that are of non-CNS origin. Further, the results in this Example demonstrate that the cytotoxic effects observed using the cytochrome P450/CPA cancer therapy paradigm are not only observed with rodent tumors, but are also obtained with human tumors grown in vivo. Finally, these experiments again demonstrate that the cytochrome P450/CPA system can be used for cancer gene therapy, not only for central nervous system tumors, but also for peripheral tumors or peripheral metastatic tumors.

Modifications of the above-described modes for carrying out the invention that are obvious to persons of skill in medicine, molecular biology, immunology, hybridoma technology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application were specifically and individually indicated to be incorporated by reference.

Although the foregoing invention has been described in some detail by way of illustration and example for purposes of clarity of understanding, it will be obvious that certain changes and modifications can be practiced within the scope of the appended claims.

What is claimed is:

1. A method for selectively killing central nervous system tumor cells in a mammal, said method comprising:
    (a) infecting said tumor cells of said mammal with a viral vector, said vector carrying a cytochrome P450 gene, wherein expression of said gene by said tumor cells enables the enzymatic conversion of a chemotherapeutic agent to its cytotoxic form within said tumor, whereby said tumor cells become selectively sensitized to said agent; and
    (b) contacting said tumor cells with said chemotherapeutic agent whereby said tumor cells are selectively killed.

2. The method of claim 1, wherein said cytochrome gene is P450 2B1, P450 2B6, P450 2A6, P450 2C6, P450 2C8, P450 2C9, P450 2C11, or P450 3A4.

3. The method of claim 2, wherein said cytochrome gene is P450 2B1.

4. The method of claim 1, wherein said chemotherapeutic agent is cyclophosphamide or ifosphamide.

5. The method of claim 2, wherein said chemotherapeutic agent is cyclophosphamide or ifosphamide.

6. The method of claim 3, wherein said chemotherapeutic agent is cyclophosphamide.

7. The method of claim 1, wherein said central nervous system tumor cells are astrocytomas, oligodendrogliomas, meningiomas, neurofibromas, glioblastomas, ependymomas, Schwannomas, or neurofibrosarcomas.

8. The method of claim 5, wherein said central nervous system tumor cells are astrocytomas, oligodendrogliomas, meningiomas, neurofibromas, glioblastomas, ependymomas, Schwannomas, or neurofibrosarcomas.

9. The method of claim 2, wherein said viral vector is a retrovirus.

10. The method of claim 5, wherein said viral vector is a retrovirus.

11. A method for selectively killing central nervous system tumor cells in a mammal, said method comprising:
    (a) infecting said tumor cells of said mammal with a viral vector, said vector carrying a cytochrome P450 2B1 gene, wherein expression of said gene by said tumor cells enables the enzymatic conversion of cyclophosphamide to its cytotoxic form within said tumor, whereby said tumor cells become selectively sensitized to cyclophosphamide; and
    (b) contacting said tumor cells with said cyclophosphamide whereby said tumor cells are selectively killed.

12. A method for selectively killing peripheral tumor cells in a mammal, said method comprising:

(a) infecting said tumor cells said mammal with a viral vector, said vector carrying a cytochrome P450 gene, wherein expression of said gene by said tumor cells enables the enzymatic conversion of a chemotherapeutic agent to its cytotoxic form within said tumor, whereby said tumor cells become selectively sensitized to said agent; and (b) contacting said tumor cells with said chemotherapeutic agent whereby said tumor cells are selectively killed.

13. The method of claim 12, wherein said cytochrome gene is P450 2B1, P450 2B6, P450 2A6, P450 2C6, P450 2C8, P450 2C9, P450 2C11, or P450 3A4.

14. The method of claim 13, wherein said cytochrome gene is P450 2B1.

15. The method of claim 12, wherein said chemotherapeutic agent is cyclophosphamide or ifosphamide.

16. The method of claim 13, wherein said chemotherapeutic agent is cyclophosphamide or ifosphamide.

17. The method of claim 14, wherein said chemotherapeutic agent is cyclophosphamide or ifosphamide.

18. The method of claim 17, wherein said chemotherapeutic agent is cyclophosphamide.

19. The method of claim 13, wherein said viral vector is a retrovirus.

20. The method of claim 16, wherein said viral vector is a retrovirus.

21. The method of claim 12, wherein said peripheral tumor cells are breast tumor cells.

22. The method of claim 13, wherein said peripheral tumor cells are breast tumor cells.

23. The method of claim 14, wherein said peripheral tumor cells are breast tumor cells.

24. The method of claim 15, wherein said peripheral tumor cells are breast tumor cells.

25. The method of claim 16, wherein said peripheral tumor cells are breast tumor cells.

26. The method of claim 17, wherein said peripheral tumor cells are breast tumor cells.

27. The method of claim 18, wherein said peripheral tumor cells are breast tumor cells.

* * * * *

UNITED STATES PATENT AND TRADEMARK OFFICE
CERTIFICATE OF CORRECTION

PATENT NO. : 5,688,773  Page 1 of 2

DATED : November 18, 1997

INVENTOR(S) : Chiocca et al.

It is certified that error appears in the above-identified patent and that said Letters Patent is hereby corrected as shown below:

Page 2, column 1, under the heading "Other Publications", line 41, delete "Chana" and insert therefor --Chang--.

Page 4, column 2, under the heading "Other Publications", line 1, delete "Infected" and insert therefor --Injected--.

Page 4, column 2, under the heading "Other Publications", line 18, insert "*46*," after "*Cancer Res.*".

Page 5, column 2, under the heading "Other Publications", last line, delete "*Nurosci.*" and insert therefor --*Neurosci.*--.

Page 6, column 1, under the heading "Other Publications", line 29, delete "HeDatic" and insert therefor --Hepatic--.

Figure 3, sheet 3 of 33, delete "C6BWT, C6BAG" and insert therefor --C6BWT, C6BBAG--.

Figure 6, sheet 6 of 33, delete "C6BAG + C6BU1" and insert therefor --C6BBAG + C6BU1--.

Figure 6, sheet 6 of 33, delete "C6BAG + C6VIK" and insert therefor --C6BBAG + C6VIK--.

Figure 14, sheet 14 of 33, delete "C6 0 — o" and insert therefor --C6 o—o --.

Column 4, line 5, delete "et at." and insert therefor --*et al.*--.

Column 5, line 47, insert a new paragraph after "tumor cells."

UNITED STATES PATENT AND TRADEMARK OFFICE
CERTIFICATE OF CORRECTION

PATENT NO. : 5,688,773

DATED : November 18, 1997

INVENTOR(S) : Chiocca et al.

It is certified that error appears in the above-identified patent and that said Letters Patent is hereby corrected as shown below:

Column 16, line 18, delete "liters" and insert therefor --titers--.

Column 18, line 66, delete "μ-galactosidase" and insert therefor --β-galactosidase--.

Column 26, line 58, delete "liter" and insert therefor --titer--.

Column 28, line 63, delete "minor" and insert therefor --tumor--.

Column 39, line 13, delete "rate liver" and insert therefor --rat liver--.

Column 50, line 25, delete "coffer" and insert therefor --confer--.

Column 53, line 14, delete "drag" and insert therefor --drug--.

Column 54, line 65, delete "104 to 106" and insert therefor --$10^4$ to $10^6$--.

Column 59, line 13, delete "an" and insert therefor --art--.

Column 61, line 1, after "tumor cells" insert --of--.

Signed and Sealed this

Twenty-sixth Day of May, 1998

Attest:

Attesting Officer

BRUCE LEHMAN

Commissioner of Patents and Trademarks